US012790306B2

(12) United States Patent
Hie et al.

(10) Patent No.: US 12,790,306 B2
(45) Date of Patent: Nov. 10, 2026

(54) FUNGICIDAL SUBSTITUTED HETEROCYCLES

(71) Applicant: FMC Corporation, Philadelphia, PA (US)

(72) Inventors: Liana Hie, Wilmington, DE (US); Jeffrey Keith Long, Wilmington, DE (US); Daniel Akwaboah, Middletown, DE (US); Ravisekhara P. Reddy, Secunderabad (IN); Paula Louise Sharpe, Middletown, DE (US); Thomas Martin Stevenson, Newark, DE (US); Alexander Robert White, San Diego, CA (US)

(73) Assignee: FMC Corporation, Philadelphia, PA (US)

( * ) Notice: Subject to any disclaimer, the term of this patent is extended or adjusted under 35 U.S.C. 154(b) by 348 days.

(21) Appl. No.: 18/684,330

(22) PCT Filed: Aug. 18, 2022

(86) PCT No.: PCT/US2022/040739

§ 371 (c)(1),
(2) Date: Feb. 16, 2024

(87) PCT Pub. No.: WO2023/023242

PCT Pub. Date: Feb. 23, 2023

(65) Prior Publication Data

US 2024/0308968 A1 Sep. 19, 2024

Related U.S. Application Data

(60) Provisional application No. 63/234,447, filed on Aug. 18, 2021.

(51) Int. Cl.

| | |
|---|---|
| ***C07D 237/08*** | (2006.01) |
| ***A01N 43/40*** | (2006.01) |
| ***A01N 43/54*** | (2006.01) |
| ***A01N 43/58*** | (2006.01) |
| ***A01N 43/72*** | (2006.01) |
| ***A01P 3/00*** | (2006.01) |
| ***C07D 213/30*** | (2006.01) |
| ***C07D 213/85*** | (2006.01) |
| ***C07D 239/26*** | (2006.01) |
| ***C07D 239/54*** | (2006.01) |
| ***C07D 265/02*** | (2006.01) |
| ***C07D 401/06*** | (2006.01) |
| ***C07D 409/12*** | (2006.01) |

(52) U.S. Cl.

CPC ........... *C07D 237/08* (2013.01); *A01N 43/40* (2013.01); *A01N 43/54* (2013.01); *A01N 43/58* (2013.01); *A01N 43/72* (2013.01); *A01P 3/00* (2021.08); *C07D 213/30* (2013.01); *C07D 213/85* (2013.01); *C07D 239/26* (2013.01); *C07D 239/54* (2013.01); *C07D 265/02* (2013.01); *C07D 401/06* (2013.01); *C07D 409/12* (2013.01)

(58) Field of Classification Search

CPC ....... A01P 3/00; C07D 213/26; C07D 213/30; C07D 213/63; C07D 213/85; C07D 237/08; C07D 237/14; C07D 237/16; C07D 237/22; C07D 237/24; C07D 239/26; C07D 239/54; C07D 261/12; C07D 265/02; C07D 401/04; C07D 401/06; C07D 403/04; C07D 405/04; C07D 409/12; C07D 417/04

See application file for complete search history.

(56) References Cited

U.S. PATENT DOCUMENTS

| | | | |
|---|---|---|---|
| 7,915,258 B2 | 3/2011 | Congy et al. |
| 2007/0249579 A1 | 10/2007 | Wang et al. |
| 2009/0163545 A1 | 6/2009 | Goldfarb |
| 2012/0329787 A1 | 12/2012 | Stevenson |
| 2018/0279614 A1 | 10/2018 | Umetani et al. |

(Continued)

FOREIGN PATENT DOCUMENTS

| | | |
|---|---|---|
| CN | 109232543 A | 1/2019 |
| EP | 0402227 A1 | 12/1990 |

(Continued)

OTHER PUBLICATIONS

Coelho, et al., Straightforward Entry to Libraries of Diversely Substituted Azinones by a Consecutive Aza-Michael/ Palladium-Catalyzed Functionalization Strategy, Journal of Combinatorial Chemistry, 2006, vol. 8, No. 3, pp. 388-400.

(Continued)

*Primary Examiner* — Savitha M Rao
(74) *Attorney, Agent, or Firm* — Charlene G. Sternberg; FMC Corporation

(57) ABSTRACT

Disclosed are compounds of Formula 1 including all geometric and stereoisomers, N-oxides, and salts thereof,

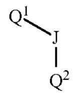

1 wherein $Q^1$, $Q^2$ and J are as defined in the disclosure.

Also disclosed are compositions containing the compounds of Formula 1 and methods for controlling plant disease caused by a fungal pathogen comprising applying an effective amount of a compound or a composition of the invention.

9 Claims, No Drawings

(56) References Cited

U.S. PATENT DOCUMENTS

| | | | |
|---|---|---|---|
| 2019/0380340 | A1 | 12/2019 | Umetani et al. |
| 2021/0100782 | A1 | 4/2021 | Umetani et al. |

FOREIGN PATENT DOCUMENTS

| | | | |
|---|---|---|---|
| JP | H01258671 | A | 10/1989 |
| WO | 2004/009560 | A1 | 1/2004 |
| WO | 2004/029204 | A2 | 4/2004 |
| WO | 2005/049581 | A1 | 6/2005 |
| WO | 2011/042389 | A2 | 4/2011 |

OTHER PUBLICATIONS

International Search Report of Corresponding PCT/US2022/040739 patent application.

Dajka-Halasz, et al., Study of tert-amino effect: the role of substituents in isomerization of 5-amino-4-vinyl-3(2H)-pyridazinones, ARKIVOC, 2008 (iii), pp. 102-126.

Barsy, et al., Novel Synthesis of Polyfunctionalised Biaryl, Pyridazine, and Phthalazine Derivatives, Synthetic Communications, 31(17), pp. 2569-2581.

Estevez, et al., Pyridazines, XV, Synthesis of 6-Aryl-5-Amino-3(2H)-pyridazinones as Potential Platelet Aggregation Inhibitors, J. Heterocyclic Chem, 1998, vol. 35, pp. 1421-1428.

Lack, et al., Correction to Targeting the Binding Function 3 (BF3) Site of the Human Androgen Receptor through Visual Screening, Journal of Medicinal Chemistry, 2012, vol. 55, pp. 565.

Elnagdi, et al. Studies of Polyfunctionalised Heteroaromatics: a Novel Synthesis of Polyfinctionalised Pyridine, Pyridazine and Pyrido[2,3-c]pyridazine Derivatives, J. Chem Research, 1998, pp. 26-27.

Giovannoni, et al., 4-Amino-5-substituted-3(2H)-pyridazinones as Orally Active Antinociceptive Agents: Synthesis and Studies on the Mechanism of Action, J. Chem Med., 2007, vol. 50, No. 16 pp. 3945-3953.

FUNGICIDAL SUBSTITUTED HETEROCYCLES

FIELD OF THE INVENTION

This invention relates to certain substituted heterocycles, their N-oxides, salts and compositions, and methods of using them as fungicides.

BACKGROUND OF THE INVENTION

The control of plant diseases caused by fungal plant pathogens is extremely important in achieving high crop efficiency. Plant disease damage to ornamental, vegetable, field, cereal and fruit crops can cause significant reduction in productivity and thereby result in increased costs to the consumer. Many products are commercially available for these purposes, but the need continues for new compounds which are more effective, less costly, less toxic, environmentally safer or have different sites of action.

PCT patent publications WO 2004/009560 A1 and WO 2004/029204 A2 disclose certain pyrimidine derivatives and their use as pharmaceuticals.

US 2019/380340 A1, US 2021100782 A1 and US 2018279614 A1 disclose certain pyridone derivatives and their use as agricultural compositions.

US 2012/0329787 A1 disclose certain oxazinone derivatives and their use as fungicides.

SUMMARY OF THE INVENTION

This invention is directed to compounds of Formula 1 (including all stereoisomers), N-oxides, and salts thereof, compositions containing them and their use as fungicides:

1

wherein

J is selected from the group consisting of:

J-1

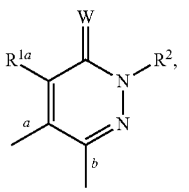

J-2

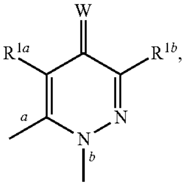

-continued

J-3

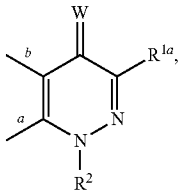

J-4

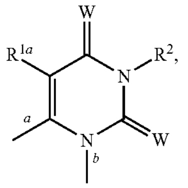

J-5

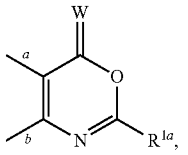

J-6

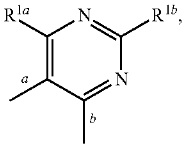

J-7

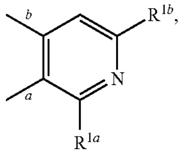

J-8

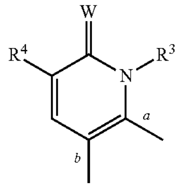

and

J-9

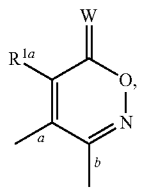

wherein the bond of J-1, J-2, J-3, J-4, J-5, J-6, J-7, J-8 or J-9 which is identified with “a” is connected to $Q^1$ of Formula 1, and the bond which is identified with “b” is connected to $Q^2$ of Formula 1;

each W is independently O or S;

$Q^1$ and $Q^2$ are each independently a phenyl ring optionally substituted with up to 5 substituents independently selected from $R^5$; or a 5- to 6-membered heteroaromatic ring, each ring containing ring members selected from carbon atoms and 1 to 4 heteroatoms independently selected from up to 2 O, up to 2 S and up to 4 N atoms, each ring optionally substituted with up to 5 substituents independently selected from $R^5$; or a 3- to 6-membered nonaromatic heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and $S(=O)_2$, each ring optionally substituted with up to 5 substituents independently selected from $R^5$;

$R^{1a}$ and $R^{1b}$ are each independently H, halogen, cyano, hydroxy, nitro, amino, $C(=O)NR^{6a}R^{6b}$, C(=O)OH, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_2$-$C_6$ cyanoalkyl, $C_1$-$C_6$ hydroxyalkyl, $C_2$-$C_6$ alkoxyalkyl, $C_2$-$C_6$ haloalkoxyalkyl, $C_1$-$C_6$ alkoxy, $C_1$-$C_6$ haloalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_3$-$C_6$ cycloalkoxy, $C_3$-$C_6$ halocycloalkoxy, $C_2$-$C_6$ alkylcarbonyloxy, $C_2$-$C_6$ haloalkylcarbonyloxy, $C_2$-$C_6$ alkoxycarbonyloxy, $C_2$-$C_6$ haloalkoxycarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl, $C_1$-$C_6$ alkylamino, $C_1$-$C_6$ haloalkylamino, $C_2$-$C_6$ dialkylamino, $C_2$-$C_6$ alkylcarbonylamino or $C_2$-$C_6$ alkoxycarbonylamino;

$R^2$ is cyano, hydroxy, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ cyanoalkyl, $C_1$-$C_6$ alkoxy, $C_1$-$C_6$ haloalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ cyanoalkoxy, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl; or $C_3$-$C_6$ cycloalkyl or $C_4$-$C_6$ cycloalkylalkyl, each optionally substituted with up to 3 substituents independently selected from halogen, cyano and $C_1$-$C_3$ alkyl;

$R^3$ is amino, cyano, hydroxy, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ cyanoalkyl, $C_1$-$C_6$ alkoxy, $C_1$-$C_6$ haloalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ cyanoalkoxy, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

$R^4$ is cyano;

each $R^5$ is independently amino, cyano, halogen, hydroxy, nitro or -U-V-T; or $C_1$-$C_6$ alkyl, $C_2$-$C_6$ alkenyl, $C_2$-$C_6$ alkynyl, $C_3$-$C_6$ cycloalkyl, $C_4$-$C_6$ cycloalkylalkyl, $C_2$-$C_6$ cyanoalkyl, $C_1$-$C_6$ hydroxyalkyl, $C_1$-$C_6$ alkoxy, $C_2$-$C_6$ alkenyloxy, $C_2$-$C_6$ alkynyloxy, $C_3$-$C_6$ cycloalkoxy, $C_2$-$C_6$ cyanoalkoxy, $C_2$-$C_6$ alkylcarbonyloxy, $C_2$-$C_6$ alkylcarbonyl, $C_2$-$C_6$ alkoxycarbonyl, $C_1$-$C_6$ alkylamino or $C_2$-$C_6$ dialkylamino, each optionally substituted with up to 5 substituents independently selected from halogen and $C_1$-$C_3$ alkyl;

each $R^{6a}$ and $R^{6b}$ is independently H, $C_1$-$C_3$ alkyl, $C_1$-$C_3$ haloalkyl, $C_1$-$C_3$ alkoxy, $C_1$-$C_3$ haloalkoxy, $C_2$-$C_4$ alkylcarbonyl or $C_2$-$C_4$ alkoxycarbonyl;

each U is independently a direct bond, O, C(=O) or $NR^7$;

each V is independently $C_1$-$C_6$ alkylene, $C_2$-$C_6$ alkenylene or $C_3$-$C_6$ alkynylene, wherein up to 2 carbon atoms are C(=O), each optionally substituted with up to 3 substituents independently selected from halogen, cyano, nitro, hydroxy, $C_1$-$C_6$ alkyl, $C_1$-$C_6$ haloalkyl, $C_1$-$C_6$ alkoxy and $C_1$-$C_6$ haloalkoxy;

each T is independently $NR^{8a}R^{8b}$, $OR^9$ or $S(=O)_pR^{10}$;

each p is independently 0, 1 or 2;

each $R^7$ is independently H, $C_1$-$C_6$ alkyl, $C_1$-$C_6$ haloalkyl, $C_2$-$C_6$ alkylcarbonyl, $C_2$-$C_6$ haloalkylcarbonyl, $C_2$-$C_6$ alkoxycarbonyl, $C_2$-$C_6$ (alkylthio)carbonyl or $C_2$-$C_6$ alkoxy(thiocarbonyl);

each $R^{8a}$ and $R^{8b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_2$-$C_6$ alkylcarbonyl or $C_2$-$C_6$ alkoxycarbonyl; or $R^{8a}$ and $R^{8b}$ are taken together with the nitrogen atom to which they are attached to form a 3- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 3 substituents independently selected from $R^{11}$;

each $R^9$ and $R^{10}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl; and each $R^{11}$ is independently halogen, $C_1$-$C_3$ alkyl, $C_1$-$C_3$ haloalkyl, $C_1$-$C_3$ alkoxy or $C_1$-$C_3$ haloalkoxy;

provided that:

(a) when J is J-1, then at most only one of $Q^1$ and $Q^2$ is an optionally substituted phenyl ring;

(b) when J is J-8, then $Q^1$ is a phenyl ring substituted with at least one $R^5$ substituent at an ortho position, and $Q^2$ is an optionally substituted phenyl ring;

(c) the compound of Formula 1 is not:

5-(4-chlorophenyl)-4-(2,4-dichlorophenyl)-2,6-bis(1-methylethoxy)pyrimidine,
5-(4-chlorophenyl)-4-(2,4-dichlorophenyl)-2,6-diethoxypyrimidine,
5-(4-chlorophenyl)-4-(2,4-dichlorophenyl)-2,6-dimethoxypyrimidine,
2,4-dichloro-5-(4-methoxyphenyl)-6-phenylpyrimidine,
2,4-dichloro-5-(4-chlorophenyl)-6-phenylpyrimidine,
2,4-dichloro-6-(4-chlorophenyl)-5-phenylpyrimidine,
2,4-dichloro-6-(4-methylphenyl)-5-phenylpyrimidine,
2,4-dichloro-5,6-diphenylpyrimidine,
4-chloro-6-(4-chlorophenyl)-5-(2,4,6-trifluorophenyl)pyrimidine,
4-chloro-6-(3-fluorophenyl)-5-(2,4,6-trifluorophenyl)pyrimidine,
4-chloro-6-(3,5-dimethoxyphenyl)-5-(2,4,6-trifluorophenyl)pyrimidine,
4-(4-chlorophenyl)-6-methyl-5-(2,4,6-trifluorophenyl)pyrimidine,
4-(3-fluorophenyl)-6-methyl-5-(2,4,6-trifluorophenyl)pyrimidine,
4-(3,5-dimethoxyphenyl)-6-methyl-5-(2,4,6-trifluorophenyl)pyrimidine,
4-(4-chlorophenyl)-5-(2,6-difluoro-4-methoxyphenyl)-6-methylpyrimidine,
5-(2,6-difluoro-4-methoxyphenyl)-4-(3-fluorophenyl)-6-methylpyrimidine and
5-(2,6-difluoro-4-methoxyphenyl)-4-(3,5-dimethoxyphenyl)-6-methylpyrimidine.

More particularly, this invention pertains to a compound of Formula 1 (including all stereoisomers), an N-oxide or a salt thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

This invention also relates to a composition comprising a compound of Formula 1, an N-oxide, or a salt thereof, and at least one invertebrate pest control compound or agent.

DETAILS OF THE INVENTION

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of" Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "agronomic" refers to the production of field crops such as for food and fiber and includes the growth of maize or corn, soybeans and other legumes, rice, cereal (e.g., wheat, oats, barley, rye and rice), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (e.g., berries and cherries) and other specialty crops (e.g., canola, sunflower and olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

The term "crop vigor" refers to rate of growth or biomass accumulation of a crop plant. An "increase in vigor" refers to an increase in growth or biomass accumulation in a crop plant relative to an untreated control crop plant. The term "crop yield" refers to the return on crop material, in terms of both quantity and quality, obtained after harvesting a crop plant. An "increase in crop yield" refers to an increase in crop yield relative to an untreated control crop plant.

The term "biologically effective amount" refers to the amount of a biologically active compound (e.g., a compound of Formula 1 or a mixture with at least one other fungicidal compound) sufficient to produce the desired biological effect when applied to (i.e. contacted with) a fungus to be controlled or its environment, or to a plant, the seed from which the plant is grown, or the locus of the plant (e.g., growth medium) to protect the plant from injury by the fungal disease or for other desired effect (e.g., increasing plant vigor).

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As referred to herein, the term "broadleaf" used either alone or in words such as "broadleaf crop" means dicot or dicotyledon, a term used to describe a group of angiosperms characterized by embryos having two cotyledons.

As referred to in this disclosure, the terms "fungal pathogen" and "fungal plant pathogen" include pathogens in the Ascomycota, Basidiomycota and Zygomycota phyla, and the fungal-like Oomycota class that are the causal agents of a broad spectrum of plant diseases of economic importance, affecting ornamental, turf, vegetable, field, cereal and fruit crops. In the context of this disclosure, "protecting a plant from disease" or "control of a plant disease" includes preventative action (interruption of the fungal cycle of infection, colonization, symptom development and spore production) and/or curative action (inhibition of colonization of plant host tissues).

As used herein, the term "mode of action" (MOA) is as define by the Fungicide Resistance Action Committee (FRAC), and is used to distinguish fungicides according to their biochemical mode of action in the biosynthetic pathways of plant pathogens, and their resistance risk. FRAC-defined modes of actions include (A) nucleic acids metabolism, (B) cytoskeleton and motor protein, (C) respiration, (D) amino acids and protein synthesis, (E) signal transduction, (F) lipid synthesis or transport and membrane integrity or function, (G) sterol biosynthesis in membranes, (H) cell wall biosynthesis, (I) melanin synthesis in cell wall, (P) host plant defense induction, (U) unknown mode of action, (M) chemicals with multi-site activity and (BM) biologicals with multiple modes of action. Each mode of action (i.e. letters A through BM) contain one or more subgroups (e.g., A includes subgroups A1, A2, A3 and A4) based either on individual validated target sites of action, or in cases where the precise target site is unknown, based on cross resistance profiles within a group or in relation to other groups. Each of these subgroups (e.g., A1, A2, A3 and A4) is assigned a FRAC code which is a number and/or letter. For example, the FRAC code for subgroup A1 is 4. Additional information on target sites and FRAC codes can be obtained from publicly available databases maintained, for example, by FRAC.

As used herein, the term "cross resistance" refers to the phenomenon that occurs when a pathogen develops resistance to one fungicide and simultaneously becomes resistant to one or more other fungicides. These other fungicides are typically, but not always, in the same chemical class or have the same target site of action, or can be detoxified by the same mechanism.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating agent" does not limit the carbon-containing radical to alkyl; the carbon-containing radicals in alkylating agents include the variety of carbon-bound substituent radicals specified, for example, for $R^{1a}$ and $R^2$.

Generally, when a molecular fragment (i.e. radical) is denoted by a series of atom symbols (e.g., C, H, N, O and S) the implicit point or points of attachment will be easily recognized by those skilled in the art. In some instances herein, particularly when alternative points of attachment are possible, the point or points of attachment may be explicitly indicated by a hyphen ("-"). The dotted line in rings depicted in the present description (e.g., the ring in Formula 1) represents that the bond indicated can be a single bond or double bond.

In the above recitations, the term "alkyl", used either alone or in compound words such as "alkylthio" or "haloalkyl" includes straight-chain and branched alkyl, such as, methyl, ethyl, n-propyl, i-propyl, and the different butyl, pentyl and hexyl isomers. "Alkenyl" includes straight-chain and branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain and branched alkynes such as ethynyl, 1-propynyl, 2-propynyl, and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$, and the different butylene isomers. "Alkenylene" denotes a straight-chain or branched alkenediyl containing one olefinic bond. Examples of "alkenylene" include $CH{=}CH$, $CH_2CH{=}CH$, $CH{=}C(CH_3)$ and the different butenylene isomers. "Alkynylene" denotes a straight-chain or branched alkynediyl containing one triple bond. Examples of "alkynylene" include $CH_2C{\equiv}C$, $C{\equiv}CCH_2$, and the different butynylene, pentynylene or hexynylene isomers.

"Alkoxy" includes, for example, methoxy, ethoxy, n-propyloxy, i-propyloxy, and the different butoxy isomers. "Alkenyloxy" includes straight-chain and branched alkenyl attached to and linked through an oxygen atom. Examples of "alkenyloxy" include $H_2C{=}CHCH_2O$ and $CH_3CH{=}CHCH_2O$. "Alkynyloxy" includes straight-chain and branched alkynyl attached to and linked through an oxygen atom. Examples of "alkynyloxy" include $HC{\equiv}CCH_2O$ and $CH_3C{\equiv}CCH_2O$.

The term "alkylthio" includes straight-chain and branched alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S({=}O)$, $CH_3CH_2S({=}O)$, $CH_3CH_2CH_2S({=}O)$, $(CH_3)_2CHS({=}O)$, and the different butylsulfinyl isomers. Examples of "alkylsulfonyl" include $CH_3S({=}O)_2$, $CH_3CH_2S({=}O)_2$, $CH_3CH_2CH_2S({=}O)_2$, $(CH_3)_2CHS({=}O)_2$, and the different butylsulfonyl isomers.

"(Alkylthio)carbonyl" denotes a straight-chain or branched alkylthio group bonded to a $C({=}O)$ moiety. Examples of "(alkylthio)carbonyl" include $CH_3SC({=}O)$, $CH_3CH_2CH_2SC({=}O)$ and $(CH_3)_2CHSC({=}O)$. "Alkoxy(thiocarbonyl)" denotes a straight-chain or branched alkoxy group bonded to a $C({=}S)$ moiety. Examples of "alkoxy(thiocarbonyl)" include $CH_3CH_2OC({=}S)$, $CH_3CH_2CH_2OC({=}S)$ and $(CH_3)_2CHCH_2OC({=}S)$.

"Alkylamino" includes an NH radical substituted with a straight-chain or branched alkyl group. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$.

"Alkylcarbonyl" denotes a straight-chain or branched alkyl group bonded to a $C({=}O)$ moiety. Examples of "alkylcarbonyl" include $CH_3C({=}O)$, $CH_3CH_2CH_2C({=}O)$ and $(CH_3)_2CHC({=}O)$. "Alkoxycarbonyl" includes a $C({=}O)$ moiety substituted with a straight-chain or branched alkoxy group. Examples of "alkoxycarbonyl" include $CH_3OC({=}O)$, $CH_3CH_2OC({=}O)$, $CH_3CH_2CH_2OC({=}O)$, $(CH_3)_2CHOC({=}O)$, and the different butoxy- and pentoxycarbonyl isomers.

"Alkylaminocarbonyl" denotes a straight-chain or branched alkyl group bonded to a $NHC({=}O)$ moiety. Examples of "alkylaminocarbonyl" include $CH_3NHC({=}O)$, $CH_3CH_2NHC({=}O)$, $CH_3CH_2CH_2NHC({=}O)$, $(CH_3)_2CHNHC({=}O)$, and the different butylamino- and pentylaminocarbonyl isomers.

"Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$.

The term "alkylcarbonyloxy" denotes a straight-chain or branched alkyl bonded to a $C({=}O)O$ moiety. Examples of "alkylcarbonyloxy" include $CH_3CH_2C({=}O)O$ and $(CH_3)_2CHC({=}O)O$. The term "alkoxycarbonyloxy" denotes a straight-chain or branched alkoxy bonded to a $C({=}O)O$ moiety. Examples of "alkoxycarbonyloxy" include $CH_3CH_2CH_2OC({=}O)O$ and $(CH_3)_2CHOC({=}O)O$.

The term "cycloalkyl" denotes a saturated carbocyclic ring consisting of between 3 to 6 carbon atoms linked to one another by single bonds. Examples of "cycloalkyl" include cyclopropyl, cyclobutyl and cyclopentyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to a straight-chain or branched alkyl group. The term "cycloalkoxy" denotes cycloalkyl attached to and linked through an oxygen atom including, for example, cyclopentyloxy and cyclohexyloxy.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $CF_3$, $ClCH_2$, $CF_3CH_2$ and $CF_3CCl_2$. The terms "haloalkenyl", "haloalkynyl" "haloalkoxy", "haloalkylsulfonyl", "halocycloalkyl", and the like, are defined analogously to the term "haloalkyl". Examples of "haloalkenyl" include $Cl_2C{=}CHCH_2$ and $CF_3CH_2CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $F_2CHCH_2CH_2O$ and $CF_3CH_2O$. Examples of "haloalkylsulfonyl" include $CF_3S({=}O)_2$, $CCl_3S({=}O)_2$, $CF_3CH_2S({=}O)_2$ and $CF_3CF_2S({=}O)_2$. Examples of "halocycloalkyl" include 2-chlorocyclopropyl, 2-fluorocyclobutyl, 3-bromocyclopentyl and 4-chorocyclohexyl.

"Cyanoalkyl" denotes an alkyl group substituted with one cyano group. Examples of "cyanoalkyl" include $NCCH_2$, $NCCH_2CH_2$ and $CH_3CH(CN)CH_2$. "Cyanoalkoxy" denotes an alkyloxy group substituted with one cyano group. Examples of "cyanoalkoxy" include $NCCH_2O$, $NCCH_2CH_2O$ and $CH_3CH(CN)CH_2O$. The term "hydroxyalkyl" denotes an alkyl group substituted with one hydroxy group. Examples of "hydroxyalkyl" include $HOCH_2$, $HOCH_2CH_2$ and $CH_3CH(OH)CH_2$.

The total number of carbon atoms in a substituent group is indicated by the "$C_i$-$C_j$" prefix where i and j are numbers from 1 to 6. For example, $C_1$-$C_3$ alkyl designates methyl through propyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

Generally when a molecular fragment (i.e. radical) is denoted by a series of atom symbols (e.g., C, H, N, O and S) the implicit point or points of attachment will be easily recognized by those skilled in the art. In some instances herein, particularly when alternative points of attachment are possible, the point or points of attachment may be explicitly indicated by a hyphen ("-").

The term "unsubstituted" in connection with a group such as a ring means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3. As used herein, the term "optionally substituted" is used interchangeably with the phrase "substituted or unsubstituted" or with the term "(un)substituted."

The number of optional substituents may be restricted by an expressed limitation. For example, the phrase "optionally substituted with up to 3 substituents independently selected from $R^5$" means that 0, 1, 2 or 3 substituents can be present (if the number of potential connection points allows). When a range specified for the number of substituents (e.g., q being an integer from 0 to 4 in Exhibit A) exceeds the number of positions available for substituents on a ring (e.g., 2 positions available for $(R^5)_q$ on A-7 in Exhibit A), the actual higher end of the range is recognized to be the number of available positions.

When a compound is substituted with a substituent bearing a subscript that indicates the number of said substituents can vary (e.g., $(R^5)_q$ in Exhibit A wherein x is 1 to 4), then said substituents are independently selected from the group of defined substituents, unless otherwise indicated. When a variable group is shown to be optionally attached to a position, for example $(R^5)_q$ in Exhibit A wherein x may be 0, then hydrogen may be at the position even if not recited in the definition of the variable group.

Naming of substituents in the present disclosure uses recognized terminology providing conciseness in precisely conveying to those skilled in the art the chemical structure. For sake of conciseness, locant descriptors may be omitted.

The term "ring member" refers to an atom (e.g., C, O, N or S) or other moiety (e.g., C(=O), C(=S), S(=O) and $S({=}O)_2$) forming the backbone of a ring or ring system. The term "aromatic" indicates that each of the ring atoms is essentially in the same plane and has a p-orbital perpendicular to the ring plane, and that $(4n+2)\pi$ electrons, where n is a positive integer, are associated with the ring to comply with Hückel's rule.

The term "carbocyclic ring" denotes a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

As used herein, the term "partially unsaturated ring" or "partially unsaturated heterocycle" refers to a ring which contains unsaturated ring atoms and one or more double bonds but is not aromatic.

The terms "heterocyclic ring" or "heterocycle" denotes a ring wherein at least one of the atoms forming the ring backbone is other than carbon. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or aromatic heterocyclic ring. "Saturated heterocyclic ring" refers to a heterocyclic ring containing only single bonds between ring members.

Unless otherwise indicated, heterocyclic rings are attached to the remainder of Formula 1 through any available carbon or nitrogen atom by replacement of a hydrogen on said carbon or nitrogen atom.

In the context of the present invention when an instance of $Q^1$ or $Q^2$ comprises a phenyl or 6-membered heterocyclic ring (e.g., pyridinyl), the ortho, meta and para positions of each ring are relative to the connection of the ring to the remainder of Formula 1.

Compounds of this invention can exist as one or more stereoisomers. Stereoisomers are isomers of identical constitution but differing in the arrangement of their atoms in space and include enantiomers, diastereomers, cis- and trans-isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. For a comprehensive discussion of all aspects of stereoisomerism, see Ernest L. Eliel and Samuel H. Wilen, *Stereochemistry of Organic Compounds*, John Wiley & Sons, 1994.

This invention comprises all stereoisomers, conformational isomers and mixtures thereof in all proportions as well as isotopic forms such as deuterated compounds.

One skilled in the art will appreciate that not all nitrogen containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides, and agriculturally suitable salts, and solvates thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

Embodiments of the present invention as described in the Summary of the Invention include those described below. In the following Embodiments, Formula 1 includes stereoisomers, N-oxides, and salts thereof, and reference to "a compound of Formula 1" includes the definitions of substituents specified in the Summary of the Invention unless further defined in the Embodiments.

Embodiment 1. A compound of Formula 1 wherein J is J-1, J-2, J-4, J-6, J-7, J-8 or J-9.

Embodiment 2. A compound of Formula 1 or Embodiment 1 wherein J is J-1, J-2, J-4, J-6, J-8 or J-9.

Embodiment 2a. A compound of Formula 1 or Embodiment 2 wherein J is J-2, J-4, J-6 or J-8.

Embodiment 2b. A compound of Formula 1 or Embodiment 2a wherein J is J-2, J-6 or J-8.

Embodiment 2c. A compound of Formula 1 or Embodiment 2b wherein J is J-2 or J-8.

Embodiment 3. A compound of Formula 1 or Embodiments 1-2 wherein J is J-2, J-4, J-6 or J-9.

Embodiment 4. A compound of Embodiment 3 wherein J is J-2 or J-6.

Embodiment 5. A compound of Formula 1 or Embodiment 1 wherein J is J-1.

Embodiment 6. A compound of Formula 1 or Embodiment 1 wherein J is J-2

Embodiment 7. A compound of Formula 1 or Embodiment 1 wherein J is J-4.

Embodiment 8. A compound of Formula 1 or Embodiment 1 wherein J is J-6.

Embodiment 9. A compound of Formula 1 or Embodiment 1 wherein J is J-7.

Embodiment 10. A compound of Formula 1 or Embodiment 1 wherein J is J-8.

Embodiment 11. A compound of Formula 1 or Embodiment 1 wherein J is J-9.

Embodiment 12. A compound of Formula 1 wherein J is J-3.

Embodiment 12a. A compound of Formula 1 wherein J is J-5.

Embodiment 13. A compound of Formula 1 or any one of Embodiments 1 through 12a wherein each W is O.

Embodiment 14. A compound of Formula 1 or any one of Embodiments 1 through 12 wherein each W is S.

Embodiment 15. A compound of Formula 1 or any one of Embodiments 1 through 14 wherein $Q^1$ and $Q^2$ are each independently selected from A-1 through A-47 as depicted in Exhibit A Exhibit A

A-1

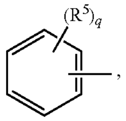

A-2

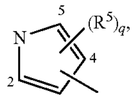

A-3

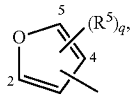

A-4

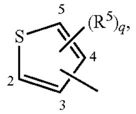

A-5

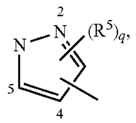

A-6

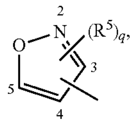

A-7

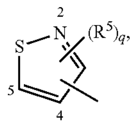

-continued

A-8

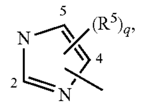

A-9

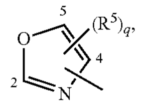

A-10

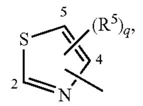

A-11

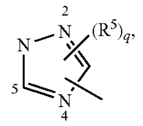

A-12

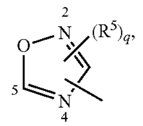

A-13

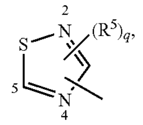

A-14

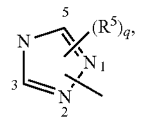

A-15

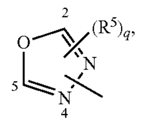

A-16

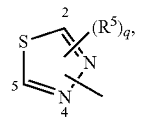

A-17

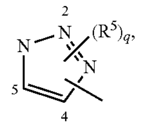

A-18

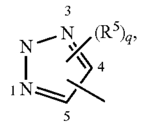

-continued
A-19
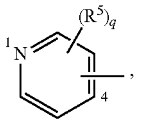
A-20
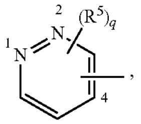
A-21
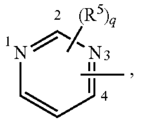
A-22
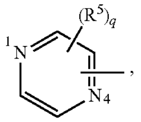
A-23
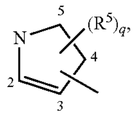
A-24
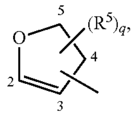
A-25
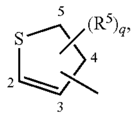
A-26
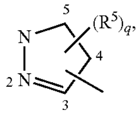
A-27
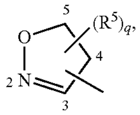
A-28
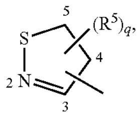
A-29
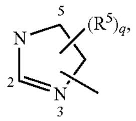
-continued
A-30
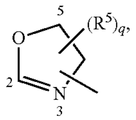
A-31
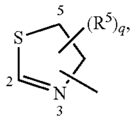
A-32
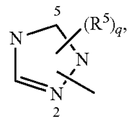
A-33
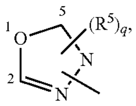
A-34
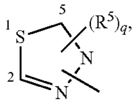
A-35
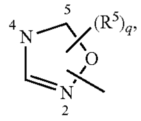
A-36
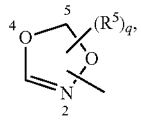
A-37
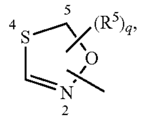
A-38
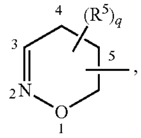
A-39
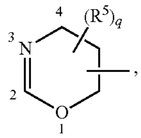
A-40
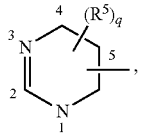

-continued

A-41

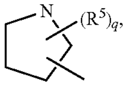

A-42

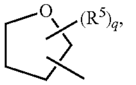

A-43

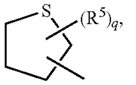

A-44

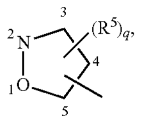

A-45

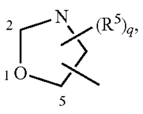

A-46

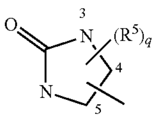

and

A-47

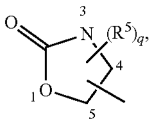

wherein the floating bond is connected to Formula 1 through any available carbon or nitrogen atom of the depicted ring; and each q is independently 0, 1, 2, 3 or 4.

Embodiment 16. A compound of Embodiment 15 wherein $Q^1$ and $Q^2$ are each independently selected from A-1, A-2, A-4, A-10, A-19, A-21, A-23, A-25, A-28, A-31 and A-43.

Embodiment 17. A compound of Embodiment 16 wherein $Q^1$ and $Q^2$ are each independently selected from A-1, A-2, A-4, A-19, A-25, A-28, A-31 and A-43.

Embodiment 18. A compound of Embodiment 17 wherein $Q^1$ and $Q^2$ are each independently selected from A-1, A-4 and A-19.

Embodiment 19. A compound of Embodiment 19 wherein $Q^1$ and $Q^2$ are each independently selected from A-1 and A-4.

Embodiment 20. A compound of Embodiment 19 wherein $Q^2$ is A-4.

Embodiment 21. A compound of Embodiment 19 wherein $Q^1$ and $Q^2$ are each A-1.

Embodiment 22. A compound of Formula 1 or any one of Embodiments 1 through 21 wherein $Q^1$ is selected from A-2, A-4, A-19, A-25, A-28, A-31 and A-43 and $Q^2$ is A-1.

Embodiment 23. A compound of Embodiments 22 wherein $Q^1$ is selected from A-4 and A-19 and $Q^2$ is A-1.

Embodiment 24. A compound of Embodiments 23 wherein $Q^1$ is A-4 and $Q^2$ is A-1.

Embodiment 25. A compound of Embodiments 23 wherein $Q^1$ is A-19 and $Q^2$ is A-1.

Embodiment 26. A compound of Formula 1 or any one of Embodiments 1 through 21 wherein $Q^1$ is A-1 and $Q^2$ is selected from A-2, A-4, A-19, A-25, A-28, A-31 and A-43.

Embodiment 27. A compound of Embodiments 26 wherein $Q^1$ is A-1 and $Q^2$ is selected from A-4 and A-19.

Embodiment 28. A compound of Embodiments 27 wherein $Q^1$ is A-1 and $Q^2$ is A-4.

Embodiment 29. A compound of Embodiments 24 wherein $Q^1$ is A-1 and $Q^2$ is A-19.

Embodiment 30. A compound of Formula 1 or any one of Embodiments 1 through 30 wherein $Q^1$ is substituted with at least 1 substituent selected from $R^5$ attached at an ortho position (relative to the connection of the $Q^1$ ring to the remainder of Formula 1).

Embodiment 31. A compound any one of Embodiments 15 through 30 wherein each q is independently 0, 1, 2 or 3.

Embodiment 32. A compound any one of Embodiment 31 wherein each q is independently 1, 2 or 3.

Embodiment 33. A compound any one of Embodiment 32 wherein each q is independently 2 or 3.

Embodiment 34. A compound of Formula 1 or any one of Embodiments 1 through 33 wherein $R^{1a}$ and $R^{1b}$ are each independently H, halogen, cyano, C(=O)$NR^{6a}R^{6b}$, $C_1$-$C_3$ alkyl, $C_1$-$C_3$ haloalkyl, $C_2$-$C_3$ alkenyl $C_2$-$C_3$ haloalkenyl, $C_2$-$C_3$ alkynyl, $C_2$-$C_3$ haloalkynyl, $C_3$-$C_5$ cycloalkyl, $C_3$-$C_5$ halocycloalkyl, $C_1$-$C_3$ hydroxyalkyl, $C_1$-$C_3$ alkoxy, $C_1$-$C_3$ haloalkoxy, $C_2$-$C_3$ alkenyloxy, $C_2$-$C_3$ haloalkenyloxy, $C_2$-$C_3$ alkynyloxy, $C_2$-$C_3$ haloalkynyloxy, $C_3$-$C_5$ cycloalkoxy, $C_1$-$C_3$ alkylamino or $C_2$-$C_3$ dialkylamino.

Embodiment 34a. A compound of Embodiment 34 wherein $R^{1a}$ and $R^{1b}$ are each independently H, halogen, cyano, C(=O)$NR^{6a}R^{6b}$, $C_1$-$C_3$ alkyl, $C_1$-$C_3$ haloalkyl, $C_2$-$C_3$ alkenyl $C_2$-$C_3$ haloalkenyl, $C_2$-$C_3$ alkynyl, $C_2$-$C_3$ haloalkynyl, $C_3$-$C_5$ cycloalkyl, $C_3$-$C_5$ halocycloalkyl, $C_1$-$C_3$ alkoxy, $C_1$-$C_3$ haloalkoxy, $C_2$-$C_3$ alkenyloxy, $C_2$-$C_3$ haloalkenyloxy, $C_2$-$C_3$ alkynyloxy, $C_2$-$C_3$ haloalkynyloxy, $C_3$-$C_5$ cycloalkoxy, $C_1$-$C_3$ alkylamino or $C_2$-$C_3$ dialkylamino.

Embodiment 35. A compound of Embodiment 34a wherein $R^{1a}$ and $R^{1b}$ are each independently H, halogen, cyano, $C_1$-$C_3$ alkyl, $C_1$-$C_3$ haloalkyl, cyclopropyl, halocyclopropyl, $C_1$-$C_3$ alkoxy, $C_1$-$C_3$ haloalkoxy, $C_2$-$C_3$ alkenyloxy or $C_2$-$C_3$ haloalkenyloxy.

Embodiment 36. A compound of Embodiment 34 wherein $R^{1a}$ and $R^{1b}$ are each independently H, halogen, cyano, $C_1$-$C_3$ alkyl, $C_1$-$C_3$ haloalkyl, cyclopropyl, $C_1$-$C_3$ hydroxyalkyl, $C_1$-$C_3$ alkoxy or $C_1$-$C_3$ haloalkoxy.

Embodiment 36a. A compound of Embodiment 36 wherein $R^{1a}$ and $R^{1b}$ are each independently H, halogen, cyano, $C_1$-$C_3$ alkyl, $C_1$-$C_3$ haloalkyl, cyclopropyl, $C_1$-$C_2$ $C_1$-$C_3$ alkoxy or $C_1$-$C_3$ haloalkoxy.

Embodiment 37. A compound of Embodiment 36a wherein $R^{1a}$ and $R^{1b}$ are each independently H, halogen, cyano, $C_1$-$C_2$ alkyl, $C_1$-$C_2$ haloalkyl, cyclopropyl, $C_1$-$C_2$ alkoxy or $C_1$-$C_2$ haloalkoxy.

Embodiment 38. A compound of Embodiment 36 wherein $R^{1a}$ and $R^{1b}$ are each independently H, halogen, cyano, $C_1$-$C_2$ alkyl, $C_1$-$C_2$ haloalkyl, cyclopropyl or $C_1$-$C_2$ hydroxyalkyl.

Embodiment 38a. A compound of Embodiment 38 wherein $R^{1a}$ and $R^{1b}$ are each independently H, halogen, cyano, $C_1$-$C_2$ alkyl, $C_1$-$C_2$ haloalkyl or cyclopropyl.

Embodiment 39. A compound of Embodiment 38a wherein $R^{1a}$ and $R^{1b}$ are each independently is H, halogen, cyano, methyl, ethyl, halomethyl or cyclopropyl.

Embodiment 39a. A compound of Embodiment 39 wherein $R^{1a}$ and $R^{1b}$ are each independently is H, halogen, methyl, ethyl or halomethyl.

Embodiment 39b. A compound of Embodiment 39a wherein $R^{1a}$ and $R^{1b}$ are each independently is H, Cl, methyl, ethyl or halomethyl.

Embodiment 39c. A compound of Embodiment 39b wherein $R^{1a}$ and $R^{1b}$ are each independently is H, Cl, methyl or ethyl.

Embodiment 39d. A compound of Embodiment 39c wherein $R^{1a}$ and $R^{1b}$ are each independently is Cl, methyl or ethyl.

Embodiment 40. A compound of Embodiment 39 wherein $R^{1a}$ and $R^{1b}$ are each independently H, halogen, cyano, methyl, ethyl or cyclopropyl.

Embodiment 41. A compound of Embodiment 38 wherein $R^{1a}$ and $R^{1b}$ are each independently H, Br, Cl, F, cyano, methyl, ethyl, $CH_2OH$ or $CH_2F$.

Embodiment 41a. A compound of Embodiment 41 wherein $R^{1a}$ and $R^{1b}$ are each independently H, Br, Cl, F, cyano, methyl, ethyl or $CH_2OH$.

Embodiment 41b. A compound of Embodiment 41 wherein $R^{1a}$ and $R^{1b}$ are each independently H, Br, Cl, F, cyano, methyl, ethyl or $CH_2F$.

Embodiment 41c. A compound of Embodiment 41b wherein $R^{1a}$ and $R^{1b}$ are each independently H, Br, Cl, F, cyano, methyl or ethyl.

Embodiment 42. A compound of Embodiment 41b wherein $R^{1a}$ and $R^{1b}$ are each independently H, Br, Cl, F, methyl or ethyl.

Embodiment 42a. A compound of Embodiment 42 wherein $R^{1a}$ and $R^{1b}$ are each independently H, Br, Cl, methyl or ethyl.

Embodiment 42b. A compound of Embodiment 42 wherein $R^{1a}$ and $R^{1b}$ are each independently Br, Cl, F, methyl or ethyl.

Embodiment 42b. A compound of Embodiment 42a wherein $R^{1a}$ and $R^{1b}$ are each independently Br, Cl, methyl or ethyl.

Embodiment 43. A compound of Embodiment 42 wherein $R^{1a}$ and $R^{1b}$ are each independently H, Br, Cl or methyl.

Embodiment 44. A compound of Embodiment 44 wherein $R^{1a}$ and $R^{1b}$ are each independently H, Cl or methyl.

Embodiment 44a. A compound of Embodiment 42 wherein $R^{1a}$ and $R^{1b}$ are each independently H, Cl, methyl or ethyl.

Embodiment 44b. A compound of Embodiment 44a wherein $R^{1a}$ and $R^{1b}$ are each independently Cl, methyl or ethyl.

Embodiment 45. A compound of Embodiment 44b wherein $R^{1a}$ and $R^{1b}$ are each Cl.

Embodiment 46. A compound of Embodiment 44b wherein $R^{1a}$ and $R^{1b}$ are each methyl.

Embodiment 47. A compound of Formula 1 or any one of Embodiments 1 through 46 wherein $R^2$ is $C_1$-$C_3$ alkyl, $C_1$-$C_3$ haloalkyl, $C_2$-$C_3$ alkenyl, $C_2$-$C_3$ haloalkenyl, $C_2$-$C_3$ cyanoalkyl, $C_1$-$C_3$ alkoxy or $C_1$-$C_3$ haloalkoxy; or $C_3$-$C_5$ cycloalkyl, optionally substituted with up to 3 substituents independently selected from halogen and methyl.

Embodiment 48. A compound of Embodiment 47 wherein $R^2$ is $C_1$-$C_3$ alkyl, $C_1$-$C_3$ haloalkyl, $C_1$-$C_3$ alkoxy or $C_1$-$C_3$ haloalkoxy; or cyclopropyl, optionally substituted with up to 2 substituents independently selected from halogen and methyl.

Embodiment 49. A compound of Embodiment 48 wherein $R^2$ is $C_1$-$C_2$ alkyl, $C_1$-$C_2$ haloalkyl, $C_1$-$C_2$ alkoxy or $C_1$-$C_2$ haloalkoxy.

Embodiment 50. A compound of Embodiment 49 wherein $R^2$ is methyl, ethyl or methoxy.

Embodiment 51. A compound of Embodiment 50 wherein $R^2$ is methyl or ethyl.

Embodiment 52. A compound of Embodiment 51 wherein $R^2$ is methyl.

Embodiment 53. A compound of Embodiment 51 wherein $R^2$ is ethyl.

Embodiment 54. A compound of Formula 1 or any one of Embodiments 1 through 53 wherein $R^3$ is cyano, hydroxy, $C_1$-$C_6$ alkyl, $C_1$-$C_6$ haloalkyl, $C_2$-$C_6$ cyanoalkyl, $C_1$-$C_6$ alkoxy, $C_1$-$C_6$ haloalkoxy, $C_2$-$C_6$ alkenyloxy, $C_2$-$C_6$ haloalkenyloxy or $C_2$-$C_6$ cyanoalkoxy.

Embodiment 55. A compound of Embodiment 54 wherein $R^3$ is cyano, hydroxy, $C_1$-$C_6$ alkyl, $C_1$-$C_6$ haloalkyl, $C_1$-$C_6$ alkoxy, $C_1$-$C_6$ haloalkoxy or $C_2$-$C_6$ cyanoalkoxy.

Embodiment 56. A compound of Embodiment 55 wherein $R^3$ is hydroxy, $C_1$-$C_3$ alkyl, $C_1$-$C_3$ haloalkyl, $C_1$-$C_3$ alkoxy or $C_2$-$C_3$ cyanoalkoxy.

Embodiment 57. A compound of Embodiment 56 wherein $R^3$ is $C_1$-$C_3$ alkyl, $C_1$-$C_3$ haloalkyl or $C_1$-$C_3$ alkoxy.

Embodiment 58. A compound of Embodiment 57 wherein $R^3$ is $C_1$-$C_2$ alkyl or $C_1$-$C_2$ haloalkyl.

Embodiment 59. A compound of Embodiment 58 wherein $R^3$ is methyl or ethyl.

Embodiment 60. A compound of Embodiment 59 wherein $R^3$ is methyl.

Embodiment 61. A compound of Embodiment 59 wherein $R^3$ is ethyl.

Embodiment 62. A compound of Formula 1 or any one of Embodiments 1 through 61 wherein each $R^5$ is independently cyano, halogen, nitro or -U-V-T; or $C_1$-$C_6$ alkyl, $C_2$-$C_6$ alkenyl, $C_2$-$C_6$ alkynyl, $C_3$-$C_6$ cycloalkyl, $C_2$-$C_6$ cyanoalkyl, $C_1$-$C_6$ alkoxy, $C_2$-$C_6$ alkenyloxy, $C_2$-$C_6$ alkynyloxy, $C_3$-$C_6$ cycloalkoxy, $C_2$-$C_6$ cyanoalkoxy, $C_2$-$C_6$ alkylcarbonyl or $C_2$-$C_6$ alkoxycarbonyl, each optionally substituted with up to 3 substituents independently selected from halogen.

Embodiment 63. A compound of Embodiment 62 wherein each $R^5$ is independently cyano, halogen, nitro or -U-V-T; or $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_2$-$C_3$ alkynyloxy, $C_3$-$C_6$ cycloalkoxy or $C_2$-$C_3$ cyanoalkoxy, each optionally substituted with up to 3 substituents independently selected from halogen.

Embodiment 64. A compound Embodiment 63 wherein each $R^5$ is independently cyano, halogen, nitro, $C_1$-$C_2$ alkyl, $C_2$-$C_3$ alkenyl, $C_1$-$C_2$ alkoxy, $C_2$-$C_3$ alkenyloxy or $C_2$-$C_3$ cyanoalkoxy, each optionally substituted with up to 3 substituents independently selected from halogen.

Embodiment 65. A compound Embodiment 64 wherein each $R^5$ is independently cyano, halogen, nitro, $C_1$-$C_2$ alkyl, $C_1$-$C_2$ alkoxy, $C_2$-$C_3$ alkenyloxy or $C_2$-$C_3$ cyanoalkoxy, each optionally substituted with up to 3 substituents independently selected from halogen.

Embodiment 66. A compound Embodiment 65 wherein each $R^5$ is independently cyano, halogen, nitro, $C_1$-$C_2$ alkyl, $C_1$-$C_2$ alkoxy or $C_2$-$C_3$ cyanoalkoxy.

Embodiment 67. A compound Embodiment 66 wherein each $R^5$ is independently cyano, Br, Cl, F, nitro, $C_1$-$C_2$ alkyl, $C_1$-$C_2$ alkoxy or $C_2$-$C_3$ cyanoalkoxy.

Embodiment 68. A compound Embodiment 67 wherein each $R^5$ is independently cyano, Br, Cl, F, nitro, methyl or methoxy.

Embodiment 69. A compound Embodiment 68 wherein each $R^5$ is independently cyano, Br, Cl, F, methyl or methoxy.

Embodiment 70. A compound Embodiment 69 wherein each $R^5$ is independently Br, Cl, F, methyl or methoxy.

Embodiment 71. A compound Embodiment 70 wherein each $R^5$ is independently Br, Cl, F or methoxy.

Embodiment 72. A compound Embodiment 71 wherein each $R^5$ is independently F or methoxy.

Embodiment 73. A compound of Formula 1 or any one of Embodiments 1 through 72 wherein each $R^{6a}$ and $R^{6b}$ is independently H, $C_1$-$C_2$ alkyl, $C_1$-$C_2$ haloalkyl, $C_1$-$C_2$ alkoxy or $C_2$-$C_4$ alkylcarbonyl.

Embodiment 74. A compound of Embodiment 73 wherein each $R^{6a}$ and $R^{6b}$ is independently H, methyl, trifluoromethyl, methoxy or methylcarbonyl.

Embodiment 75. A compound of Embodiment 74 wherein each $R^{6a}$ and $R^{6b}$ is independently H, methyl or methoxy.

Embodiment 76. A compound of Formula 1 or any one of Embodiments 1 through 75 wherein each U is independently a direct bond, O, C(═O) or NH.

Embodiment 77. A compound of Embodiment 76 wherein each U is independently a direct bond, O or NH.

Embodiment 78. A compound of Embodiment 77 wherein each U is independently a direct bond or O.

Embodiment 79. A compound of Embodiment 78 wherein each U is a direct bond.

Embodiment 80. A compound of Embodiment 78 wherein each U is O.

Embodiment 81. A compound of Formula 1 or any one of Embodiments 1 through 80 wherein each V is independently $C_1$-$C_3$ alkylene, wherein up to 2 carbon atoms are C(═O), each optionally substituted with up to 3 substituents independently selected from halogen, $C_1$-$C_2$ alkyl, $C_1$-$C_2$ haloalkyl, $C_1$-$C_2$ alkoxy and $C_1$-$C_2$ haloalkoxy.

Embodiment 82. A compound of Embodiment 81 wherein each V is independently $C_1$-$C_3$ alkylene, wherein up to 1 carbon atom is C(═O), each optionally substituted with up to 2 substituents independently selected from halogen, methyl, halomethyl and methoxy.

Embodiment 83. A compound of Embodiment 82 wherein each V is independently $CH_2$, $CH_2CH_2$, C(═O), $CH_2C$(═O) or C(═O)$CH_2$.

Embodiment 84. A compound of Embodiment 83 wherein each V is $CH_2$.

Embodiment 85. A compound of Formula 1 or any one of Embodiments 1 through 84 wherein each T is independently $NR^{8a}R^{8b}$ or $OR^9$.

Embodiment 86. A compound of Embodiment 85 wherein each T is independently $NR^{8a}R^{8b}$.

Embodiment 87. A compound of Embodiment 85 wherein each T is independently $OR^{10}$.

Embodiment 88. A compound of Formula 1 or any one of Embodiments 1 through 84 wherein each p is 0 or 2.

Embodiment 89. A compound of Formula 1 or any one of Embodiments 1 through 88 wherein when $R^{8a}$ and $R^{8b}$ are separate (i.e. not taken together to form a ring), then each $R^{8a}$ and $R^{8b}$ is independently H, $C_1$-$C_3$ alkyl, $C_1$-$C_3$ haloalkyl, cyclopropyl, $C_2$-$C_3$ alkylcarbonyl or $C_2$-$C_3$ alkoxycarbonyl.

Embodiment 90. A compound of Embodiment 89 wherein each $R^{8a}$ and $R^{8b}$ is independently H, $C_1$-$C_2$ alkyl, $C_1$-$C_2$ haloalkyl or cyclopropyl.

Embodiment 91. A compound of Embodiment 90 wherein each $R^{8a}$ and $R^{8b}$ is independently H, methyl or halomethyl.

Embodiment 92. A compound of Formula 1 or any one of Embodiments 1 through 91 wherein each $R^9$ and $R^{10}$ is independently H, $C_1$-$C_3$ alkyl, $C_1$-$C_3$ haloalkyl, $C_2$-$C_3$ alkenyl, $C_2$-$C_3$ haloalkenyl or cyclopropyl.

Embodiment 93. A compound of Embodiment 92 wherein each $R^9$ and $R^{10}$ is independently H, $C_1$-$C_2$ alkyl or $C_1$-$C_2$ haloalkyl.

Embodiment 94. A compound of Embodiment 93 wherein each $R^9$ and $R^{10}$ is independently methyl or ethyl.

Embodiment 95. A compound of Formula 1 or any one of Embodiments 1 through 94 wherein each $R^{11}$ is independently halogen, methyl, halomethyl or methoxy.

Embodiment 96. A compound of Formula 1 or any one of Embodiments 1 through 95 wherein $Q^1$ is A-1 substituted at the 2- and 4-positions with substituents independently selected from $R^5$; or $Q^1$ is A-1 substituted at the 2- and 6-positions with substituents independently selected from $R^5$; or $Q^1$ is A-1 substituted at the 2-, 4- and 6-positions with substituents independently selected from $R^5$ (all relative to the connection of the $Q^1$ ring to the remainder of Formula 1).

Embodiment 97. A compound of Embodiment 96 wherein $Q^1$ is A-1 substituted at the 2- and 4-positions with substituents independently selected from $R^5$; or $Q^1$ is A-1 substituted at the 2- and 6-positions with substituents independently selected from $R^5$.

Embodiment 98. A compound of Embodiment 97 wherein $Q^1$ is A-1 substituted at the 2- and 4-positions with substituents independently selected from $R^5$.

Embodiment 99. A compound of Embodiment 97 wherein $Q^1$ is A-1 substituted at the 2- and 6-positions with substituents independently selected from $R^5$.

Embodiment 100. A compound of Formula 1 or any one of Embodiments 1 through 99 wherein $Q^1$ is A-1 substituted with at least one $R^5$ substituent attached at an ortho position (2-position) (relative to the connection of the $Q^1$ ring to the remainder of Formula 1).

Embodiment 101. A compound of Formula 1 or any one of Embodiments 1 through 100 wherein $Q^2$ is A-1 substituted at the 2-, 3- and 5-positions with substituents independently selected from $R^5$; or $Q^2$ is A-1 substituted at the 2- and 5-positions with substituents independently selected from $R^5$; $Q^2$ is A-1 substituted at the 3- and 5-positions with substituents independently selected from $R^5$ (all relative to the connection of the $Q^2$ ring to the remainder of Formula 1).

Embodiment 102. A compound of Embodiment 101 wherein $Q^2$ is A-1 substituted at the 2-, 3- and 5-positions with substituents independently selected from $R^5$; or $Q^2$ is A-1 substituted at the 3- and 5-positions with substituents independently selected from $R^5$.

Embodiment 103. A compound of Formula 1 or any one of Embodiments 1 through 102 wherein $Q^2$ is A-1 substituted with at least one $R^5$ substituent attached at an ortho position (2-position); or $Q^2$ is A-1 substituted with at least one $R^5$ substituent at a meta position (3-position) (all relative to the connection of the $Q^2$ ring to the remainder of Formula 1).

Embodiment 104. A compound of Embodiment 103 wherein $Q^2$ is A-1 substituted with at least one $R^5$ substituent at an ortho position (2-position).

Embodiment 105 A compound of Embodiment 103 wherein $Q^2$ is A-1 substituted with at least one $R^5$ substituent at a meta position (3-position).

Embodiments of this invention, including Embodiments 1-105 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-105 above as well as any other embodiments described herein, and any combination thereof, pertain to the compositions and methods of the present invention.

Combinations of Embodiments 1-105 are illustrated by:

Embodiment A. A compound of Formula 1 wherein

J is J-1, J-2, J-4, J-6, J-7, J-8 or J-9;

W is O;

$Q^1$ and $Q^2$ are each independently selected from:

A-1

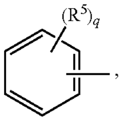

A-2

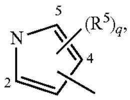

A-3

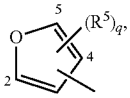

A-4

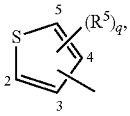

A-5

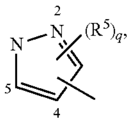

A-6

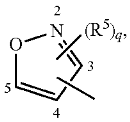

A-7

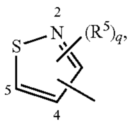

-continued

A-8

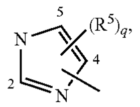

A-9

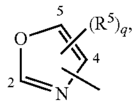

A-10

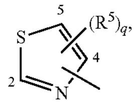

A-11

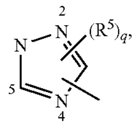

A-12

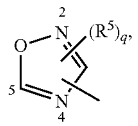

A-13

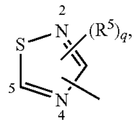

A-14

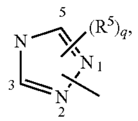

A-15

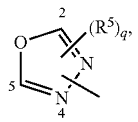

A-16

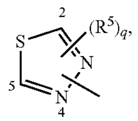

A-17

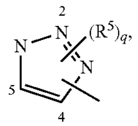

A-18

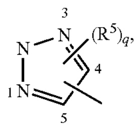

-continued
A-19
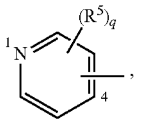
A-20
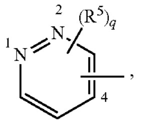
A-21
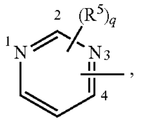
A-22
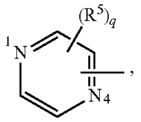
A-23
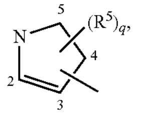
A-24
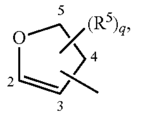
A-25
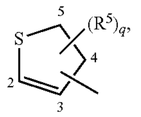
A-26
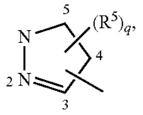
A-27
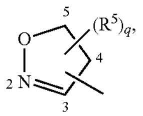
A-28
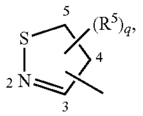
A-29
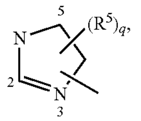
-continued
A-30
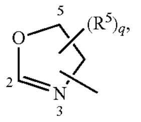
A-31
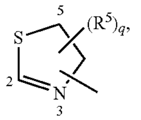
A-32
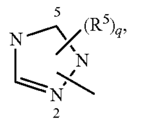
A-33
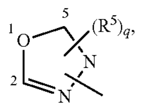
A-34
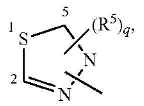
A-35
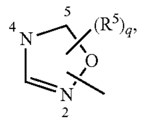
A-36
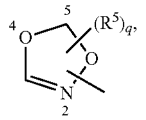
A-37
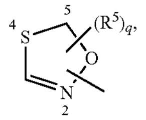
A-38
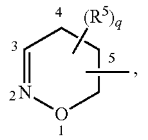
A-39
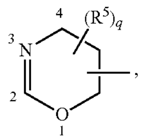
A-40
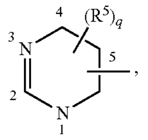

-continued

A-41

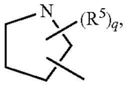

A-42

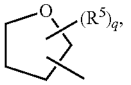

A-43

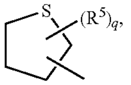

A-44

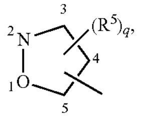

A-45

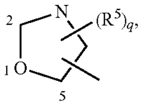

A-46

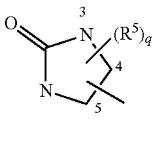

and

A-47

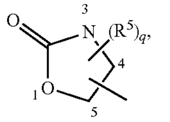

wherein the floating bond is connected to Formula 1 through any available carbon or nitrogen atom of the depicted ring;

each q is independently 0, 1, 2, 3 or 4;

$R^{1a}$ and $R^{1b}$ are each independently H, halogen, cyano, C(═O)NR$^{6a}$R$^{6b}$, $C_1$-$C_3$ alkyl, $C_1$-$C_3$ haloalkyl, $C_2$-$C_3$ alkenyl $C_2$-$C_3$ haloalkenyl, $C_2$-$C_3$ alkynyl, $C_2$-$C_3$ haloalkynyl, $C_3$-$C_5$ cycloalkyl, $C_3$-$C_5$ halocycloalkyl, $C_1$-$C_3$ hydroxyalkyl, $C_1$-$C_3$ alkoxy, $C_1$-$C_3$ haloalkoxy, $C_2$-$C_3$ alkenyloxy, $C_2$-$C_3$ haloalkenyloxy, $C_2$-$C_3$ alkynyloxy, $C_2$-$C_3$ haloalkynyloxy, $C_3$-$C_5$ cycloalkoxy, $C_1$-$C_3$ alkylamino or $C_2$-$C_3$ dialkylamino;

$R^2$ is $C_1$-$C_3$ alkyl, $C_1$-$C_3$ haloalkyl, $C_2$-$C_3$ alkenyl, $C_2$-$C_3$ haloalkenyl, $C_2$-$C_3$ cyanoalkyl, $C_1$-$C_3$ alkoxy or $C_1$-$C_3$ haloalkoxy; or $C_3$-$C_5$ cycloalkyl, optionally substituted with up to 3 substituents independently selected from halogen and methyl;

$R^3$ is cyano, hydroxy, $C_1$-$C_6$ alkyl, $C_1$-$C_6$ haloalkyl, $C_2$-$C_6$ cyanoalkyl, $C_1$-$C_6$ alkoxy, $C_1$-$C_6$ haloalkoxy, $C_2$-$C_6$ alkenyloxy, $C_2$-$C_6$ haloalkenyloxy or $C_2$-$C_6$ cyanoalkoxy;

each $R^5$ is independently cyano, halogen, nitro or -U-V-T; or $C_1$-$C_6$ alkyl, $C_2$-$C_6$ alkenyl, $C_2$-$C_6$ alkynyl, $C_3$-$C_6$ cycloalkyl, $C_2$-$C_6$ cyanoalkyl, $C_1$-$C_6$ alkoxy, $C_2$-$C_6$ alkenyloxy, $C_2$-$C_6$ alkynyloxy, $C_3$-$C_6$ cycloalkoxy, $C_2$-$C_6$ cyanoalkoxy, $C_2$-$C_6$ alkylcarbonyl or $C_2$-$C_6$ alkoxycarbonyl, each optionally substituted with up to 3 substituents independently selected from halogen;

each $R^{6a}$ and $R^{6b}$ is independently H, methyl, trifluoromethyl, methoxy or methylcarbonyl;

each U is independently a direct bond, O, C(═O) or NH;

each V is independently $C_1$-$C_3$ alkylene, wherein up to 1 carbon atom is C(═O), each optionally substituted with up to 2 substituents independently selected from halogen, methyl, halomethyl and methoxy;

each T is independently NR$^{8a}$R$^{8b}$ or OR$^9$;

each $R^{8a}$ and $R^{8b}$ is independently H, $C_1$-$C_3$ alkyl, $C_1$-$C_3$ haloalkyl, cyclopropyl, $C_2$-$C_3$ alkylcarbonyl or $C_2$-$C_3$ alkoxycarbonyl; and each $R^9$ is independently H, $C_1$-$C_3$ alkyl, $C_1$-$C_3$ haloalkyl, $C_2$-$C_3$ alkenyl, $C_2$-$C_3$ haloalkenyl or cyclopropyl.

Embodiment B. A compound of Embodiment A wherein

J is J-1, J-2, J-4, J-6, J-8 or J-9;

$Q^1$ and $Q^2$ are each independently selected from A-1, A-2, A-4, A-19, A-25, A-28, A-31 and A-43;

each q is independently 1, 2 or 3;

$R^{1a}$ and $R^{1b}$ are each independently H, halogen, cyano, $C_1$-$C_3$ alkyl, $C_1$-$C_3$ haloalkyl, cyclopropyl, $C_1$-$C_3$ hydroxyalkyl, $C_1$-$C_3$ alkoxy or $C_1$-$C_3$ haloalkoxy;

$R^2$ is $C_1$-$C_3$ alkyl, $C_1$-$C_3$ haloalkyl, $C_1$-$C_3$ alkoxy or $C_1$-$C_3$ haloalkoxy; or cyclopropyl, optionally substituted with up to 2 substituents independently selected from halogen and methyl;

$R^3$ is cyano, hydroxy, $C_1$-$C_6$ alkyl, $C_1$-$C_6$ haloalkyl, $C_1$-$C_6$ alkoxy, $C_1$-$C_6$ haloalkoxy or $C_2$-$C_6$ cyanoalkoxy;

each $R^5$ is independently cyano, halogen, nitro or -U-V-T; or $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_2$-$C_3$ alkynyloxy, $C_3$-$C_6$ cycloalkoxy or $C_2$-$C_3$ cyanoalkoxy, each optionally substituted with up to 3 substituents independently selected from halogen;

each U is independently a direct bond, O or NH;

each V is independently $CH_2$, $CH_2CH_2$, C(═O), $CH_2$C(═O) or C(═O)$CH_2$;

each $R^{8a}$ and $R^{8b}$ is independently H, $C_1$-$C_2$ alkyl, $C_1$-$C_2$ haloalkyl or cyclopropyl; and each $R^9$ is independently methyl or ethyl.

Embodiment C. A compound of Embodiment B wherein $Q^1$ and $Q^2$ are each independently selected from A-1, A-4 and A-19;

$R^{1a}$ and $R^{1b}$ are each independently H, halogen, cyano, $C_1$-$C_2$ alkyl, $C_1$-$C_2$ haloalkyl, cyclopropyl or $C_1$-$C_2$ hydroxyalkyl;

$R^2$ is $C_1$-$C_2$ alkyl, $C_1$-$C_2$ haloalkyl, $C_1$-$C_2$ alkoxy or $C_1$-$C_2$ haloalkoxy;

$R^3$ is $C_1$-$C_3$ alkyl, $C_1$-$C_3$ haloalkyl or $C_1$-$C_3$ alkoxy; and each $R^5$ is independently cyano, halogen, nitro, $C_1$-$C_2$ alkyl, $C_1$-$C_2$ alkoxy, $C_2$-$C_3$ alkenyloxy or $C_2$-$C_3$ cyanoalkoxy, each optionally substituted with up to 3 substituents independently selected from halogen.

Embodiment D. A compound of Embodiment C wherein

J is J-2, J-4, J-6 or J-8;

$Q^1$ and $Q^2$ are each A-1;

each q is independently 2 or 3;

$R^{1a}$ and $R^{1b}$ are each independently H, Br, Cl, F, cyano, methyl, ethyl or $CH_2F$;

$R^2$ is methyl, ethyl or methoxy;

$R^3$ is methyl or ethyl; and each $R^5$ is independently cyano, halogen, nitro, $C_1$-$C_2$ alkyl, $C_1$-$C_2$ alkoxy or $C_2$-$C_3$ cyanoalkoxy.

Embodiment D1. A compound of Embodiment D wherein J is J-2 or J-6.

Embodiment E. A compound of Embodiment D wherein $R^{1a}$ and $R^{1b}$ are each independently Br, Cl, F, methyl or ethyl;

$R^2$ is methyl or ethyl; and each $R^5$ is independently cyano, Br, Cl, F, methyl or methoxy.

Embodiment F. A compound of Embodiment E wherein $R^{1a}$ and $R^{1b}$ are each independently Br, Cl, methyl or ethyl;

$R^2$ is methyl; and each $R^5$ is independently Br, Cl, F, methyl or methoxy.

Embodiment G. A compound of Embodiment F wherein

J is J-2, J-6 or J-8;

$R^{1a}$ and $R^{1b}$ are each independently Br, Cl or methyl;

each $R^5$ is independently Br, Cl, F or methoxy.

Embodiment H. A compound of any one of Embodiments A through G wherein $Q^1$ is A-1 substituted at the 2- and 4-positions with substituents independently selected from $R^5$; or $Q^i$ is A-1 substituted at the 2- and 6-positions with substituents independently selected from $R^5$; or $Q^i$ is A-1 substituted at the 2-, 4- and 6-positions with substituents independently selected from $R^5$;

$Q^2$ is A-1 substituted at the 2-, 3- and 5-positions with substituents independently selected from $R^5$; or $Q^2$ is A-1 substituted at the 3- and 5-positions with substituents independently selected from $R^5$; and $R^{1a}$ and $R^{1b}$ are each methyl.

Embodiment I. A compound of Formula 1 wherein

J is J-1;

W is Q;

$Q^1$ is A-1;

$Q^2$ is A-4 or A-19;

each q is independently 1, 2 or 3;

$R^{1a}$ is H, Br, Cl, F, cyano, methyl or ethyl;

$R^2$ is methyl, ethyl or methoxy; and each $R^5$ is independently cyano, halogen, nitro, $C_1$-$C_2$ alkyl, $C_1$-$C_2$ alkoxy or $C_2$-$C_3$ cyanoalkoxy.

Embodiment J. A compound of Formula 1 wherein

J is J-8;

W is Q;

$Q^1$ is A-1 substituted with at least one $R^5$ substituent attached at an ortho position;

each q is independently 1, 2 or 3;

$R^3$ is $C_1$-$C_3$ alkyl, $C_1$-$C_3$ haloalkyl or $C_1$-$C_3$ alkoxy; and each $R^5$ is independently cyano, halogen, nitro, $C_1$-$C_2$ alkyl, $C_1$-$C_2$ alkoxy or $C_2$-$C_3$ cyanoalkoxy.

Embodiment K. A compound of Formula 1 wherein

J is J-2;

$Q^1$ and $Q^2$ are each A-1;

each q is independently 2 or 3;

$R^{1a}$ and $R^{1b}$ are each independently H, halogen, cyano, amino, methyl, ethyl, $C_1$ haloalkyl, $C_2$-$C_5$ alkylcarbonylamino or $C_2$-$C_5$ alkoxycarbonylamino; and each $R^5$ is independently cyano, halogen, nitro, $C_1$-$C_2$ alkyl, $C_1$-$C_2$ alkoxy or $C_2$-$C_3$ cyanoalkoxy.

Embodiment L. A compound of Embodiment K wherein $R^{1a}$ and $R^{1b}$ are each independently halogen, cyano, amino, methyl, $C_1$ haloalkyl, $C_2$-$C_3$ alkylcarbonylamino or $C_2$-$C_3$ alkoxycarbonylamino; and each $R^5$ is independently cyano, Br, Cl, F, methyl or methoxy.

Embodiment M. A compound of Embodiment L wherein $R^{1a}$ and $R^{1b}$ are each independently halogen, cyano, amino, methyl or $CH_2F$; and each $R^5$ is independently Br, Cl, F, methyl or methoxy.

Embodiment AA. A compound of Formula 1 wherein $R^{1a}$ and $R^{1b}$ are each independently H, halogen, cyano, hydroxy, nitro, C(=O)$NR^{6a}R^{6b}$, C(=O)OH, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_2$-$C_6$ cyanoalkyl, $C_1$-$C_6$ hydroxyalkyl, $C_2$-$C_6$ alkoxyalkyl, $C_2$-$C_6$ haloalkoxyalkyl, $C_1$-$C_6$ alkoxy, $C_1$-$C_6$ haloalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_3$-$C_6$ cycloalkoxy, $C_3$-$C_6$ halocycloalkoxy, $C_2$-$C_6$ alkylcarbonyloxy, $C_2$-$C_6$ haloalkylcarbonyloxy, $C_2$-$C_6$ alkoxycarbonyloxy, $C_2$-$C_6$ haloalkoxycarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl, $C_1$-$C_6$ alkylamino, $C_1$-$C_6$ haloalkylamino or $C_2$-$C_6$ dialkylamino; and $R^3$ is cyano, hydroxy, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ cyanoalkyl, $C_1$-$C_6$ alkoxy, $C_1$-$C_6$ haloalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ cyanoalkoxy, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl.

Embodiment BB. A compound of Embodiment AA wherein $Q^1$ and $Q^2$ are each independently selected from A-1 through A-47;

each q is independently 0, 1, 2, 3 or 4;

$R^{1a}$ and $R^{1b}$ are each independently H, halogen, cyano, C(=O)$NR^{6a}R^{6b}$, $C_1$-$C_3$ alkyl, $C_1$-$C_3$ haloalkyl, $C_2$-$C_3$ alkenyl $C_2$-$C_3$ haloalkenyl, $C_2$-$C_3$ alkynyl, $C_2$-$C_3$ haloalkynyl, $C_3$-$C_5$ cycloalkyl, $C_3$-$C_5$ halocycloalkyl, $C_1$-$C_3$ alkoxy, $C_1$-$C_3$ haloalkoxy, $C_2$-$C_3$ alkenyloxy, $C_2$-$C_3$ haloalkenyloxy, $C_2$-$C_3$ alkynyloxy, $C_2$-$C_3$ haloalkynyloxy, $C_3$-$C_5$ cycloalkoxy, $C_1$-$C_3$ alkylamino or $C_2$-$C_3$ dialkylamino;

$R^2$ is $C_1$-$C_3$ alkyl, $C_1$-$C_3$ haloalkyl, $C_2$-$C_3$ alkenyl, $C_2$-$C_3$ haloalkenyl, $C_2$-$C_3$ cyanoalkyl, $C_1$-$C_3$ alkoxy or $C_1$-$C_3$ haloalkoxy; or $C_3$-$C_5$ cycloalkyl, optionally substituted with up to 3 substituents independently selected from halogen and methyl;

$R^3$ is cyano, hydroxy, $C_1$-$C_6$ alkyl, $C_1$-$C_6$ haloalkyl, $C_2$-$C_6$ cyanoalkyl, $C_1$-$C_6$ alkoxy, $C_1$-$C_6$ haloalkoxy, $C_2$-$C_6$ alkenyloxy, $C_2$-$C_6$ haloalkenyloxy or $C_2$-$C_6$ cyanoalkoxy;

each $R^5$ is independently cyano, halogen, nitro or -U-V-T; or $C_1$-$C_6$ alkyl, $C_2$-$C_6$ alkenyl, $C_2$-$C_6$ alkynyl, $C_3$-$C_6$ cycloalkyl, $C_2$-$C_6$ cyanoalkyl, $C_1$-$C_6$ alkoxy, $C_2$-$C_6$ alkenyloxy, $C_2$-$C_6$ alkynyloxy, $C_3$-$C_6$ cycloalkoxy, $C_2$-$C_6$ cyanoalkoxy, $C_2$-$C_6$ alkylcarbonyl or $C_2$-$C_6$ alkoxycarbonyl, each optionally substituted with up to 3 substituents independently selected from halogen;

each $R^{6a}$ and $R^{6b}$ is independently H, methyl, trifluoromethyl, methoxy or methylcarbonyl;

each U is independently a direct bond, O, C(=O) or NH;

each V is independently $C_1$-$C_3$ alkylene, wherein up to 1 carbon atom is C(=O), each optionally substituted with up to 2 substituents independently selected from halogen, methyl, halomethyl and methoxy;

each T is independently $NR^{8a}R^{8b}$ or $OR^9$;

each $R^{8a}$ and $R^{8b}$ is independently H, $C_1$-$C_3$ alkyl, $C_1$-$C_3$ haloalkyl, cyclopropyl, $C_2$-$C_3$ alkylcarbonyl or $C_2$-$C_3$ alkoxycarbonyl; and each $R^9$ is independently H, $C_1$-$C_3$ alkyl, $C_1$-$C_3$ haloalkyl, $C_2$-$C_3$ alkenyl, $C_2$-$C_3$ haloalkenyl or cyclopropyl Embodiment CC. A compound of Embodiment BB wherein J is J-1, J-2, J-4, J-6, J-8 or J-9;

$Q^1$ and $Q^2$ are each independently selected from A-1, A-2, A-4, A-19, A-25, A-28, A-31 and A-43;

each q is independently 1, 2 or 3;

$R^{1a}$ and $R^{1b}$ are each independently H, halogen, cyano, $C_1$-$C_3$ alkyl, $C_1$-$C_3$ haloalkyl, cyclopropyl, $C_1$-$C_3$ alkoxy or $C_1$-$C_3$ haloalkoxy;

$R^2$ is $C_1$-$C_3$ alkyl, $C_1$-$C_3$ haloalkyl, $C_1$-$C_3$ alkoxy or $C_1$-$C_3$ haloalkoxy; or cyclopropyl, optionally substituted with up to 2 substituents independently selected from halogen and methyl;

$R^3$ is cyano, hydroxy, $C_1$-$C_6$ alkyl, $C_1$-$C_6$ haloalkyl, $C_1$-$C_6$ alkoxy, $C_1$-$C_6$ haloalkoxy or $C_2$-$C_6$ cyanoalkoxy;

each $R^5$ is independently cyano, halogen, nitro or -U-V-T; or $C_1$-$C_3$ alkyl, $C_2$-$C_3$ alkenyl, $C_2$-$C_3$ alkynyl, $C_1$-$C_2$ alkoxy, $C_2$-$C_3$ alkenyloxy, $C_2$-$C_3$ alkynyloxy, $C_3$-$C_6$ cycloalkoxy or $C_2$-$C_3$ cyanoalkoxy, each optionally substituted with up to 3 substituents independently selected from halogen;

each U is independently a direct bond, O or NH;

each V is independently $CH_2$, $CH_2CH_2$, C(═O), $CH_2C$(═O) or C(═O)$CH_2$;

each $R^{8a}$ and $R^{8b}$ is independently H, $C_1$-$C_2$ alkyl, $C_1$-$C_2$ haloalkyl or cyclopropyl; and each $R^9$ is independently methyl or ethyl Embodiment DD. A compound of Embodiment CC wherein $Q^1$ and $Q^2$ are each independently selected from A-1, A-4 and A-19;

$R^{1a}$ and $R^{1b}$ are each independently H, halogen, cyano, $C_1$-$C_2$ alkyl, $C_1$-$C_2$ haloalkyl or cyclopropyl;

$R^2$ is $C_1$-$C_2$ alkyl, $C_1$-$C_2$ haloalkyl, $C_1$-$C_2$ alkoxy or $C_1$-$C_2$ haloalkoxy;

$R^3$ is $C_1$-$C_3$ alkyl, $C_1$-$C_3$ haloalkyl or $C_1$-$C_3$ alkoxy; and each $R^5$ is independently cyano, halogen, nitro, $C_1$-$C_2$ alkyl, $C_1$-$C_2$ alkoxy, $C_2$-$C_3$ alkenyloxy or $C_2$-$C_3$ cyanoalkoxy, each optionally substituted with up to 3 substituents independently selected from halogen.

Embodiment EE. A compound of Embodiment DD wherein

J is J-2, J-4, J-6 or J-8;

$Q^1$ and $Q^2$ are each A-1;

each q is independently 2 or 3;

$R^{1a}$ and $R^{1b}$ are each independently H, Br, Cl, F, cyano, methyl or ethyl;

$R^2$ is methyl, ethyl or methoxy;

$R^3$ is methyl or ethyl; and each $R^5$ is independently cyano, halogen, nitro, $C_1$-$C_2$ alkyl, $C_1$-$C_2$ alkoxy or $C_2$-$C_3$ cyanoalkoxy.

Embodiment FF. A compound of Embodiment EE wherein $R^{1a}$ and $R^{1b}$ are each independently H, Br, Cl, F, methyl or ethyl;

$R^2$ is methyl or ethyl; and each $R^5$ is independently cyano, Br, Cl, F, methyl or methoxy.

Embodiment GG. A compound of Embodiment FF wherein $R^{1a}$ and $R^{1b}$ are each independently H, Cl or methyl;

$R^2$ is methyl; and each $R^5$ is independently Br, Cl, F, methyl or methoxy.

Specific embodiments include compounds of Formula 1 selected from the group consisting of:

6-(2,4-difluorophenyl)-1-(3,5-dimethoxyphenyl)-3,5-dimethyl-4(1H)-pyridazinone (Compound 29);

1-(2-chloro-3,5-dimethoxyphenyl)-6-(2,4-difluorophenyl)-3,5-dimethyl-4(1H)-pyridazinone (Compound 33);

5-chloro-1-(2-chloro-3,5-dimethoxyphenyl)-6-(2-chloro-4-fluorophenyl)-3-methyl-2,4(1H,3H)-pyrimidinedione (Compound 35);

4-(2-chloro-3,5-dimethoxyphenyl)-5-(2-chloro-4-fluorophenyl)-2,6-dimethylpyrimidine (Compound 42);

2-chloro-4-(2-chloro-3,5-dimethoxyphenyl)-5-(2-chloro-4-fluorophenyl)-6-methylpyrimidine (Compound 49);

4-(2-chloro-3,5-dimethoxyphenyl)-2,6-dimethyl-5-(2,4,6-trifluorophenyl)pyrimidine (Compound 54);

4-(2-chloro-3,5-dimethoxyphenyl)-5-(2-chloro-4-fluorophenyl)-6-ethyl-2-methylpyrimidine (Compound 56);

4-(2-chloro-3,5-dimethoxyphenyl)-5-(2,6-difluorophenyl)-6-ethyl-2-methylpyrimidine (Compound 57);

4-(2-bromo-3,5-dimethoxyphenyl)-2,6-dimethyl-5-(2-chloro-4-fluorophenyl)pyrimidine (Compound 59);

5-(2-chloro-3,5-dimethoxyphenyl)-1,2-dihydro-1-methyl-2-oxo-6-(2,4,6-trifluorophenyl)-3-pyridinecarbonitrile (Compound 68);

1,2-dihydro-5-(3,5-dimethoxyphenyl)-1-ethyl-2-oxo-6-(2,4,6-trifluorophenyl)-3-pyridinecarbonitrile (Compound 69);

5-(2-chloro-3,5-dimethoxyphenyl)-1,2-dihydro-1-ethyl-2-oxo-6-(2,4,6-trifluorophenyl)-3-pyridinecarbonitrile (Compound 70);

3-chloro-6-(2-chloro-4-fluorophenyl)-1-(2-chloro-3,5-dimethoxyphenyl)-5-methyl-4(1H)-pyridazinone (Compound 92);

3-bromo-6-(2-chloro-4-fluorophenyl)-1-(2-chloro-3,5-dimethoxyphenyl)-5-methyl-4(1H)-pyridazinone (Compound 94);

6-(2-chloro-4-fluorophenyl)-3,5-dimethyl-1-(3,5-dimethoxyphenyl)-4(1H)-pyridazinone (Compound 97);

5-chloro-1-(2-chloro-5-methoxyphenyl)-6-(4-fluorophenyl)-3-methyl-4(1H)-pyridazinone (Compound 105);

5-chloro-1-(2-chloro-5-methoxyphenyl)-6-(2-chloro-4-fluorophenyl)-3-methyl-4(1)-pyridazinone (Compound 123);

5-bromo-1-(2-chloro-5-methoxyphenyl)-6-(2-chloro-4-fluorophenyl)-3-methyl-4(1)-pyridazinone (Compound 124);

5-(2-chloro-3,5-dimethoxyphenyl)-6-(2-chloro-4-fluorophenyl)-1,2-dihydro-1-methyl-2-oxo-3-pyridinecarbonitrile (Compound 156); and 5-(2-chloro-3,5-dimethoxyphenyl)-6-(2-chloro-4-fluorophenyl)-1,2-dihydro-1-ethyl-2-oxo-3-pyridinecarbonitrile (Compound 157).

In addition to the embodiments described above, this invention also provides a fungicidal composition comprising a compound of Formula 1 (including all stereoisomers, N-oxides, and salts thereof), and at least one other fungicide. Of note as embodiments of such compositions are compositions comprising a compound corresponding to any of the compound embodiments described above.

This invention also provides a fungicidal composition comprising a compound of Formula 1 (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to a plant seed, a fungicidally effective amount of a compound of Formula 1 (including all stereoisomers, N-oxides, and salts thereof). Of note as embodiments of such methods are methods comprising applying a fungicidally effective amount of a compound corresponding to any of the compound embodiments described above. Of particular note are embodiments where the compounds are applied as compositions of this invention.

One or more of the following methods and variations as described in Schemes 1-40 below can be used to prepare the compounds of Formula 1. The definitions of $Q^1$, $Q^2$, J, W, $R^{1a}$, $R^{1b}$, $R^2$, $R^3$, and $R^4$ in the compounds of Formulae 1-58 below are as defined above in the Summary of the Invention unless otherwise noted. Compounds of Formulae 1a, 1b, 1c, 1d, 1e, 1f and 1g (and subsets thereof) are various subsets of the compounds of Formula 1, and all substituents for Formulae 1a, 1b, 1c, 1d, 1e, 1f and 1g are as defined above for Formula 1 unless otherwise noted.

As shown in Scheme 1, compounds of Formula 1a (i.e. Formula 1 wherein J is J-1) can be prepared by reaction of compounds of Formula 2 wherein $X^1$ is a leaving group such as halogen or (halo)alkylsulfonate (e.g., Cl, Br, I, p-toluenesulfonate, methanesulfonate or trifluoromethanesulfonate) with an organometallic compound of Formula 3 under transition-metal-catalyzed cross-coupling reaction conditions, in the presence of a suitable palladium, copper or nickel catalyst. In this method compounds of Formula 3 are organoboronic acids (e.g., $M^1$ is $B(OH)_2$), organoboronic esters (e.g., $M^1$ is $B(—OC(CH_2)_3O—)$), organotrifluoroborates (e.g., $M^1$ is $BF_3K$), organotin reagents (e.g., $M^1$ is $Sn(n\text{-}Bu)_3$, $Sn(Me)_3$), Grignard reagents (e.g., $M^1$ is MgBr or MgCl) or organozinc reagents (e.g., $M^1$ is ZnBr or ZnCl). Suitable metal catalysts include, but are not limited to, palladium(II) acetate, palladium(II) chloride, tetrakis(triphenylphosphine)palladium, bis(triphenylphosphine)palladium(II) dichloride, dichloro[1,1'-bis(diphenylphosphino)ferrocene]palladium(II), bis(triphenylphosphine)dichloronickel(II) and copper(I) salts (e.g., copper(I) iodide, copper (I) bromide, copper(I) chloride, copper(I) cyanide or copper (I) triflate). Optimal conditions will depend on the catalyst used and the counterion attached to the compound of Formula 3 (i.e. $M^1$), as is understood by one skilled in the art. In some cases, the addition of a ligand such as a substituted phosphine or a substituted bisphosphinoalkane promotes reactivity. Also, the presence of a base such as an alkali carbonate, tertiary amine or alkali fluoride may be necessary for some reactions involving organoboron reagents of Formula 3. The reaction is typically carried out at temperatures ranging between about ambient and the boiling point of the solvent. The reaction can also be carried out at temperatures above the solvent boiling point by using a pressurized vessel, such as a microwave reactor or Fisher-Porter tube. For reviews of this type of reaction see: E. Negishi, *Handbook of Organopalladium Chemistry for Organic Synthesis*, John Wiley and Sons, Inc., New York, 2002; N. Miyaura, *Cross-Coupling Reactions: A Practical Guide*, Springer, New York, 2002; H. C. Brown et al., *Organic Synthesis via Boranes*, Vol. 3, Aldrich Chemical Co., Milwaukee, W I, 2002; Suzuki et al., *Chemical Review* 1995, 95, 2457-2483 and Molander et al., *Accounts of Chemical Research* 2007, 40, 275-286. Also, present Example 1 (Step D) and Example 3 (Step B) illustrate the method of Scheme 1 wherein $Q^2$ is a substituted thienyl and phenyl ring, respectively.

Compounds of Formula 1a (i.e. Formula 1 wherein J is J-1) wherein $Q^2$ is a N-linked ring can be prepared via palladium cross-coupling reactions using compounds of Formula 3a wherein the $Q^2$ ring contains an unsubstituted nitrogen atom (i.e. $Q^2$ ring has an NH ring member). For leading references see, for example, Buchwald et al., *Accounts of Chemical Research,* 1998, 31(12), 805-818 and Hartwig, *Angew. Chem. Int. Ed.,* 1998, 37, 2046-2067.

Compounds of Formulae 3 and 3a are commercially available and can be prepared by methods well-known in the art.

Scheme 1

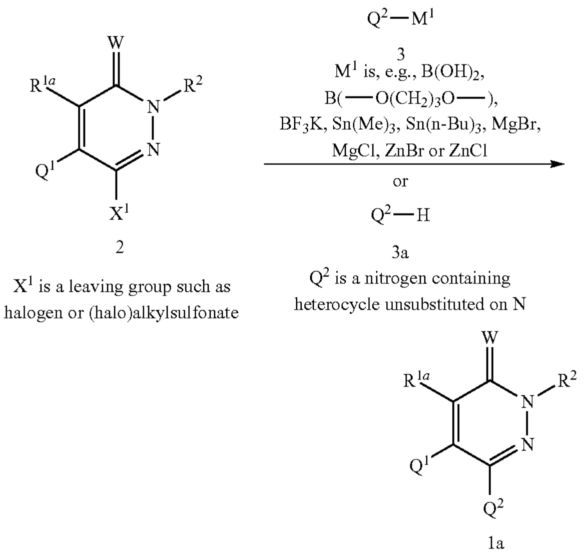

2

$X^1$ is a leaving group such as halogen or (halo)alkylsulfonate

3

3a

1a

A variety of metal-catalyzed coupling procedures reported in the chemistry literature offer alternatives to the conditions described in Scheme 1. For example, as outlined in Scheme 2, compounds of Formula 4 can be zincated via treatment with a zinc amide base followed by reaction with aryl halides of Formula 6 to provide compounds of Formula 1a (i.e. Formula 1 wherein J is J-1). Typical reaction conditions involve treatment of a compound of Formula 4 with a zinc amide base such as 2,2,6,6-tetramethylpiperidinylzinc chloride lithium chloride complex (CAS No. 1145881-09-9) in the presence of a metal catalyst and ligand to obtain an intermediate of Formula 5 (prepared in situ). The more covalent carbon-zinc bond of Formula 5 compared to intermediates with a carbon-magnesium bond, in some cases offers capabilities for introducing a broader range of $Q^2$ substituents onto the central pyridazinone ring. In a subsequent step, compounds of Formula 5 are contacted with compounds of Formula 6 wherein $X^2$ is a leaving group such as halogen (preferably Br, Cl or I) under Negishi type coupling conditions to provide compounds of Formula 1a (i.e. Formula 1 wherein J is J-1). Particularly useful catalyst/ligand combinations include tris(dibenzylideneacetone)dipalladium(0) and tri(2-furyl)phosphine. For relevant references see, for example, *Journal of Organic Chemistry* 2011, 76(23), 9648-9659; *ACS Catalysis* 2016, 6(3), 1540-1552; and WO 2020/069057. Present Example 2 (Step D) also illustrates the method of Scheme 2.

Alternatively, compounds of Formula 5 can first be reacted with a halogenating agent such as iodine or bromine. The resulting 6-bromo or 6-iodo-3(2H)-pyridazinones of Formula 2a (i.e. Formula 2, shown in Scheme 1, wherein $X^1$ is Br or I) can then be used in metal-catalyzed coupling reactions such as those described in Scheme 1 to prepare compounds of Formula 1a (i.e. Formula 1 wherein J is J-1). Particularly useful reaction conditions involve treatment of Formula 2a with boronic acids (e.g., Formula 3 wherein $M^1$ is $B(OH)_2$) under Suzuki-Miyaura reaction conditions. For Suzuki-Miyaura reaction conditions see, for example, *Tetrahedron* 2004, 60(52), 12177-12189; and *Journal of Medicinal Chemistry* 2006, 49(8), 2600-2610. A wide variety of catalysts are useful for this type of transformation; particularly useful as a catalyst is tetrakis(triphenylphosphine)palladium. Solvents such as tetrahydrofuran, acetonitrile, diethyl ether and dioxane are suitable.

Scheme 2

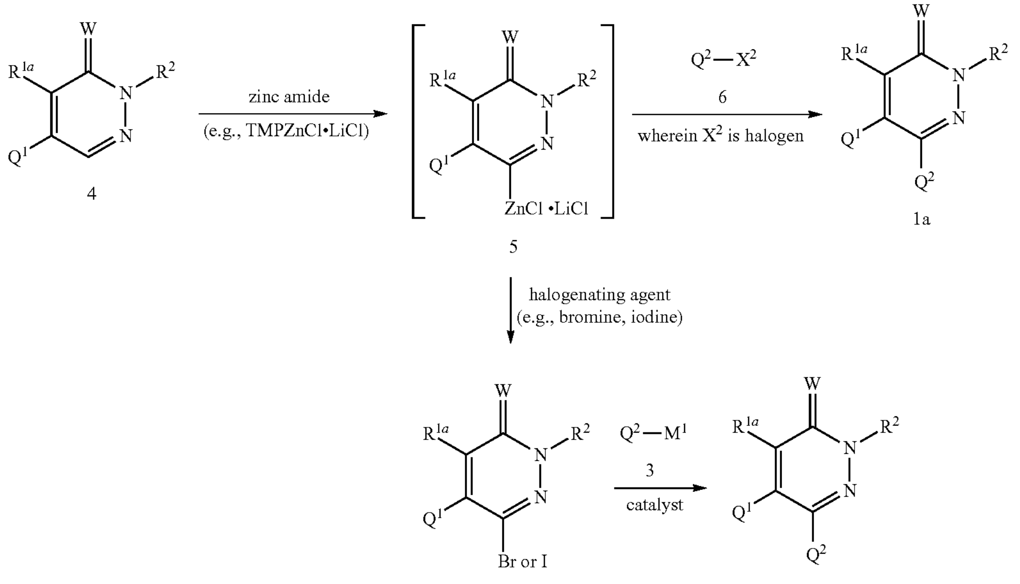

2a 1a

Scheme 3

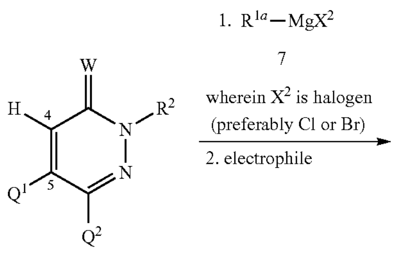

$1a^1$

-continued

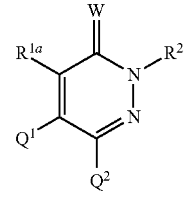

1a wherein $R^{1a}$ is alkyl, alkenyl, and the like

Compounds of Formula 1a (i.e. Formula 1 wherein J is J-1) wherein $R^{1a}$ is alkyl, alkenyl, and the like, can be prepared as shown in Scheme 3. In this method regioselective nucleophilic addition of an $R^{1a}$ group at the C-4 position of the pyridazinone ring is achieve by treatment of a compound of Formula $1a^1$ (i.e. Formula 1 wherein J is J-1 and $R^{1a}$ is H) with a Grignard reagent of Formula 7 followed by quenching with an electrophile such as bromine or copper(II) chloride. In cases where a leaving group is present at the C-5 position of the pyridazinone ring (i.e. a compound of Formula $1a^1$ wherein $Q^1$ is replaced with a leaving group) double addition at both the C-4 and C-5 positions can occur in a single synthetic step. The absence of such a leaving group in combination with quenching with an electrophile favors mono-addition at the C-4 position. For relevant references see *Organic Letters* 2011, 13(2), 272-275; and *Journal fuer Praktische Chemie* (*Leipzig*) 1985, 327(4), 536-542. Also, the method of Scheme 3 using methylmagnesium bromide and bromine is illustrated in present Example 3 (Step C).

Compounds of Formula $1a^1$ (i.e. Formula 1 wherein J is J-1 and $R^{1a}$ is H) can be prepared by the method of Scheme 1, as illustrated in present Example 3 (Step B).

As shown in Scheme 4, compounds of Formula 2 can be prepared by contacting compounds of Formula 8 wherein $X^2$ is a leaving group (preferably halogen) with boronic acids of Formula 9 analogous to the method described in Scheme 1. Particularly useful reaction conditions involve the use of a metal catalyst such as tetrakis(triphenylphosphine)palladium and bis(triphenyl-phosphine)palladium(II) dichloride, and a base such as sodium carbonate. It will be evident to one skilled in the art that regioselectivity of 5-versus 6-nucleophilic substitution can be affected by the nature of the nucleophile (i.e. Formula 9) and the substituents attached to the compound of Formula 8. In the method of Scheme 4, the target 5-substituted isomers of Formula 2 are particularly favored when starting from 5,6-dihalo-3(2H)-pyridazinones (e.g., 5,6-dichloro) of Formula 9. However, in most cases, if mixtures of both regioisomers are obtained, they can readily be separated using routine separation techniques known in the art. For references discussing regioselective metal-catalyzed coupling conditions of pyridazinones, see, *Journal of Organic Chemistry* 2009, 74, 5533-5540; and ARKIVOC 2011, (10), 229-253. Present Example 1 (Step B) and Example 3 (Step A) illustrate the method of Scheme 4 wherein $Q^1$ is a substituted phenyl and pyridinyl, respectively.

Scheme 4

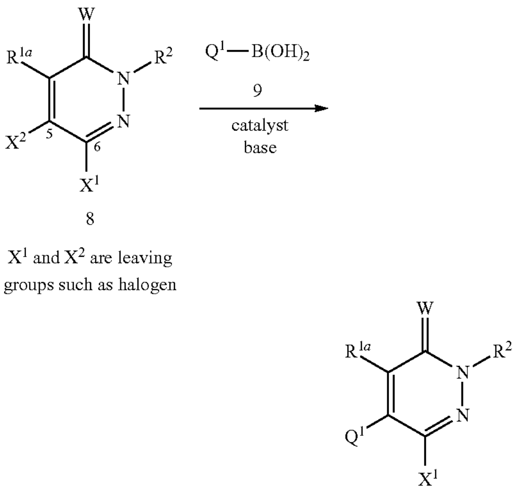

$Q^1$—$B(OH)_2$ 9

8

$X^1$ and $X^2$ are leaving groups such as halogen

2

$X^1$ is a leaving group such as halogen

Intermediate compounds of Formula 2 wherein $R^{1a}$ is alkyl, alkenyl, and the like, can also be prepared analogous to the method described in Scheme 3. Present Example 1 (Step C) illustrates the preparation of a compound of Formula 2 wherein $R^{1a}$ is methyl starting from a compound of Formula 2 wherein $R^{1a}$ is H.

As shown in Scheme 5, compounds of Formula 8 can be prepared from compounds of Formula 10 by reaction with an electrophile comprising $R^2$. Typically the reaction is run in the presence of a base such as potassium carbonate, potassium tert-butoxide, sodium ethoxide or sodium hydride and a polar solvent such as acetonitrile, N,N-dimethylformamide, tetrahydrofuran, acetonitrile or ethanol at temperatures ranging from about 0 to 100° C. In this context the expression "electrophile comprising $R^2$" means a chemical compound capable of transferring an $R^2$ moiety to a nucleophile (i.e. the nitrogen atom in Formula 10). Often electrophiles comprising $R^2$ have the formula $R^2$—$X^3$ wherein $X^3$ is a nucleofuge (i.e. leaving group in nucleophilic reactions). Typical nucleofuges include halide (e.g., Br, Cl, I) or sulfonate (e.g., mesylate, triflate, p-toluenesulfonate). Particularly useful electrophiles include, but are not limited to, alkyl halides, and the like, (e.g., iodoethane, allyl bromide, propargyl chloride) and alkyl sulfates (e.g., dimethyl sulfate). For reaction conditions see *Journal of Medicinal Chemistry* 1980, 23(12), 1398-1405. Also, present Example 1 (Step A) illustrates the method of Scheme 5. Compounds of Formula 10 are commercially available and can be prepared by methods well-known in the art.

Scheme 5

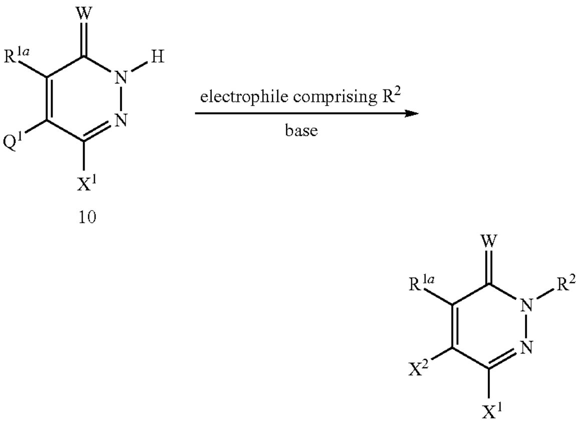

10

8

As shown in Scheme 6, compounds of Formula 4 (i.e. starting compounds in the method of Scheme 2) can be prepared using metal-catalyzed cross-coupling reaction conditions as described in Scheme 1. Particularly useful conditions include Pd-catalyzed cross-coupling of an aromatic halide of Formula 11 (preferably wherein $X^2$ is Br or I) with a substituted phenyl or heteroaromatic boronic acid of Formula 12 (i.e. wherein $M^1$ is $B(OH)_2$). For example, the reaction can be run in the presence of a catalyst (e.g., bis(triphenylphosphine)palladium(II) dichloride) and a base (e.g., potassium carbonate, potassium tert-butoxide or sodium hydride) in a polar solvent such as acetonitrile, N,N-dimethylformamide, tetrahydrofuran or dioxane, at temperatures ranging from about 0 to 100° C. One skilled in the art will appreciate that the group $X^2$ attached to compounds of Formula 11 should be selected in view of the relative reactivity of other functional groups present on Formula 11 (e.g., the $R^{1a}$ group), so that the group $X^2$ is displaced first to give the desired compounds of Formula 4. For optimal selectivity (i.e. preferential displacement of $X^2$), the $R^{1a}$ group should be less reactive than $X^2$ under cross-coupling conditions, thus allowing for differentiation between the two reactive centers. For example, use of compounds of Formula 11 wherein $X^2$ is I and $R^{1a}$ is Br, Cl or alkyl often allows for selective introduction of the $Q^1$ ring at the 5-position of the pyridazinone ring. For typical reaction conditions see, for example, Suzuki et al., *Chemical Review,* 1995, 95, 2457-2483. Also, present Example 2 (Step C) illustrates the method of Scheme 6 starting from a compound of Formula 11 wherein $R^{1a}$ is Cl and $X^2$ is I to provide a compound of Formula 4 wherein $Q^1$ is a substituted phenyl ring.

Intermediate compounds of Formula 11 wherein $R^2$ is alkyl, alkenyl, and the like, can be prepared from the corresponding compounds wherein $R^2$ is H using conditions analogous to those described in Scheme 5. Present Example 2 (Step A) illustrates the preparation of a compound of Formula 11 wherein $R^2$ is methyl.

Scheme 6

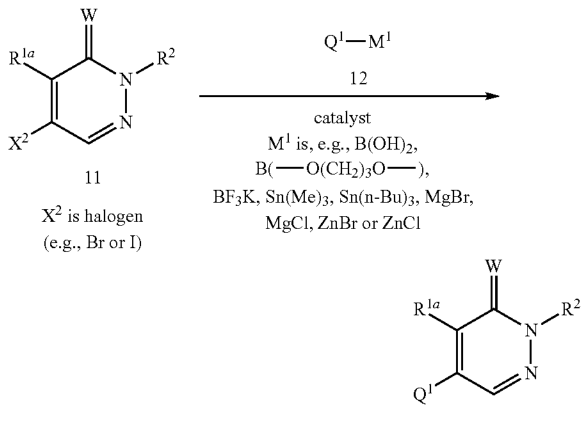

11

$X^2$ is halogen (e.g., Br or I)

4

In addition to the methods described above, there are wide variety of synthetic methods known in the art for the preparation of 3(2H)-pyridazinones which can be readily adapted to prepare compounds of Formula 1a (i.e. Formula 1 wherein J is J-1). For example, as shown in Scheme 7, cyclocondensation of α-keto acids or esters of Formula 13 with appropriately substituted hydrazines of Formula 14 followed by oxidation of the resultant dihydro compound of Formula 15, provides compounds of Formula 1a. Cyclization reactions of this type are well-documented in the chemical literature; see, for example, *Archives of Pharmacol Research* 2010, 33(1), 25-46; *Journal of Medicinal Chemistry* 2001, 44(16), 2511-2522; *Monatshefte fuer Chemie* 2004, 135(12), 1519-1527; *Indo Global Journal of Pharmaceutical Sciences* 2016, 6(2), 65-71; and WO 2021/163519 (see Example 1, Step D).

Scheme 7

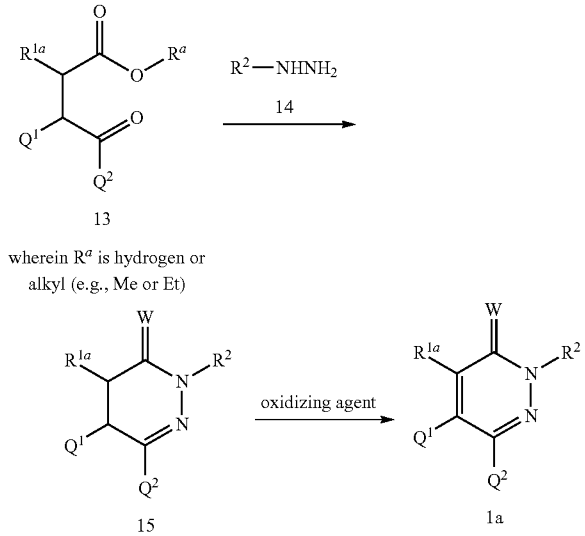

13 wherein $R^a$ is hydrogen or alkyl (e.g., Me or Et)

15

1a

Compounds of Formula 1b (i.e. Formula 1 wherein J is J-2) wherein $R^{1b}$ is alkyl, haloalkyl, alkenyl and the like, can be prepared in a two-step synthesis starting from the corresponding compounds of Formula $1b^1$ (i.e. Formula 1 wherein J is J-2 and $R^{1b}$ is $CH_2OH$), as shown in Scheme 8.

In the first step, the hydroxy moiety in Formula $1b^i$ is converted to an appropriate nucleophilic reaction leaving group $X^3$ (i.e. leaving group in nucleophilic reactions) to provide compounds of Formula 16 (note that when $X^3$ is halogen, compounds of Formula 16 are also compounds of Formula 1b wherein $R^{1b}$ is haloalkyl). Typically $X^3$ is halide (e.g., Br, Cl, I) or sulfonate (e.g., mesylate, triflate, p-toluenesulfonate). For example, alkyl chlorides of Formula 16 can be prepared by treating the hydroxy compounds of Formula $1b^1$ with thionyl chloride, oxalyl chloride, phosphorous oxychloride or phosphorus trichloride in a solvent such as dichloromethane or N,N-dimethylformamide. Alkyl bromides can be prepared in a similar reaction using phosphorus tribromide or phosphorus oxybromide. Iodoalkanes can be prepared by reacting compounds of Formula 16 wherein $X^3$ is Br or Cl with sodium iodide or potassium iodide in the presence of boron trifluoride etherate and an ether solvent such as 1,4-dioxane, or with hydroiodic acid in a solvent such as acetonitrile according to general methods described in *Tetrahedron Letters* 2001, 42(5), 951-953 and *Chinese Journal of Chemistry* 2004, 22(7), 619-621. Sulfonates can be prepared by reaction of Formula $1b^1$ with a sulfonating agent such as methanesulfonyl chloride, typically in the presence of a base, under conditions well-known to one skilled in the art of organic synthesis. Subsequent reduction of the halides or sulfonates of Formula 16 can be accomplished by treatment with a metal hydride. Typical reaction conditions include use of sodium borohydride or lithium aluminum hydride in a solvent such as dimethyl sulfoxide or diglyme. Methods for the preparation of halides and sulfonates from alcohols are well-known in the art; see, for example, *Compendium of Organic Synthetic Methods*, Volume 12, John Wiley and Sons, 2009; for reduction methods see *Journal of Organic Chemistry* 1969, 34(12), 3923-3926. Also, Example 8 (Steps A-B) and Example 31 (Steps A-B) illustrate the method of Scheme 8.

Scheme 8

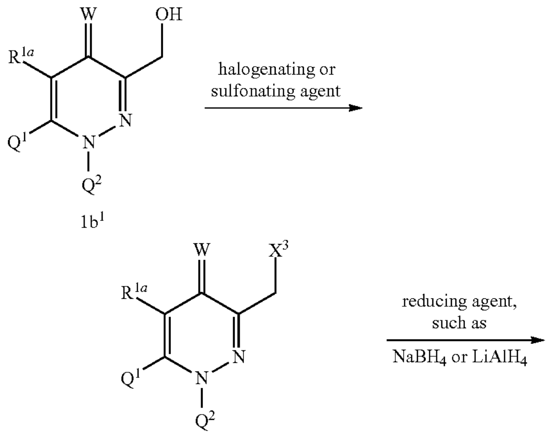

$1b^1$

16

$X^3$ is a nucleophilic leaving group, such as halide (e.g., Br, Cl, I) or sulfonate (e.g., mesylate, triflate, p-toluenesulfonate)

-continued

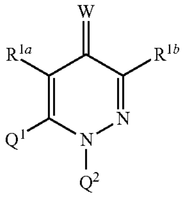

1b wherein $R^{1b}$ is alkyl, haloalkyl, alkenyl and the like

One skilled in the art will recognize that the method of Scheme 8 can also be performed starting from a compound of Formula $1b^1$ wherein $R^{1b}$ is a hydroxyalkyl group other than $CH_2OH$, thus providing other functionalized compounds of Formula 1b wherein $R^{1b}$ is alkyl, haloalkyl, alkenyl and the like.

Compounds of Formula $1b^1$ (i.e. Formula 1 wherein J is J-2 and $R^{1b}$ is $CH_2OH$) can be prepared in an esterification/hydrolysis synthesis starting from the corresponding carboxylic acids of Formula $1b^2$ (i.e. Formula 1 wherein J is J-2 and $R^{1b}$ is C(═O)OH), as shown in Scheme 9. In the first step, carboxylic acids of Formula $1b^2$ are converted to carboxylic esters of Formula $1b^3$ (i.e. Formula 1 wherein J is J-2 and $R^{1b}$ is C(═O)$OR^b$ and $R^b$ is alkyl, e.g. Me or Et) using general procedures known to those skilled in the art, such as heating the carboxylic acids with alcohols (e.g., methanol or ethanol) in the presence of an acid catalyst. Particularly useful conditions involve heating carboxylic acids of Formula $1b^2$ in methanol in the presence of thionyl chloride. Subsequent hydrolysis of carboxylic esters of Formula $1b^3$ provides compounds of Formula $1b^1$ (i.e. Formula 1 wherein J is J-2 and $R^{1b}$ is $CH_2OH$). Typical reaction conditions involve contacting a compound of Formula $1b^3$ with a metal base reducing agent such as sodium borohydride, lithium aluminum hydride and diisobutylaluminium hydride. The reaction can be run in a variety of solvents including, methanol, ethanol, dichloromethane, acetonitrile and tetrahydrofuran, and at reaction temperatures ranging from about −20 to 25° C. One skilled in the art will recognize that certain other functionalities that may be present in compounds of Formula $1b^3$ can also be reduced, thus requiring a suitable choice of catalyst and reaction conditions. For relevant references see, for example, Chemistry Letters 1983, (6), 835-8; *Angew. Chem. Int. Ed. Engl.* 1989, 28, 218-220; and *Journal of Organic Chemistry* 1991, 56(20), 5964-5965. Also, Examples 5-6 illustrate the method of Scheme 9.

Alternatively, carboxylic acids of Formula $1b^2$ can be reduced directly to their corresponding alcohols of Formula $b^1$ by treatment with sodium borohydride and iodine using conditions reported in the *Journal of Organic Chemistry* 1991, 56, 5964-5965. In a typical procedure, a solution of a carboxylic acid of Formula $1b^2$ in tetrahydrofuran is added to a suspension of sodium borohydride in tetrahydrofuran and the reaction mixture is stirred until gas evolution ceases, and then iodine is added. Other known methods for the selective reduction of carboxylic acids of Formula $1b^2$ can also be employed such as by activation of the carboxylic acid with a mixed anhydride (e.g., isobutyl chloroformate and N-methylmorpholine) followed by the reaction of sodium borohydride as illustrated in present Example 30 (for a relevant reference see *International Journal of Organic Chemistry* 2022, 12, 116-112).

Scheme 9

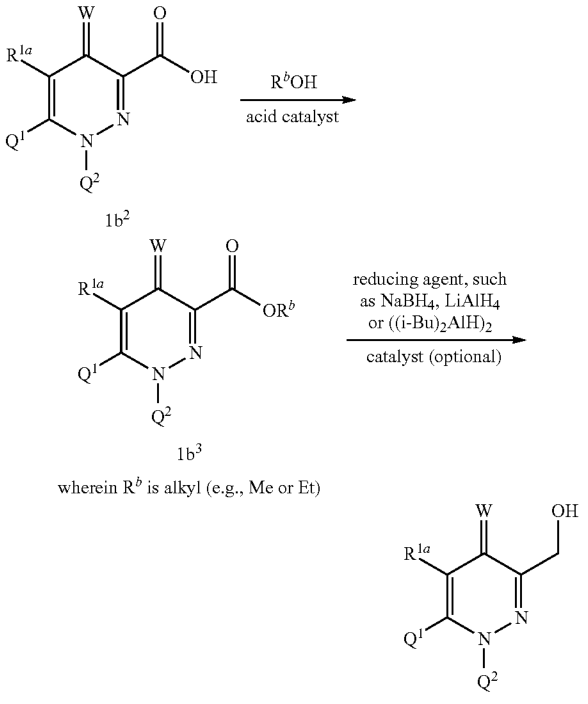

$1b^2$ $1b^3$ wherein $R^b$ is alkyl (e.g., Me or Et)

$1b^1$

As shown in Scheme 10, compounds of Formula $1b^2$ (i.e. Formula 1 wherein J is J-2 and $R^{1b}$ is C(═O)OH) can also be subjected to reaction conditions that facilitate Curtius rearrangement to provide carbamates of Formula $1b^4$ and amines of Formula $1b^5$. In this method a carboxylic acid of Formula $1b^2$ is first converted to an isocyanate through an acyl azide intermediate. The resulting stable isocyanate can then be readily transformed into a variety of carbamates and amines of Formula $1b^4$ and Formula $1b^5$. Amines of Formula $1b^5$ can also be obtained by treating a carbamate of Formula $1b^4$ with an acid such as, for example, trifluoroacetic acid or hydrochloric acid. The Curtius rearrangement is widely reported in the literature, for a review see *Chemical Reviews* 1988, 88(2), 297-368. A particularly useful procedure for preparing compounds of Formulae $1b^4$ and $1b^5$, involves reacting a carboxylic acid of Formula $1b^2$ with diphenylphosphoryl azide in the presence of a compound of formula $R^c$—OH and in a solvent at temperatures ranging between about ambient to the boiling point of the solvent to obtain the carbamate of Formula $1b^4$. A variety of solvents can be employed in this method, particularly useful solvents include alcohols, dichloromethane or dioxanes. When the reaction is carried out in tert-butyl alcohol, the alcohol acts as both the reactant and solvent providing compounds wherein $R^c$ is tert-butyl, which can subsequently be treated with trifluoroacetic acid to provide the amide of Formula $1b^5$. For a relevant reference describing this procedure see *Journal of the American Chemical Society* 1972, 94, 6203-6205. In addition to the Curtius rearrangement, other structural rearrangement reactions have been reported in the chemical literature which can be readily adapted to prepare compounds of the present invention. For example, the Hofmann, Schmidt and Lossen rearrangements which generally involve nucleophilic migrations from a carbon to an electron deficient nitrogen center. For articles about these type of rearrangements; see, for example, *Comprehensive Organic Synthesis* 1991, 6, 795-828; and *Chemical Review* 1934, 14(2), 219-250.

Scheme 10

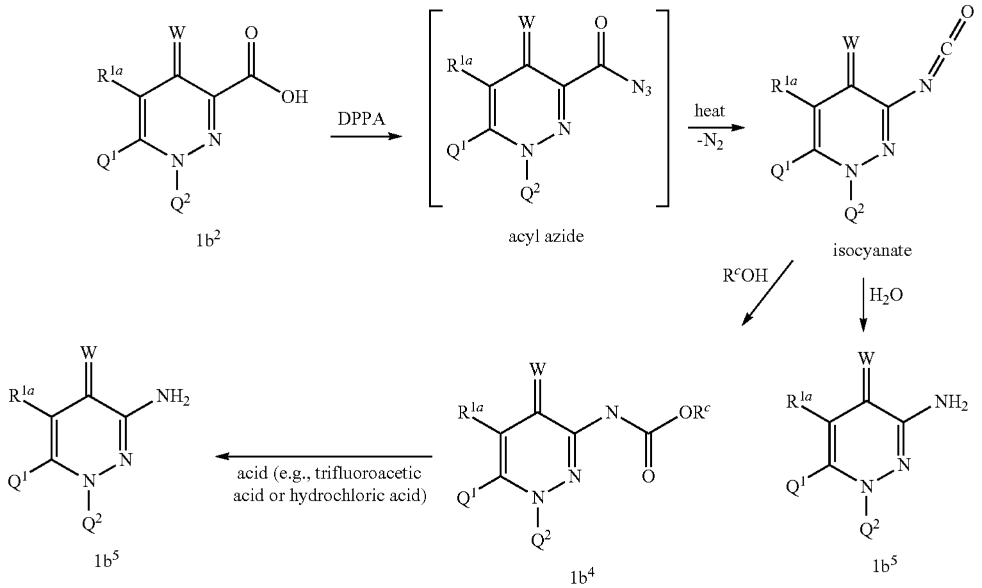

wherein $R^c$ is $C_1$-$C_5$ alkyl

As shown in Scheme 11, compounds of Formula 1b (i.e. Formula 1 wherein J is J-2) wherein $R^{1b}$ is halogen or cyano can be prepared from corresponding amines of Formula $1b^5$ (i.e. Formula 1 wherein J is J-2 and $R^{1b}$ is $NH_2$) using Sandmeyer reaction conditions. For example, amines of Formula $1b^5$ can be converted to diazonium salts and then reacted with a nucleophile such as a copper salt (e.g., copper(I) halide, copper(II) halide or copper(I) cyanide) to provide compounds of Formula 1b wherein $R^{1b}$ is halogen or cyano. Other nucleophiles can also be employed in this method, such as thiols, water, and diiodomethane or potassium iodide to provide compounds wherein $R^{1b}$ is alkylthio, hydroxy or iodo, respectively. The diazonium salt formed from the amine of Formula $1b^5$ is generated under standard conditions, for example, using a strong acid (e.g., an aqueous solution of hydrochloric acid or hydrobromic) and sodium nitrite or using non-aqueous conditions (for reference see *Molecules* 2016, 21(7), 918). For a review of the Sandmeyer reaction see *Chemical Reviews* 1947, 40(2), 251-277; *Comprehensive Organic Name Reactions and Reagents*, John Wiley & Sons, 2471-2475; and *Molecular Diversity* 2022, 26(3), 1837-1873. Also, copper salt, tert-butyl nitrite and acetonitrile can be used according to the general method disclosed in *Journal of Heterocyclic Chemistry* 1991, 28, 1003-1011.

Scheme 11

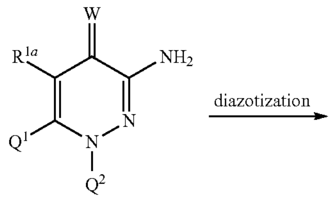

$1b^5$

-continued

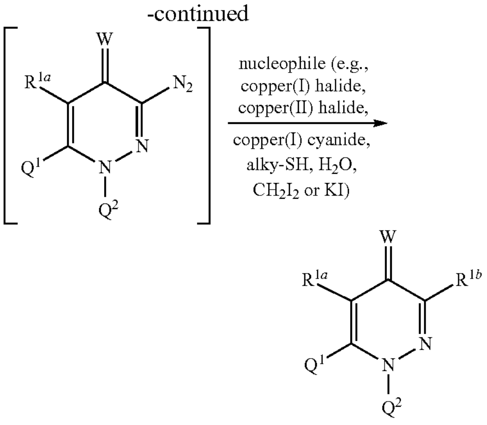

1b
wherein $R^{1b}$ is halogen, CN, OH or alkylthio

As shown in Scheme 12, compounds of Formula 1b (i.e. Formula 1 wherein J is J-2) wherein $R^{1b}$ is halogen can be subjected to nucleophilic substitution reactions to provide compounds of Formula 1b (i.e. Formula 1 wherein J is J-2) wherein $R^{1b}$ is alkoxy, alkylthio, alkylamino, and the like. Typical reaction conditions include contacting a compound of Formula 1b wherein $R^{1b}$ is halogen with an appropriate nucleophile in the presence of a suitable base. The reaction is carried out in a solvent such as N,N-dimethylformamide, acetonitrile, tetrahydrofuran, dioxanes, dimethylacetamide and dimethyl sulfoxide at a temperature between about 0 to 80° C. Nucleophiles useful in the method of Scheme 12 include, but are not limited to, alcohols, alkyl thiols and alkyl amines. Suitable bases include alkali hydrides (e.g., lithium hydride and sodium hydride), alkali hydroxides (e.g., potassium hydroxide and sodium hydroxide), alkali alkoxides (e.g., potassium tert-butoxide and sodium tert-butoxide), alkali hexamethyldisilazide (e.g., lithium, sodium or potassium hexamethyldisilazide), trialkylamines, 1,8-diazabicyclo[5.4.0]undec-7-ene (DBU) and 1,5-diazabicyclo [4.3.0]non-5-ene (DBN). The optimal base will vary depending on the nucleophile used, as is understood by one skilled in the art.

Scheme 12

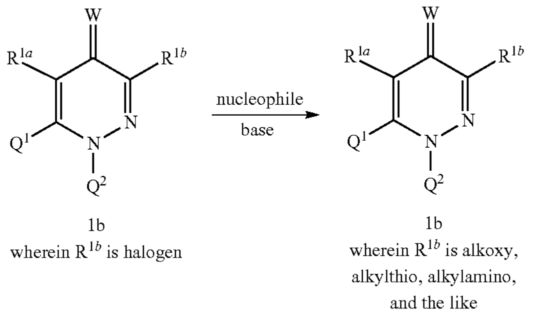

1b
wherein $R^{1b}$ is halogen
1b
wherein $R^{1b}$ is alkoxy, alkylthio, alkylamino, and the like As shown in Scheme 13, compounds of Formula 1b (i.e. Formula 1 wherein J is J-2) wherein $R^{1b}$ is halogen can be prepared from corresponding compounds of Formula 1b wherein $R^{1b}$ is H. Halogenation can be achieved using a variety of halogenating agents known in the art such as elemental halogen (e.g., $Cl_2$, $Br_2$, $I_2$), sulfuryl chloride, iodine monochloride or a N-halosuccinimide (e.g., NBS, NCS, NIS) in an appropriate solvent such as N,N-dimethylformamide, carbon tetrachloride, acetonitrile, dichloromethane or acetic acid.

Scheme 13

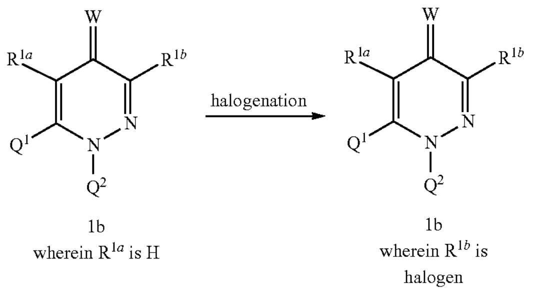

1b
wherein $R^{1a}$ is H
1b
wherein $R^{1b}$ is halogen

As shown in Scheme 14, compounds of Formula $1b^6$ (i.e. Formula 1 wherein J is J-2) wherein $R^{1b}$ is alkoxycarbonyl can be prepared in a two-step synthesis. In the first step, compounds of Formula 17 are halogenated analogous to the method of Scheme 13. In a subsequent step, compounds of Formula 18 can be reacted with various organozinc reagents and then coupled under Negishi reaction conditions (analogous to the method described in Scheme 2) with compounds of Formula 19 to provide compounds of Formula $1b^6$. For reaction conditions, see present Example 29, Steps C to D.

Starting compounds of Formula 17 can be prepared as illustrated in present Example 29, Steps A to B.

Scheme 14

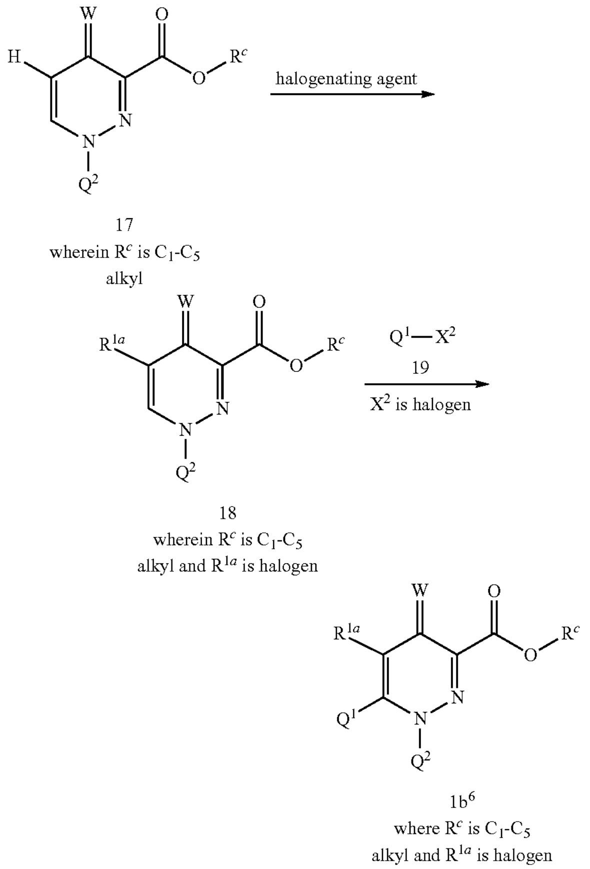

17
wherein $R^c$ is $C_1$-$C_5$ alkyl
18
wherein $R^c$ is $C_1$-$C_5$ alkyl and $R^{1a}$ is halogen
$1b^6$
where $R^c$ is $C_1$-$C_5$ alkyl and $R^{1a}$ is halogen As shown in Scheme 15, compounds of Formula $1b^2$ (i.e. compounds of Formula 1 wherein J is J-2 and $R^{1b}$ is C(═O)OH) can be prepared via rearrangement of hydrazones of Formula 20 under acid or base conditions. For example, hydrazones of Formula 20 can be contacted with an aqueous acid, such as hydrochloric acid, trifluoroacetic acid, sulfuric acid, methanesulfonic acid, p-toluenesulfonic acid or acetic acid, or the like; or an aqueous base, such as sodium carbonate, sodium hydroxide, or an alcoholic secondary amine such as morpholine, piperidine, dialkylamine, or the like, at a temperature from about 0 to 150° C., preferably about 40 to 100° C., to provide compounds of Formula $1b^2$. Rearrangement reactions of this type are well-documented in the chemical literature; see, for example, *Journal of the American Chemical Society* 1956, 78, 624-626; *Journal of Chemical Research, Synopses* 2002, (5), 228-230; U.S. Pat. Nos. 7,915,258 and 2,835,671. Also, Example 4 (Step E) illustrates the method of Scheme 15 using hydrochloric acid.

Scheme 15

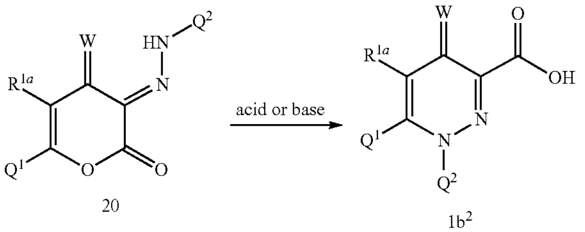

20

$1b^2$

Compounds of Formula 20 wherein W is O can be prepared as shown in Scheme 16. In this method, a diazonium salt of Formula 22 is first generated using known diazotization conditions. For example, treatment of Formula 22 with sodium nitrite in the presence of a strong acid, such as an aqueous solution of hydrochloric acid or hydrobromic acid (for reaction conditions, see U.S. Pat. No. 7,915,258). Non-aqueous conditions can also be employed using, for example, tert-butyl nitrite as the diazotizing reagent (for reaction conditions, see *Molecules* 2016, 21, 918). Reaction of the diazonium salt formed from the compound of Formula 22 with an alcohol of Formula 21 provides compounds of Formula 20. Present example 4 (Step D) illustrates the method of Scheme 16.

Scheme 16

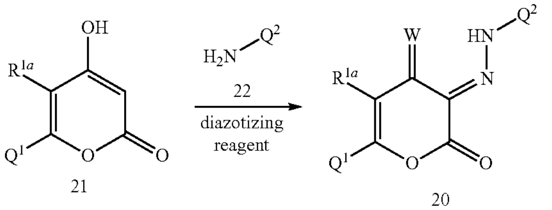

21

20 wherein W is O

As shown in Scheme 17, compounds of Formula 21 can be prepared by cyclization of 1,3,5-ketoesters of Formula 23 under acid or base catalyzed dehydrative conditions. A variety of general acid or base reaction conditions described in the synthetic literature can be used in the method of Scheme 17. For example, heating 1,3,5-diketoesters of Formula 23 in a high boiling solvent such as toluene or xylenes in the presence of an acid such as p-toluenesulfonic acid, sulfuric acid or methanesulfonic acid provides compounds of Formula 21. Alternatively, the reaction can be run in the presence of a base such as 1,8-diazabicyclo[5.4.0]undec-7-ene (DBU) and a solvent such as methanol. Examples of this synthetic methodology can be found in *Journal of Heterocyclic Chemistry* 1995, 32(5), 1657-1660; *Synlett* 2017, 28, 1596-1600; *Organic Letters* 2008, 10(12), 2569-2572; and U.S. Pat. No. 5,808,062. Also, the method of Scheme 17 is illustrated in Example 4 (Step C).

Scheme 17

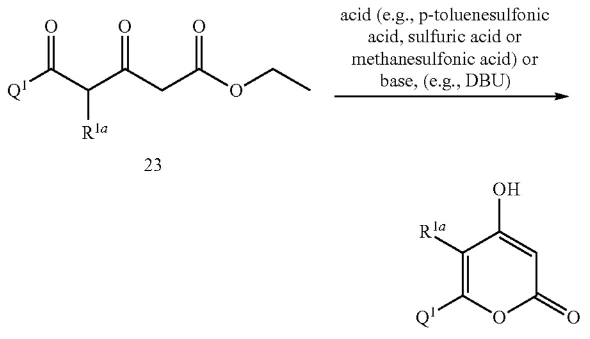

23

21

As shown in Scheme 18, 1,3,5-ketoesters of Formula 23 can be prepared from corresponding β-ketoesters of Formula 24. In this method, the β-ketoester is first deprotonated by treatment with one equivalent of a suitable base such as a metal hydride, e.g., sodium hydride, in a solvent such as diethyl ether or tetrahydrofuran. The resulting malonate solution is then treated with a second equivalent of a stronger base such as an alkyllithium, e.g., n-butyllithium or lithium diisopropylamide, followed by reaction with an amide of Formula 25 (e.g., Weinreb amides) to provide compounds of Formula 23. The method of Scheme 18 is illustrated in Example 4 (Step B).

Amides of Formula 25 can be prepared by methods known in the art. For example, reaction of the corresponding acid chlorides with N,O-dimethylhydroxylamine hydrochloride as illustrated in present Example 4 (Step A).

Scheme 18

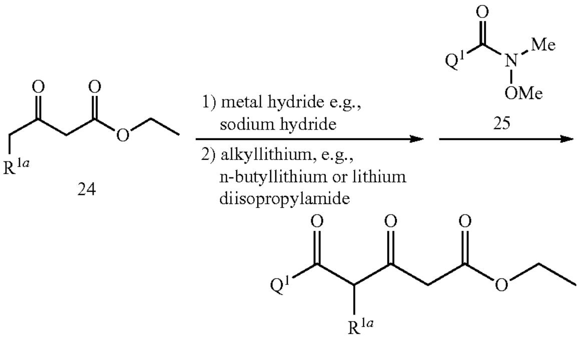

24

23

One skilled in the art will appreciate that for some compounds of Formula 1b (i.e. Formula 1 wherein J is J-2) the $R^5$ substituents attached to the $Q^1$ and $Q^2$ rings may be more conveniently incorporated after forming the central pyridazinone ring with $Q^1$ and $Q^2$ attached. For example, when $Q^1$ and/or $Q^2$ are phenyl, a halogen atom can be introduced onto the ring by treatment with a halogenating agent such as N-bromosuccinimide (NBS), N-chlorosuccinimide (NCS), N-iodosuccinimide (NIS), bromine, sodium bromite, thionyl chloride, oxalyl chloride, phenylphosphonic dichloride or phosgene. Depending on the reactants and reaction conditions, halogenation can result in mixtures of regioisomers. The activation or deactivation of the $Q^1$ and/or $Q^2$ phenyl ring toward electrophilic halogenation will be strongly influenced by the other substituents attached to the phenyl ring, with electron-withdrawing groups favoring halogenation. Scheme 19 illustrates a specific example for the preparation of compounds of Formula $1b^{8a}$ (i.e. Formula 1 wherein J is J-2 and $Q^1$ is 2,4-difluorophenyl and $Q^2$ is 2-chloro-3,5-dimethoxyphenyl) and Formula $1b^{8b}$ (i.e. Formula 1 wherein J is J-2 and $Q^1$ is 2,4-difluorophenyl and $Q^2$ is 4-chloro-3,5-dimethoxyphenyl) from the corresponding compound of Formula $1b^7$ (i.e. Formula 1 wherein J is J-1, $Q^1$ is 2,4-difluorophenyl and $Q^2$ is 3,5-dimethoxyphenyl). Present Example 7 illustrates the method of Scheme 19. In cases where regioisomeric mixtures are produced, the products can be separated using routine techniques known in the art.

Scheme 19

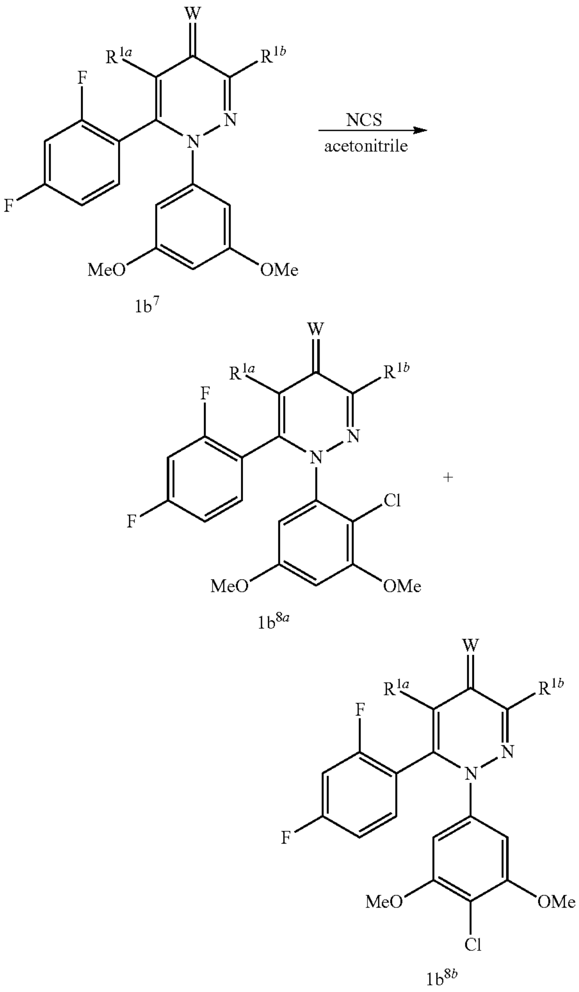

$1b^7$ $1b^{8a}$ $1b^{8b}$

As shown in Scheme 20, compounds of Formula 1e (i.e. Formula 1 wherein J is J-4) can be prepared analogous to the method of Scheme 1. In this method, compounds of Formula 27 are the same as the organometallic compounds as described for Formula 3, and compounds of Formula 27a are the same heterocycles as described for compounds of Formula 3a in Scheme 1. The reactions are carried out in the same manner as described in Scheme 1. Present Example 9 (Step E) and Example 12 (Step E) illustrate the method of Scheme 20 wherein $Q^1$ is a substituted phenyl ring.

Scheme 20

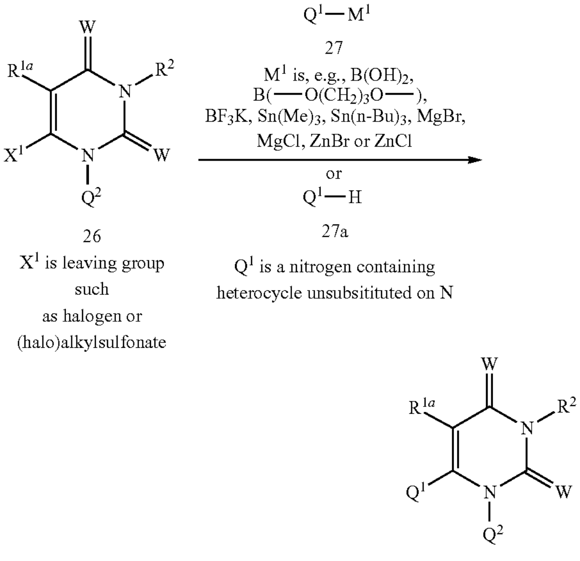

26

$X^1$ is leaving group such as halogen or (halo)alkylsulfonate

1c

As shown in Scheme 21, intermediates of Formula 26 are readily prepared from corresponding compounds of Formula 28 by treatment with a halogenating or sulfonating agent using standard techniques known in the art. For example, reacting compounds of Formula 28 with phosphorous trichloride, phosphorous pentachloride, phosphorous oxychloride or thionyl chloride in a suitable solvent such as dichloromethane provides compounds of Formula 26 wherein $X^1$ is chlorine. Compounds of Formula 26 wherein $X^1$ is (halo)alkylsulfonate can be prepared from corresponding compounds of Formula 28 by reaction, for example, with trifluoromethanesulfonic anhydride in the presence of a mild nonnucleophilic base. For typical reaction conditions see, for example, *Australian Journal of Chemistry* 1968, 21(2) 467-76; *Bioorganic & Medicinal Chemistry Letters* 2011, 21(10), 2958-2961; *Journal of Medicinal Chemistry* 2014, 57, 435-448; *Accounts of Chemical Research* 1988, 21(4), 47-53 and WO 2013/183035. Also, present Example 9 (Step D) and Example 12 (Step D) illustrate the method of Scheme 21.

Scheme 21

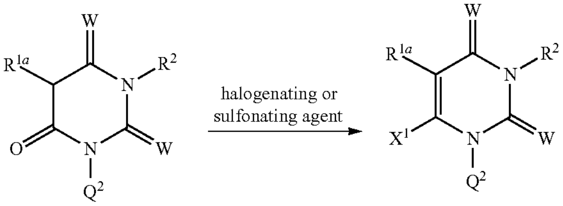

28

26

$X^1$ is a leaving group such as halogen or (halo)alkylsulfonate

Compounds of Formula 28 can be prepared by reaction of compounds of Formula 30 with a malonic derivative of Formula 30 as shown in Method A of Scheme 22. Typically the reaction is run in a solvent such as dichloromethane, chloroform, dichloroethane, tetrahydrofuran or toluene. Alternatively, compounds of Formula 29 can be reacted with esters of Formula 31 in the presence of a metal alkoxide such as sodium ethoxide, sodium methoxide, potassium tert-butoxide and in a solvent such as ethanol, methanol or tert-butanol, as shown in Method B of Scheme 22. Both methods are typically conducted at a temperature between about 50° C. to the boiling point of the solvent or solvent mixture. For reaction conditions see, *Dyes and Pigments* 2018, 149, 543-552; and WO 2002/068057. Also, Example 9 (Step C) and Example 12 (Step C) illustrate the method of Scheme 22.

Scheme 22

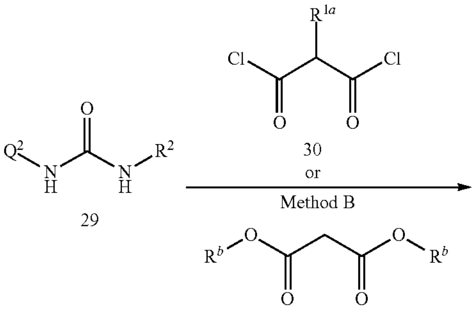

29, 30, 31 wherein $R^b$ is alkyl (e.g., Me or Et)

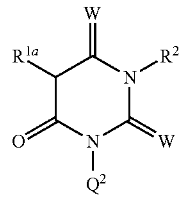

28

Compounds of Formula 29 can be synthesized by a variety of means. For example, as shown in Scheme 23, reaction of carbamates of Formula 32 wherein Rd is a leaving group such as phenoxy or tert-butoxy with amines of Formula 33 in a solvent such as tetrahydrofuran, 1,4-dioxane, dichloromethane, toluene or acetonitrile at ambient temperature provides compounds of Formula 29. For relevant references see, for example, *Synthesis* 1989, 6, 423-425. Also, present Example 9 (Step B) and Example 12 (Step B) illustrate the method of Scheme 23. Other general methods have been reported in the literature for the preparation of ureas which can be readily adapted to prepare compounds of Formula 29. For example, reaction of isocyanates with amines according to the procedure reported in the *Journal of Organic Chemistry* 2000, 65, 1549-1551; and *Organic Process Research* & Development 2002, 6, 759-761.

Scheme 23

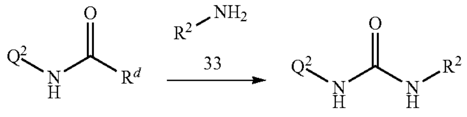

33

32 wherein the $R^d$ is a leaving group such as phenoxy or tert-butoxy

29

As shown in Scheme 24, compounds of Formula 32 can be prepared by coupling of an acid chloride of Formula 35 with an amine of Formula 34 in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. Acid salts of Formula 34 amines can also be used in this reaction, provided that at least 2 equivalents of an acid scavenger is present. Typical acids used to form salts with amines include hydrochloric acid, oxalic acid and trifluoroacetic acid. For reaction conditions, see present Example 9 (Step A) and Example 12 (Step A).

Scheme 24

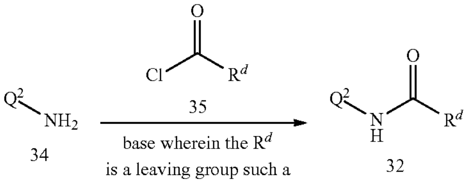

35

34

32

Compounds of Formula 1c (i.e. Formula 1 wherein J is J-4) wherein $R^{1a}$ is halogen can be prepared from corresponding compounds of Formula 1c wherein $R^{1a}$ is H. Halogenation can be achieved using a variety of halogenating agents known in the art such as elemental halogen (e.g., $Cl_2$, $Br_2$, $I_2$), sulfuryl chloride, iodine monochloride or a N-halosuccinimide (e.g., NBS, NCS, NIS), and in an appropriate solvent such as N,N-dimethylformamide, carbon tetrachloride, acetonitrile, dichloromethane or acetic acid. Depending on the reactants and reaction conditions, halogenation can result in mixtures of regioisomers which can be separated using routine techniques known in the art. Scheme 25 illustrates a specific example for the preparation of compounds of Formula $1c^{2a}$ (i.e. Formula 1 wherein J is J-4, $R^{1a}$ is Cl and $Q^2$ is 3,5-dimethoxyphenyl) and Formula $1c^{2b}$ (i.e. Formula 1 wherein J is J-4, $R^{1a}$ is H and $Q^2$ is 2-chloro-3,5-dimethoxyphenyl) from the corresponding compound of Formula 103 (i.e. Formula 1 wherein J is J-4, $R^{1a}$ is H and $Q^2$ is 3,5-dimethoxyphenyl). Present Example 11 illustrates the method of Scheme 25.

Scheme 25

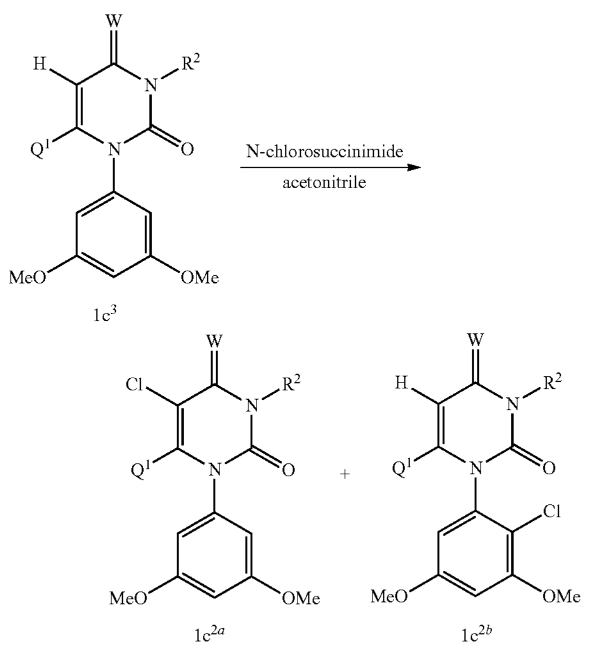

$1c^3$

+

$1c^{2a}$ $1c^{2b}$

As shown in Scheme 26, compounds of Formula 1d (i.e. Formula 1 wherein J is J-6) can be prepared analogous to the method of Scheme 1. Present Example 14 (Step B), Example 16 (Step D), Example 18 (Step D), Example 20 and Example 21 (Step E) illustrate the method of Scheme 26 wherein $Q^2$ is a substituted phenyl ring.

Scheme 26

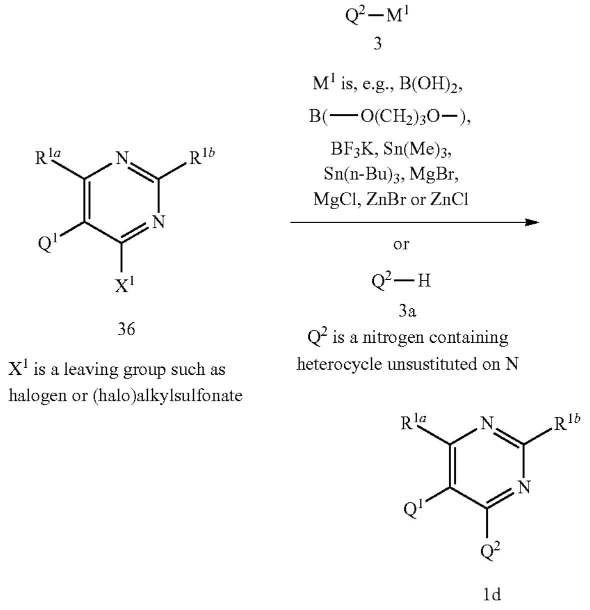

36

1d

One skilled in the art will recognize that the method of Scheme 26 can be perform when the $X^1$ and $Q^1$ functionalities attached to the compound of Formula 36 are reversed, thus allowing for the introduction of a $Q^1$ ring instead of the $Q^2$ ring.

As shown in Scheme 27, starting compounds of Formula 36 can be prepared analogous to the method of Scheme 1. In this method, compounds of Formula 27 are the same as the organometallic compounds as described for Formula 3, and compounds of Formula 27a are the same heterocycles as described for compounds of Formula 3a in Scheme 1. As will be evident to one skilled in the art, $X^2$ group attached to compounds of Formula 37 should be selected in view of the relative reactivity of other functional groups present on Formula 37 (e.g., the $X^1$ group), so that the group $X^2$ is displaced first to give the desired compounds of Formula 36. For optimal selectivity (i.e. preferential displacement of $X^2$), the $X^1$ group should be less reactive than $X^2$ under cross-coupling conditions, thus allowing for differentiation between the two reactive centers. For example, use of compounds of Formula 37 wherein $X^2$ is I and $X^1$ is Br, Cl or alkyl sulfonate often allows for selective introduction of the $Q^1$ ring at the 5-position of the pyrimidine ring. For typical reaction conditions see, for example, Suzuki et al., *Chemical Review*, 1995, 95, 2457-2483, and references cited in Scheme 1. Also, Example 14 (Step A) illustrates the method of Scheme 27 starting from a compound of Formula 37 wherein $X^1$ is Cl and $X^2$ is I to provide a compound of Formula 36 wherein $Q^1$ is a substituted phenyl ring.

Scheme 27

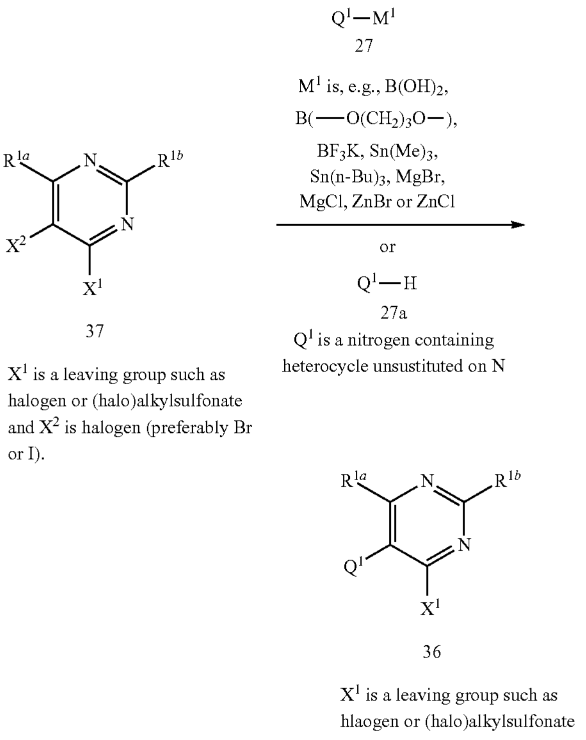

37

36

In an alternative method, as outlined in Scheme 28, compounds of Formula 1d (i.e. Formula 1 wherein J is J-6) wherein $R^{1b}$ is alkyl, alkylthio, alkylsulfonyl, and the like, can be prepared by cyclic condensation of malonate derivatives of Formula 38 with a substituted urea of formula $NH_2C(=NH)R^{1b}$, followed by halogenation to obtain compounds of Formula 40 which are useful intermediates in transition metal-catalyzed cross-coupling reactions to prepare compounds of Formula 1d (i.e. Formula 1 wherein J is J-6). The cyclization reaction can be carried out without solvent other than the compound of Formula 38 and the urea derivative, or in a liquid phase with a solvent such as methanol, ethanol, acetonitrile, dichloromethane, N,N-dimethylformamide, dimethyl sulfoxide and 1-methyl-2-pyrrolidinone, at a temperature ranging from about ambient to 200° C. It is generally advantageous to conduct the reaction in the presence of a suitable base. Suitable bases for use in the method of Scheme 28 include, for example, metal alkoxides such as potassium tert-butoxide, sodium methoxide, sodium ethoxide and the like; or an alkali metal hydride such as sodium hydride and the like; or an organic base such as triethylamine, pyridine, 4-dimethylaminopyridine, N-methylmorpholine, 1,8-diazabicyclo[5.4.0]undec-7-ene (DBU) and the like; or an inorganic salt such as potassium carbonate, sodium carbonate, sodium hydrogen carbonate and the like. Subsequent halogenation of Formula 39 compounds can be achieved using a variety of halogenating agents known in the art. For example, dichloropyrimidines of Formula 40 can be prepare by reacting compounds of Formula 39 with a chlorinating agent such as sulfuryl chloride, phosphoric trichloride or phosphorus pentachloride in an appropriate solvent such as carbon tetrachloride, acetonitrile or dichloromethane. Compounds of Formula 40 can be subjected to metal catalyzed cross-coupling reactions analogous to the method of Scheme 1 to provide compounds of Formula 1d (i.e. Formula 1 wherein J is J-6). For references illustrating the method of Scheme 28 see, for example, *Bioorganic & Medicinal Chemistry* 2008, 16, 9804-9816; *Synthetic Communications* 2018, 48, 714-720; and U.S. Pat. No. 5,948,786. Also, the method of Scheme 28 is illustrated in present Example 21, Steps C to E.

Scheme 28

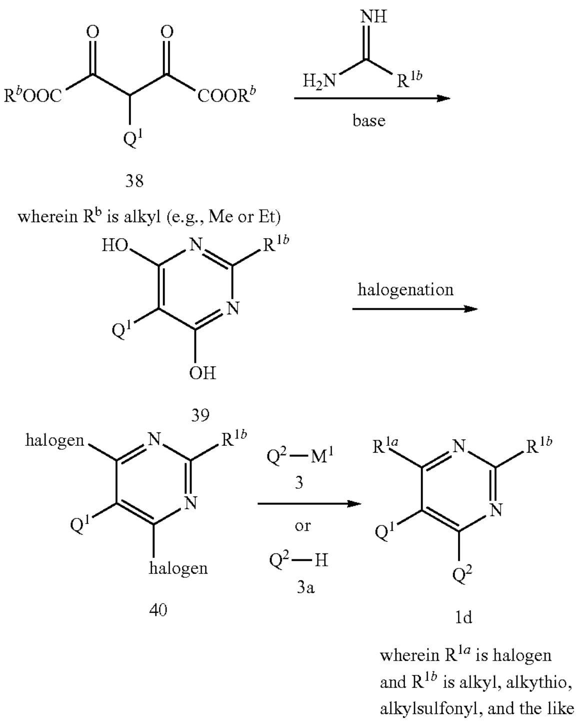

38 wherein $R^b$ is alkyl (e.g., Me or Et)

39

40

1d wherein $R^{1a}$ is halogen and $R^{1b}$ is alkyl, alkythio, alkylsulfonyl, and the like Variations of the synthetic methodology described in Scheme 28 are also useful for preparing compounds of Formula 1d (i.e. Formula 1 wherein J is J-6). For example, as shown in Scheme 29, unsubstituted urea or thiourea can be reacted with derivatives of Formula 38 using reaction conditions analogous to Scheme 28, to provide compounds of Formula 41. Subsequent alkylation, followed by halogenation provides compounds of Formula 43 which are useful intermediates for transition metal-catalyzed cross-coupling reactions to prepare compounds of Formula 1d (i.e. Formula 1 wherein J is J-6). Alkylation is achieved by reacting a compound of Formula 41 with an alkylating agent of formula $R^{1b}$-$X^1$ wherein $X^1$ is a leaving group such as halogen (e.g., Cl, Br or I) or (halo)alkylsulfonate (e.g., p-toluenesulfonate, methanesulfonate or trifluoromethanesulfonate), preferably in the presence of a base such as 1,8-diazabicyclo[5.4.0]undec-7-ene (DBU), potassium carbonate, potassium hydroxide, sodium hydroxide, and in a solvent such as N,N-dimethylformamide, tetrahydrofuran, toluene or water. Subsequent halogenation of Formula 42 compounds can be achieved using a variety of halogenating agents known in the art. For example, dichloropyrimidines of Formula 43 can be prepare by reacting compounds of Formula 42 with a chlorinating agent such as sulfuryl chloride, phosphoric trichloride or phosphorus pentachloride in an appropriate solvent such as carbon tetrachloride, acetonitrile or dichloromethane. Compounds of Formula 43 can be subjected to metal catalyzed cross-coupling reactions analogous to the method of Scheme 1 to provide compounds of Formula 1d (i.e. Formula 1 wherein J is J-6). For references illustrating the method of Scheme 29 see, for example, US 2004116429, and references cited therein.

Scheme 29

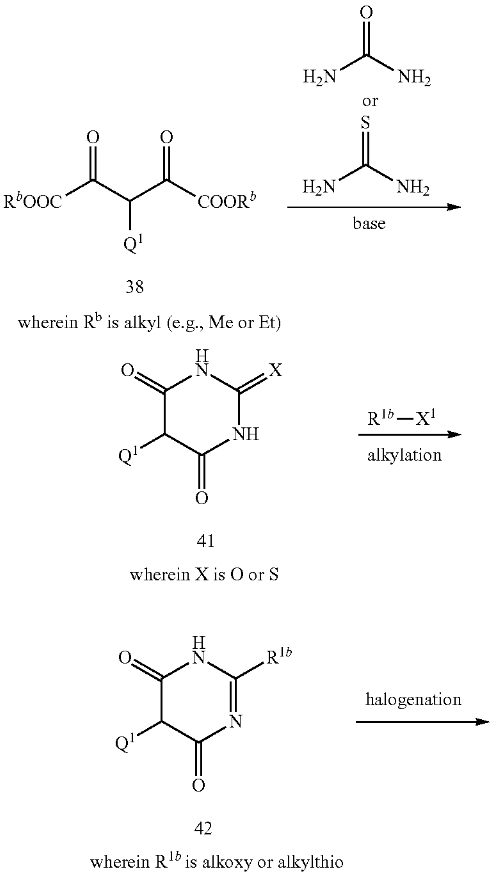

38 wherein $R^b$ is alkyl (e.g., Me or Et)

41 wherein X is O or S

42 wherein $R^{1b}$ is alkoxy or alkylthio

-continued

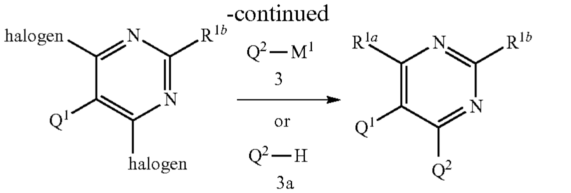

43 wherein X is O or S

1d wherein $R^{1a}$ is halogen or alkyl, and $R^{1b}$ is alkoxy or alkylthio

As shown in Scheme 30, compounds of Formula 38 can be prepared from alkyl acetoacetates of Formula 44 with aryl halides of Formula 45 using metal-catalyzed coupling reaction conditions. A wide variety of metal-catalyzed coupling procedures can be employed in the method of Scheme 30. Particularly useful conditions include copper(I) salts such as copper(I) iodide, L-proline as a ligand, dimethyl sulfoxide as the solvent, and cesium carbonate as the base, at a temperature between about 40 to 50° C. For reaction conditions see, for example, *Organic Letters* 2005, 7(21), 4693-4695.

Scheme 30

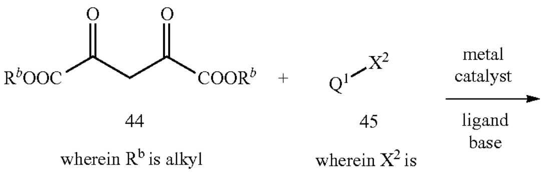

44 wherein $R^b$ is alkyl (e.g., Me or Et)

45 wherein $X^2$ is halogen (preferably B or I)

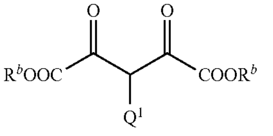

38 wherein $R^b$ is alkyl (e.g., Me or Et)

Alternatively, compounds of Formula 38 can be prepared by esterification of a compound of Formula 46 using an alkyl imidazole carbamate of Formula 47. For reaction conditions, see *Tetrahedron Letters* 2012, 53, 1060-1061. Also, the method of Scheme 31 is illustrated in present Example 21 (Step B).

Scheme 31

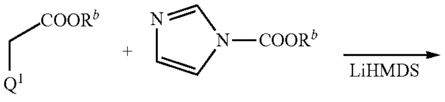

46 47 wherein $R^b$ is alkyl (e.g., Me or Et)

-continued

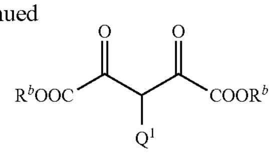

38 wherein $R^b$ is alkyl (e.g., Me or Et)

As shown in Scheme 32, compounds of Formula 1e (i.e. Formula 1 wherein J is J-7) can be prepared analogous to the method of Scheme 1. Present Example 26 (Step E) illustrates the method of Scheme 32.

Scheme 32

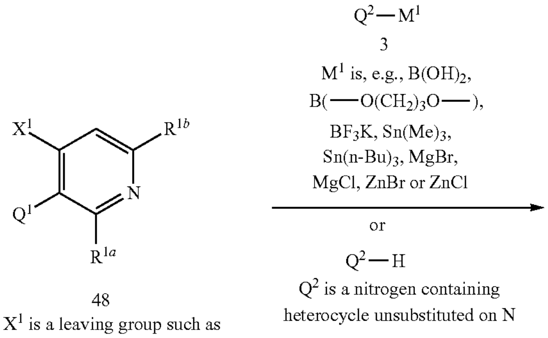

48

$X^1$ is a leaving group such as halogen or (halo)alkylsulfonate

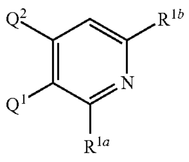

1e

One skilled in the art will recognize that the method of Scheme 32 can be perform when the $X^1$ and $Q^1$ functionalities attached to the compound of Formula 48 are reversed, thus allowing for the introduction of a $Q^1$ ring instead of the $Q^2$ ring.

As shown in Scheme 33, intermediates of Formula 48 are readily prepared from corresponding 4-pyridone derivatives of Formula 49 by treatment with a halogenating or sulfonating agent using standard techniques known in the art. For example, reacting compounds of Formula 49 with phosphorous trichloride, phosphorous pentachloride, phosphorous oxychloride or thionyl chloride in a suitable solvent such as dichloromethane provides compounds of Formula 48 wherein $X^1$ is chlorine. For typical reaction conditions see, for example, *Synthesis* 2006, 17, 2855-2864*; Bioorganic & Medicinal Chemistry Letters* 2005, 15(22), 4998-5002; and WO 2009158257. In some instances, the reaction can be carried out without solvent other than the halogenating agent. Present Example 26 (Step D) illustrates a procedure of preparing a compound of Formula 48 wherein $X^1$ is bromo using phosphoryl bromide as the halogenating agent with no added solvent. Compounds of Formula 48 wherein $X^1$ is (halo)alkylsulfonate can be prepared from corresponding compounds of Formula 49 by reaction with a sulfonating agent such as methanesulfonyl chloride, p-toluenesulfonyl chloride or trifluoromethanesulfonic anhydride, typically in the presence of a base. For reaction conditions see, for example, *Journal of Organic Chemistry* 2020, 85(13), 8339-8351; *Bioorganic & Medicinal Chemistry* 2009, 17, 5433-5441; and *Tetrahedron* 1998, 54, 4405-4412.

Scheme 33

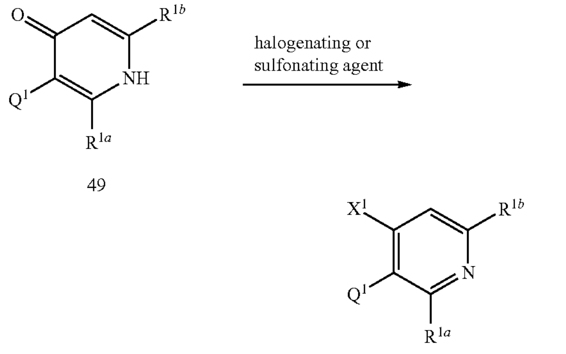

49

48

$X^1$ is a leaving group such as halogen or (halo)alkylsulfonate

As shown in Scheme 34, compounds of Formula 49 can be prepared by condensation of compounds of Formula 50 with aqueous ammonia, e.g., ammonium hydroxide. The reaction is typically performed in an autoclave or in a sealed reaction vessel at temperatures ranging from about 90 to 200° C. For reaction conditions see, for example, Synthesis 2006, 2855-2864; *Journal of Medicinal Chemistry* 2008, 51, 2845-852; and WO 2010/081904. Also, Example 26 (Step C) illustrates the method of Scheme 34.

Scheme 34

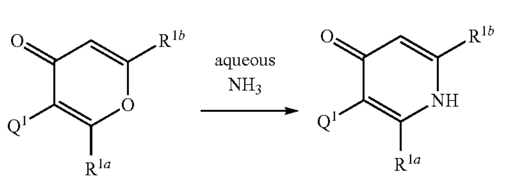

50 49

Compounds of Formula 50 can be prepared by general methods known in the art. For example, as shown in Scheme 35, compounds of Formula 51 can be reacted with compounds of Formula 52 in the presence of polyphosphoric acid or phosphorus pentoxide in methanesulfonic acid (Eaton's reagent). The reaction is typically run at temperatures ranging from about 50 to 80° C. For reaction conditions see *Journal of the American Chemical Society* 1961, 83, 193-198; *Journal of Medicinal Chemistry* 2008, 51, 2845-2852; and WO 2010/081904. Also, the method of Scheme 35 is illustrated in present Example 26 (Step B).

Many compounds of Formula 51 are known and can be prepared by general methods disclosed in the art (e.g., see present Example 26, Step A).

Scheme 35

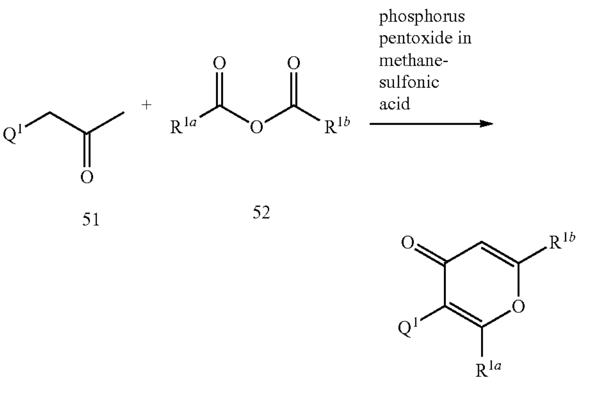

50

As shown in Scheme 36, compounds of Formula if (i.e. Formula 1 wherein J is J-8) can be prepared by reaction of compounds of Formula 53 with alkylating agents of formula $R^3$—$X^1$ wherein $X^1$ is a leaving group such as halogen (e.g., Cl, Br or I) or (halo)alkylsulfonate (e.g., p-toluenesulfonate, methanesulfonate or trifluoromethanesulfonate), preferably in the presence of a base such as 1,8-diazabicyclo[5.4.0]undec-7-ene (DBU), potassium carbonate, potassium hydroxide or sodium hydroxide, and in a solvent such as N,N-dimethylformamide, tetrahydrofuran, toluene or water. A wide range of reaction temperatures are useful in the method of Scheme 36, and one skilled in the art can easily adapt reaction conditions as needed. The method of Scheme 36 is illustrated in present Example 27 (Step E).

Scheme 36

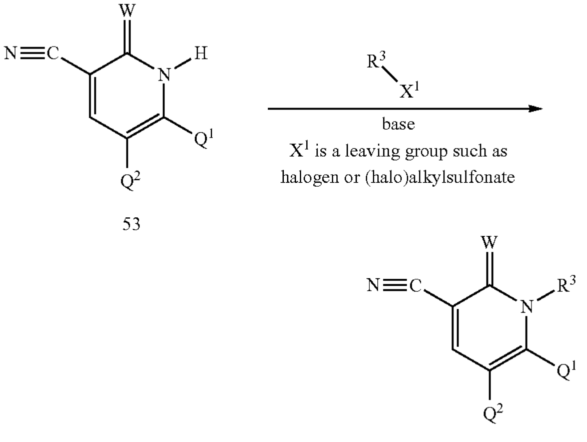

1f wherein $R^4$ is cyano

As shown in Scheme 37, compounds of Formula 53 can be prepared by reaction of compounds of Formula 54 with 2-cyanoacetamide in the presence of a base/solvent combination such as sodium ethoxide in ethanol or potassium tert-butoxide in tert-butanol, at temperatures from about ambient to the boiling point of the solvent. For reaction conditions, see, for example, *Journal of Medicinal Chemistry* 2002, 45(9), 1887-1900. Also, the method of Scheme 37 is illustrated in present Example 27 (Step D).

Scheme 37

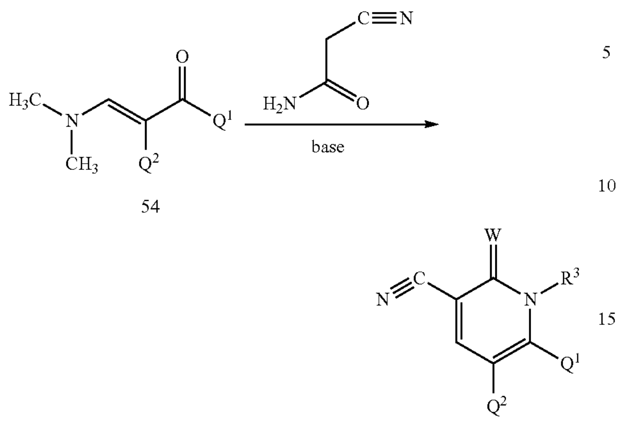

54

53

As shown in Scheme 38, compounds of Formula 54 can be prepared from benzyl phenyl ketone derivatives of Formula 55 by reaction with N,N-dimethylformamide dimethyl acetal, typically in excess of a stoichiometric amount, with the reagent thus also acting as a solvent, or optionally with addition of a co-solvent such as toluene or tetrahydrofuran, and at a temperature from about ambient to the boiling point of the solvent. For reaction conditions, see, for example, *Tetrahedron* 1998, 54, 5075-5088 and *Tetrahedron* 1994, 50, 2255-2264. Also, the method of Scheme 38 is illustrated in present Example 27 (Step C).

Scheme 38

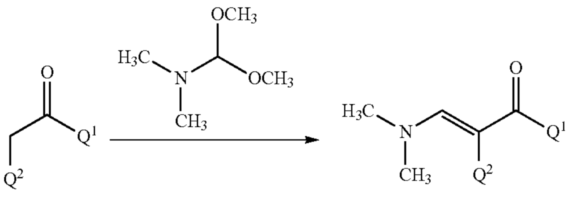

55

54

General methods useful for preparing diaryl ketones of Formula 55 are well-known in the art; see, for example, *Chemical Research in Toxicology* 2011, 24(11), 1853-1861; and *Royal Society of Chemistry* 2017, 7, 11367-11372; and references cited therein. Of particular note is the method illustrated in Scheme 39 below, involving reaction of an acetic acid of Formula 56 with a carboxylic ester of Formula 57. Typically the reaction is run with the aid of a base and in the presence of an inert organic solvent, e.g., with sodium hydride, lithium diisopropylamide or lithium bis(trimethylsilyl)amide (LiHMDS) in a solvent such as benzene, toluene, N,N-dimethylformamide or tetrahydrofuran. The product can be isolated by adjusting the pH to about 1 to 7 and then filtering or extracting, optionally after removal of the organic solvent. Present Example 27 (Step B) illustrates the method of Scheme 39.

Scheme 39

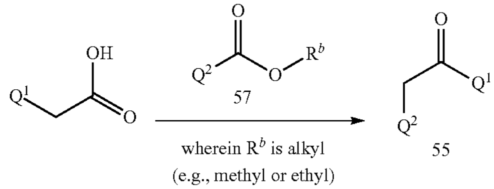

57

56

55

As shown in Scheme 40, compounds of Formula 1g (i.e. Formula 1 wherein J is J-9) can be prepared by condensation of esters of Formula 58 with hydroxylamine or a hydroxylamine salt (e.g., hydroxylamine hydrochloride). The reaction is typically performed in solvents such as methanol, ethanol, water, dichloromethane, and mixtures thereof, at temperatures ranging from 0° C. to the boiling point of the solvent. The addition of a base, often an amine, alkali carbonate, alkali acetate or alkali hydroxide, can be beneficial, particularly when hydroxylamine is used in its salt form. Examples of common bases that can be employed in the reaction are pyridine, triethylamine, sodium acetate, potassium carbonate, sodium carbonate and sodium hydroxide, which can be used in catalytic, stoichiometric, superstoichiometric or solvent quantities. Upon completion of the reaction, the isolated or crude intermediate is treated with acid, such as glacial acetic acid, to provide compounds of Formula 1g. In a preferred method, the intermediate is heated with glacial acetic acid as the solvent to a temperature of about 110° C. Present Example 25 (Step G) illustrates the method of Scheme 40. Compounds of Formula 1g (i.e. Formula 1 wherein J is J-9) may also be synthesized by condensation of hydroxylamine or its salts with 3-hydroxybutenolides followed by ring closure with acid (see US 20120329787), or by reaction of 3-methoxybutenolides with hydroxylamine-O-sulfonic acid (see *Journal of Organic Chemistry* 1987, 52(20), 4521-4526).

Scheme 40

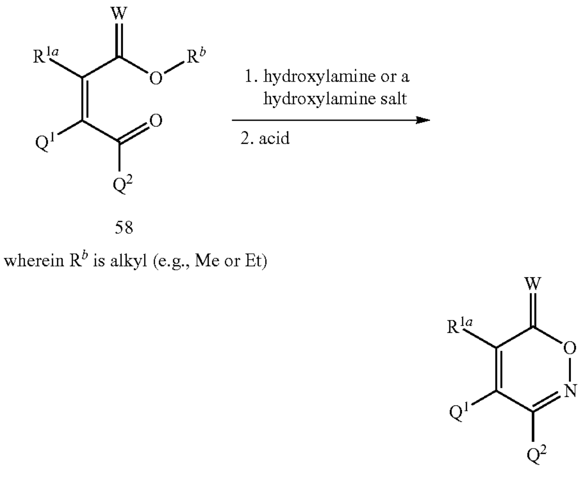

58 wherein $R^b$ is alkyl (e.g., Me or Et)

1g

One skilled in the art will recognize that compounds of Formula 1 can also be subjected to numerous other electrophilic, nucleophilic, radical, organometallic, oxidation and reduction reactions to provide other functionalized compounds of Formula 1. For example, compounds of Formula 1 wherein $R^5$ is halogen can be used to prepare compounds of Formula 1 wherein $R^5$ is alkyl. Compounds of Formula 1, or intermediates for their preparation, may contain aromatic nitro groups, which can be reduced to amino groups, and then converted via reactions well-known in the art (e.g., Sandmeyer reaction) to various halides. By similar known reactions, aromatic halides such as bromides or iodides prepared via the Sandmeyer reaction can react with alcohols under copper-catalyzed conditions, such as the Ullmann reaction or known modifications thereof, to provide compounds of Formula 1 that contain alkoxy substituents. Additionally, some halogen groups, such as fluorine or chlorine, can be displaced with alcohols under basic conditions to provide compounds of Formula 1 containing the corresponding alkoxy substituents. Compounds of Formula 1 or precursors thereof containing a halide, preferably bromide or iodide, are particularly useful intermediates for transition metal-catalyzed cross-coupling reactions to prepare compounds of Formula 1. These types of reactions are well-documented in the literature; see, for example, Tsuji in *Transition Metal Reagents and Catalysts: Innovations in Organic Synthesis*, John Wiley and Sons, Chichester, 2002; *Tsuji in Palladium in Organic Synthesis, Springer,* 2005; and Miyaura and Buchwald in *Cross Coupling Reactions: A Practical Guide,* 2002; and references cited therein.

Compounds of Formula 1 and the intermediates described in above methods wherein W is O can be converted to the corresponding thiolates wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent). Reactions of this type are well-known in the art, see, for example, Heterocycles 1995, 40, 271-278; *Journal of Medicinal Chemistry* 2008, 51, 8124-8134; *Journal of Medicinal Chemistry* 1990, 33, 2697-706; Synthesis 1989, (5), 396-3977; *J. Chem. Soc., Perkin Trans.* 1, 1988, 1663-1668; *Tetrahedron* 1988 44, 3025-3036; and *Journal of Organic Chemistry* 1988 53(6), 1323-1326. Also, for examples relating to pyridazinones, see *Journal of Heterocyclic Chemistry* 1988, 25(6), 1719-23; and *Phosphorus, Sulfur and Silicon and the Related Elements* 2000, 156, 213-223.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after introduction of the reagents depicted in the individual schemes, additional routine synthetic steps not described in detail may be needed to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

Without further elaboration, it is believed that one skilled in the art using the preceding description can utilize the present invention to its fullest extent. The following examples are, therefore, to be construed as merely illustrative, and not limiting of the disclosure in any way whatsoever. Steps in the following examples illustrate a procedure for each step in an overall synthetic transformation, and the starting material for each step may not have necessarily been prepared by a particular preparative run whose procedure is described in other examples or steps. Ambient or room temperature is defined as about 20-25° C. In the following examples, reactions are conducted with stirring under a nitrogen atmosphere, regardless of whether or not it is stated in the example, unless it is explicitly stated otherwise. Percentages are by weight except for chromatographic solvent mixtures or where otherwise indicated. Parts and percentages for chromatographic solvent mixtures are by volume unless otherwise indicated. MPLC refers to medium pressure liquid chromatography on silica gel. $^1$H NMR spectra are reported in ppm downfield from tetramethylsilane; "s" means singlet, "d" means doublet, "t" means triplet, "q" means quartet, "m" means multiplet, "br s" means broad singlet, "dd" means doublet of doublets, "td" means triplet of doublets doublet, "ddd" means doublet of doublets of doublets. $^{19}$F NMR spectra are reported in ppm using trichlorofluoromethane as the reference. Mass spectra are reported as the molecular weight of the highest isotopic abundance of the parent ion (M+1) formed by addition of $H^+$ (molecular weight of 1) to the molecule, or (M−1) formed by the loss of $H^+$ (molecular weight of 1) from the molecule, observed by using liquid chromatography coupled to a mass spectrometer (LCMS) using either atmospheric pressure chemical ionization ($AP^+$) or electrospray ionization ($ESI^+$).

Example 1

Preparation of 5-(2-chloro-4-fluorophenyl)-6-(2-chloro-3-thienyl)-2,4-dimethyl-3(2H)-pyridazinone (Compound 7)

Step A: Preparation of 5,6-dichloro-2-methyl-3(2H)-pyridazinone

A mixture of 5,6-dichloro-3(2H)-pyridazinone (20.0 g, 0.12 mol), iodomethane (31.0 g, 13.6 mL, 0.22 mol) and potassium carbonate (20.1 g, 0.145 mol) in acetonitrile (400 mL) was heated at 100° C. for 16 h. After cooling to room temperature, the reaction mixture was diluted with water and ethyl acetate. The organic layer was separated, dried over magnesium sulfate, filtered and concentrated under reduced pressure to provide the title compound as a solid (20.4 g).

$^1$H NMR ($CDCl_3$): δ 7.09 (s, 1H), 3.74 (s, 3H).

Step B: Preparation of 6-chloro-5-(2-chloro-4-fluorophenyl)-2-methyl-3(2H)-pyridazinone A mixture of 5,6-dichloro-2-methyl-3(2H)-pyridazinone (i.e. the product of Step A) (2.50 g, 14.0 mmol), B-(2-chloro-4-fluorophenyl)boronic acid (2.56 g, 14.7 mmol), sodium carbonate (2 M aqueous solution, 6.15 mL, 12.3 mmol) and dichlorobis(triphenylphosphine) palladium (1.96 g, 2.79 mmol) in 1,4-dioxane (97.7 mL) was heated at 100° C. for 16 h. After cooling to room temperature, the reaction mixture was diluted with water and ethyl acetate. The layers were separated and the aqueous layer was extracted with ethyl acetate. The combined organics were dried over magnesium sulfate, filtered and concentrated under reduced pressure. The resulting material was purified by silica gel column chromatography (eluting with a gradient of 0 to 40% ethyl acetate in hexanes) to provide the title compound as a solid (2.03 g).

$^{1}$H NMR ($CDCl_3$): δ 7.28 (m, 2H), 7.13 (m, 1H), 6.87 (s, 1H), 3.82 (s, 3H).

Step C: Preparation of 6-chloro-5-(2-chloro-4-fluorophenyl)-2,4-dimethyl-3(2H)-pyridazinone A mixture of 6-chloro-5-(2-chloro-4-fluorophenyl)-2-methyl-3(2H)-pyridazinone (i.e. the product of Step B) (2.04 g, 7.47 mmol) in tetrahydrofuran (74.7 mL) was cooled to −20° C., and then methylmagnesium bromide (3.4 M solution in diethyl ether, 8.8 mL, 29.9 mmol) was added dropwise. After 10 minutes, bromine (4.78 g, 29.9 mmol) was added to the reaction mixture. The reaction mixture was allowed to gradually warm to room temperature, and then diluted with water and ethyl acetate. The organic and aqueous layers were separated and the aqueous layer was extracted with ethyl acetate. The combined organics were dried over magnesium sulfate, filtered and concentrated under reduced pressure. The resulting material was purified by silica gel column chromatography (eluting with a gradient of 0 to 40% ethyl acetate in hexanes) to provide the title compound as a solid (1.58 g).

$^{1}$H NMR ($CDCl_3$): δ 7.30 (m, 1H), 7.15 (m, 2H), 3.83 (s, 3H), 1.99 (s, 3H).

Step D: Preparation of 5-(2-chloro-4-fluorophenyl)-6-(2-chloro-3-thienyl)-2,4-dimethyl-3(2H)-pyridazinone A mixture of 6-chloro-5-(2-chloro-4-fluorophenyl)-2,4-dimethyl-3(2H)-pyridazinone (i.e. the product of Step C) (0.30 g, 1.05 mmol), B-(2-chloro-3-thienyl)boronic acid (0.16 g, 0.99 mmol), sodium carbonate (2 M aqueous solution, 0.46 mL, 0.92 mmol) and dichlorobis(triphenylphosphine)palladium (0.15 g, 0.21 mmol) in 1,4-dioxane (7.3 mL) was heated at 100° C. for 16 h. After cooling to room temperature, the reaction mixture was diluted with water and ethyl acetate, the layers were separated and the aqueous layer was extracted with ethyl acetate. The combined organics were dried over magnesium sulfate, filtered and concentrated under reduced pressure. The resulting material was purified by silica gel column chromatography (eluting with a gradient of 0 to 100% ethyl acetate in hexanes) to provide the title compound, a compound of the present invention, as a colorless oil (95 mg).

$^{1}$H NMR ($CDCl_3$): δ 7.13 (dd, 1H), 7.04 (dd, 1H), 6.95 (td, 1H), 6.90 (d, 1H), 6.56 (d, 1H), 3.92 (s, 3H), 2.02 (s, 3H).

LCMS: m/z: 369 $[M+H]^+$

Example 2

Preparation of 4-chloro-5-(2-chloro-4-fluorophenyl)-2-methyl-6-(4-methyl-3-pyridinyl)-3(2H)-pyridazinone (Compound 4)

Step A: Preparation of 4,5-dichloro-2-methyl-3(2H)-pyridazinone

A mixture of 4,5-dichloro-3(2H)-pyridazinone (20.0 g, 0.12 mol), iodomethane (31.0 g, 13.6 mL, 0.22 mol) and potassium carbonate (20.1 g, 0.15 mol) in acetonitrile (400 mL) was heated at 100° C. for 16 h. After cooling to room temperature, the mixture was diluted with water and ethyl acetate. The organic layer was separated, dried over magnesium sulfate, filtered and concentrated under reduced pressure to give the title compound as a solid (19.5 g).

$^{1}$H NMR ($CDCl_3$): δ 7.77 (s, 1H), 3.82 (s, 3H).

Step B: Preparation of 4-chloro-5-iodo-2-methyl-3(2H)-pyridazinone

To a mixture of 4,5-dichloro-2-methyl-3(2H)-pyridazinone (i.e. the product of Step A) (2 g, 11.2 mmol) in N,N-dimethylformamide (20 mL) was added sodium iodide (6.7 g, 44.7 mmol). The reaction mixture was heated at 150° C. for 16 h, and then more sodium iodide (1.68 g, 11.2 mmol) was added. The reaction mixture was maintained at 150° C. for another 6 h, and then more sodium iodide (1.68 g, 11.2 mmol) was added. The reaction mixture was cooled to room temperature and partitioned between water and ethyl acetate. The layers were separated and the aqueous layer was extracted with ethyl acetate. The combined organics were dried over magnesium sulfate, filtered and concentrated under reduced pressure to give the title compound as a solid (1.92 g).

$^{1}$H NMR ($CDCl_3$): δ 7.96 (s, 1H), 3.79 (s, 3H).

Step C: Preparation of 4-chloro-5-(2-chloro-4-fluorophenyl)-2-methyl-3(2H)-pyridazinone A mixture of 4-chloro-5-iodo-2-methyl-3(2H)-pyridazinone (i.e. the product of Step B) (6.03 g, 22.3 mmol), B-(2-chloro-4-fluorophenyl)boronic acid (4.67 g, 26.8 mmol), sodium carbonate (2 M aqueous solution, 20 mL) and dichlorobis(triphenylphosphine)palladium (3.13 g, 4.46 mmol) in 1,4-dioxane (156 mL) was heated at 100° C. for 24 h. The reaction mixture was cooled to room temperature and diluted with water and ethyl acetate. The layers were separated and the aqueous layer was extracted with ethyl acetate. The combined organics were dried over magnesium sulfate, filtered and concentrated under reduced pressure. The resulting material was purified by silica gel column chromatography (eluting with a gradient of 0 to 40% ethyl acetate in hexanes) to provide the title compound as a solid (5.91 g).

$^{1}$H NMR ($CDCl_3$): δ 7.64 (s, 1H), 7.14 (m, 1H) 7.30 (ddd, 2H), 3.9 (s, 3H).

LCMS: m/z: 273 $[M+H]^+$

Step D: Preparation of 4-chloro-5-(2-chloro-4-fluorophenyl)-2-methyl-6-(4-methyl-3-pyridinyl)-3(2H)-pyridazinone To a mixture of 4-chloro-5-(2-chloro-4-fluorophenyl)-2-methyl-3(2H)-pyridazinone (i.e. the product of Step C) (0.1 g, 0.37 mmol) in tetrahydrofuran (8 mL) was added 2,2,6,6-tetramethylpiperidinylzinc chloride lithium chloride complex (CAS No. 1145881-09-9) (0.7 M solution in tetrahydrofuran, 1.0 mL, 0.67 mmol), stirred for 5 minutes, and then added a mixture containing tris(dibenzylideneacetone) dipalladium(0) (34 mg, 0.037 mmol), tri-2-furanylphosphine (17 mg, 0.073 mmol) and 3-iodo-4-methylpyridine (162 mg, 0.74 mmol) and tetrahydrofuran (2 mL). The reaction mixture was stirred for 16 h and then partitioned between water and ethyl acetate. The layers were separated and the aqueous layer was extracted with ethyl acetate. The combined organics were dried over magnesium sulfate, filtered and concentrated under reduced pressure. The resulting material was purified by silica gel column chromatography (eluting with a gradient of 0 to 40% ethyl acetate in hexanes) to provide the title compound, a compound of the present invention, as a solid (89.7 mg).

$^{1}$H NMR ($CDCl_3$): δ 8.32 (d, 1H), 8.16 (s, 1H), 7.07 (m, 3H), 6.95 (m, 1H), 3.95 (s, 3H), 2.25 (s, 3H).

$^{19}$F NMR ($CDCl_3$): δ−108.40.

LCMS: m/z: 364 $[M+H]^+$

Example 3

Preparation of 6-(2-chloro-5-methoxyphenyl)-2,4-dimethyl-5-(4-methyl-3-pyridinyl)-3(2H)-pyridazinone (Compound 21)

Step A: Preparation of 6-chloro-2-methyl-5-(4-methyl-3-pyridinyl)-3(2H)-pyridazinone A mixture of 5,6-dichloro-2-methyl-3(2H)-pyridazinone (prepared by the method of Example 1, Step A) (0.44 g, 2.46 mmol), B-(4-methyl-3-pyridinyl)boronic acid (0.67 g, 4.92 mmol), sodium carbonate (0.78 g, 7.36 mmol) and tetrakis (triphenylphosphine)palladium (0.28 g, 0.25 mmol) in toluene (5.5 mL), ethanol (2.86 mL) and water (2.86 mL) was degassed by bubbling nitrogen gas through the reaction mixture for 30 minutes. The reaction mixture was then heated in a sealed tube at 160° C. for 1.25 h while subjecting to microwave irradiation, then cooled to room temperature and partitioned between water and ethyl acetate. The organics were separated and dried over magnesium sulfate, filtered and concentrated under reduced pressure. The resulting material was purified by silica gel column chromatography (eluting with a gradient of 0 to 100% ethyl acetate in hexanes, and then 20% methanol in ethyl acetate) to provide the title compound as a solid (0.29 g).

$^1$H NMR ($CDCl_3$): δ 8.57 (d, 1H), 8.34 (s, 1H), 7.25 (m, 1H), 6.87 (s, 1H), 3.83 (s, 3H), 2.25 (s, 3H).

Step B: Preparation of 6-(2-chloro-5-methoxyphenyl)-2-methyl-5-(4-methyl-3-pyridinyl)-3(2H)-pyridazinone A mixture of 6-chloro-2-methyl-5-(4-methyl-3-pyridinyl)-3(2H)-pyridazinone (i.e. the product of Step A) (0.29 g, 1.23 mmol), B-(2-chloro-5-methoxyphenyl)boronic acid (0.24 g, 1.29 mmol), sodium carbonate (2 M aqueous solution, 0.54 mL, 1.1 mmol) and dichlorobis-(triphenylphosphine)palladium (0.17 g, 0.24 mmol) in 1,4-dioxane (8.6 mL) was heated at 100° C. for 16 h. The reaction mixture was allowed to cool to room temperature, diluted with water and ethyl acetate, the layers were separated and the aqueous layer was extracted with ethyl acetate. The combined organics were dried over magnesium sulfate, filtered and concentrated under reduced pressure. The resulting material was purified by silica gel column chromatography (eluting with a gradient of 0 to 100% ethyl acetate in hexanes, and then 20% methanol in ethyl acetate) to provide the title compound as a solid (0.13 g).

$^1$H NMR ($CDCl_3$): δ 8.36 (d, 1H), 8.18 (s, 1H), 7.13 (m, 1H), 7.08 (d, 1H), 6.9 (s, 1H), 6.79 (m, 2H), 3.92 (s, 3H), 3.72 (s, 3H), 2.23 (s, 3H).

Step C: Preparation of 6-(2-chloro-5-methoxyphenyl)-2,4-dimethyl-5-(4-methyl-3-pyridinyl)-3(2H)-pyridazinone A mixture of 6-(2-chloro-5-methoxyphenyl)-2-methyl-5-(4-methyl-3-pyridinyl)-3(2H)-pyridazinone (i.e. the product of Step B) (0.13 g, 0.38 mmol) in tetrahydrofuran (3.8 mL) was cooled to −20° C., and then methylmagnesium bromide (3.4 M in diethyl ether, 0.45 mL, 1.52 mmol) was added dropwise. After 10 minutes, bromine (0.24 g, 1.52 mmol) was added dropwise to the reaction mixture. The mixture was allowed to gradually warm to room temperature and diluted with water and ethyl acetate, and the layers were separated and the aqueous layer was extracted with ethyl acetate. The combined organics were dried over magnesium sulfate, filtered and concentrated under reduced pressure. The resulting material was purified by silica gel column chromatography (eluting with a gradient of 0 to 100% ethyl acetate in hexanes, and then 20% methanol in ethyl acetate) to provide the title compound, a compound of the present invention, as a solid (55 mg).

$^1$H NMR ($CDCl_3$): δ 8.6 (m, 2H), 7.73 (m, 1H), 7.13 (m, 1H), 6.82 (m, 2H), 3.94 (s, 3H), 3.80 (s, 3H), 2.46 (s, 3H), 2.01 (s, 3H).

LCMS: m/z: 356 $[M+H]^+$

Example 4

Preparation of 6-(2,4-difluorophenyl)-1-(3,5-dimethoxyphenyl)-1,4-dihydro-5-methyl-4-oxo-3-pyridazinecarboxylic acid (Compound 27)

Step A: Preparation of 2,4-difluoro-N-methoxy-N-methylbenzamide

To a mixture of N,O-dimethylhydroxylamine hydrochloride (60 g, 0.62 mol) in N,N-dimethylformamide (600 mL) at 0° C. was added triethylamine (62 g, 0.61 mol), followed by 1-(3-dimethylaminopropyl)-3-ethylcarbodiimide hydrochloride (EDC) (120 g, 0.63 mol). After stirring for 15 minutes at 0° C., 2,4-difluorobenzoyl chloride (100 g, 0.57 mol) in N,N-dimethylformamide (1 L) was added dropwise to the reaction mixture. After 10 minutes, the reaction mixture was allowed to warm to room temperature and stirred for 10 h. The mixture was diluted with ethyl acetate (1.5 L) and water (2 L), the layers were separated and the organic layer was washed with saturated aqueous sodium bicarbonate solution (1 L), dried over sodium sulfate, filtered and concentrated under reduced pressure. The resulting material was purified by silica gel column chromatography (eluting with 20% ethyl acetate in petroleum ether) to provide the title compound as a colorless oil (75 g).

$^1$H NMR ($CDCl_3$): δ 7.48-7.42 (m, 1H), 6.96-6.91 (m, 1H), 6.88-6.83 (m, 1H), 3.56 (br s, 3H), 3.34 (br s, 3H).

LCMS: m/z: 202 $[M+H]^+$

Step B: Preparation of ethyl 2,4-difluoro-7-methyl-3,6-dioxobenzenepentanoate

To a solution of tetrahydrofuran (400 mL) at 0° C. was added portionwise sodium hydride (60% in oil, 11 g, 0.46 mol), followed by ethyl 3-oxopentanoate (40 g, 0.28 mol). After 10 minutes, lithium diisopropylamide (LDA) (2 M in tetrahydrofuran, 138 mL, 0.28 mol) was added to the reaction mixture. The reaction mixture was stirred for 40 minutes at 0° C., and then 2,4-difluoro-N-methoxy-N-methylbenzamide (i.e. the product of Step A) (55 g, 0.27 mol) in tetrahydrofuran (275 mL) was added. The reaction mixture was stirred at room temperature for 18 h, and then cooled to 0° C. and acidified to pH 2 by adding hydrochloric acid (1 N aqueous solution). The resulting mixture was extracted with ethyl acetate (3×600 mL), dried over sodium sulfate, filtered and concentrated under reduced pressure. The resulting material was purified by silica gel column chromatography (eluting with 5% ethyl acetate in petroleum ether) to provide the title compound as a solid (45 g).

LCMS: m/z: 285 $[M+H]^+$

Step C: Preparation of 6-(2,4-difluorophenyl)-4-hydroxy-5-methyl-2H-pyran-2-one

To a solution of ethyl 2,4-difluoro-7-methyl-3,6-dioxobenzenepentanoate (i.e. the product of Step B) (88 g, 0.31 mol) at 0° C. was added concentrated sulfuric acid (528 mL) dropwise. The reaction mixture was allowed to warm to room temperature, stirred for 10 h and then diluted with ice-cold water (1 L). The resulting solid precipitate was collected by filtration, washed with diethyl ether (100 mL) and acetone (100 mL) to provide the title compound as a pala-brown solid (50 g).

$^1$H NMR (DMSO-$d_6$): δ 12.17 (s, 1H), 7.67-7.61 (q, 1H), 7.49-7.43 (m, 1H), 7.28-7.23 (m, 1H), 5.49 (s, 1H), 1.76 (s, 3H).

LCMS: m/z: 239 $[M+H]^+$

Step D: Preparation of (3E)-6-(2,4-difluorophenyl)-5-methyl-2H-pyran-2,3,4-trione 3-[2-(3,5-dimethoxyphenyl)hydrazone]

To a mixture of 3,5-dimethoxybenzenamine (9.6 g, 62.7 mmol) in acetic acid (18 mL) at 0° C. was added concentrated hydrochloric acid (76.8 mL) and sodium nitrite (4.3 g, 62.3 mmol) in water (86 mL). The reaction mixture was stirred at 0° C. for 2 h.

In a separate reaction flask, a mixture of 6-(2,4-difluorophenyl)-4-hydroxy-5-methyl-2H-pyran-2-one (i.e. the product of Step C) (15 g, 63.0 mmol) and sodium carbonate (92 g, 0.87 mol) in water/tetrahydrofuran (600 mL, 1:1 solution) was stirred for 30 minutes, cooled to 0° C., and then the above reaction mixture was added dropwise over 40 minutes. The reaction mixture was allowed to warm to room temperature and stirred for 2 h. The resulting solid precipitate was collected by filtration, washed with n-pentane (50 mL) and diethyl ether (50 mL) to provide the title compound as a pala-brown solid (21 g).

$^1$H NMR (DMSO-$d_6$): δ 7.66 (br s, 1H), 7.46 (br s, 1H), 7.27 (br s, 1H), 6.85 (br s, 2H), 6.43 (br s, 1H), 3.79 (s, 6H), 1.71 (s, 3H).

LCMS: m/z: 403 $[M+H]^+$

Step E: Preparation of 6-(2,4-difluorophenyl)-1-(3,5-dimethoxyphenyl)-1,4-dihydro-5-methyl-4-oxo-3-pyridazinecarboxylic Acid A mixture of (3E)-6-(2,4-difluorophenyl)-5-methyl-2H-pyran-2,3,4-trione 3-[2-(3,5-dimethoxyphenyl)hydrazone] (i.e. the product of Step D) (20 g, 49.7 mmol) and concentrated hydrochloric acid (400 mL) was heated at 100° C. for 4 h. The reaction mixture was cooled to 0° C. and then diluted with water (500 mL) and the resulting solid precipitate was collected by filtration, rinsing with diethyl ether (100 mL), to provide the title compound, a compound of the present invention, as a solid (13 g).

$^1$H NMR (DMSO-$d_6$): δ 15.73 (br s, 1H), 7.72 (q, 1H), 7.51 (t, 1H), 7.32 (t, 1H), 6.95-6.94 (t, 2H), 6.50 (d, 1H), 3.81 (s, 6H) 1.71 (s, 3H).

LCMS: m/z: 403 $[M+H]^+$

Example 5

Preparation of ethyl 6-(2,4-difluorophenyl)-1-(3,5-dimethoxyphenyl)-1,4-dihydro-5-methyl-4-oxo-3-pyridazinecarboxylate (Compound 28)

To a mixture of 6-(2,4-difluorophenyl)-1-(3,5-dimethoxyphenyl)-1,4-dihydro-5-methyl-4-oxo-3-pyridazinecarboxylic acid (i.e. the product of Example 4, Step E) (5 g, 12.4 mmol) in ethanol (50 mL) at 0° C. was added thionyl chloride (4.4 g, 37 mmol). The reaction mixture was stirred for 10 minutes, and then heated at 90° C. for 12 h. The reaction mixture was diluted with water (50 mL) and extracted with ethyl acetate (2×50 mL). The combined organic extracts were washed with saturated aqueous sodium chloride solution, dried over sodium sulfate, filtered and concentrated under reduced pressure to provide the title compound, a compound of the present invention, as an off-white solid (4 g).

$^1$H NMR (DMSO-$d_6$): δ 7.62-7.58 (q, 1H), 7.37-7.33 (t, 1H), 7.18-7.14 (t, 1H), 6.55 (m, 2H), 6.46-6.45 (m, 1H), 4.34 4.30 (q, 2H), 3.65 (s, 6H), 1.75 (s, 3H), 1.30-1.27 (t, 3H).

LCMS: m/z: 431 $[M+H]^+$

Example 6

Preparation of 6-(2,4-difluorophenyl)-1-(3,5-dimethoxyphenyl)-3-(hydroxymethyl)-5-methyl-4(1H)-pyridazinone (Compound 23)

To a mixture of ethyl 6-(2,4-difluorophenyl)-1-(3,5-dimethoxyphenyl)-1,4-dihydro-5-methyl-4-oxo-3-pyridazinecarboxylate (i.e. the product of Example 5) (2.8 g, 6.5 mmol) in ethanol (28 mL) at 0° C. was added sodium borohydride (508 mg, 13.42 mmol). The reaction mixture was stirred for 10 minutes at 0° C., and then allowed to warm to room temperature and stirred for 18 h. The reaction mixture was diluted with ethyl acetate (100 mL) and water (50 mL), the organic layer was separated and washed with saturated aqueous sodium chloride solution (100 mL), dried over sodium sulfate, filtered and concentrated under reduced pressure. The resulting material was purified by column chromatography (eluting with 10% ethyl acetate in petroleum ether) to provide the title compound, a compound of the present invention, as a pale-brown solid (1.6 g).

$^1$H NMR (DMSO-$d_6$): δ 7.61-7.56 (q, 1H), 7.36-7.31 (t, 1H), 7.17-7.13 (t, 1H), 6.48-6.44 (dd, 3H), 5.06-5.03 (t, 1H), 4.58-4.49 (d, 2H), 3.60 (s, 6H), 1.72 (s, 3H).

LCMS: m/z: 389 $[M+H]^+$

Example 7

Preparation of 1-(2-chloro-3,5-dimethoxyphenyl)-6-(2,4-difluorophenyl)-3-(hydroxymethyl)-5-methyl-4(1H)-pyridazinone (Compound 30) and 1-(4-chloro-3,5-dimethoxyphenyl)-6-(2,4-difluorophenyl)-3-(hydroxymethyl)-5-methyl-4(1H)-pyridazinone (Compound 32)

To a mixture of 6-(2,4-difluorophenyl)-1-(3,5-dimethoxyphenyl)-3-(hydroxymethyl)-5-methyl-4(1H)-pyridazinone (i.e. the product of Example 6) (2 g, 5.15 mmol) in acetonitrile (50 mL) was added N-chlorosuccinimide (685 mg, 5.15 mmol). The reaction mixture was stirred for 10 minutes at room temperature, and then heated at 80° C. for 12 h. The reaction mixture was cooled to room temperature and diluted with water (50 mL). The resulting mixture was extracted with ethyl acetate (3×50 mL) and the combined extracts were washed with saturated aqueous sodium chloride solution, dried over sodium sulfate, filtered and concentrated under reduced pressure. The resulting material was purified by preparative HPLC (X-Bridge C18 (150×30 mm), 5μμm mobile phase A: 10 mM ammonium acetate (aqueous solution), B: acetonitrile, to provide the title compounds, compounds of the present invention. Compound Number 30 was obtained as an off-white solid (600 mg) and Compound Number 32 was obtained as an off-white solid (180 mg).

$^1$H NMR ($CDCl_3$): δ 7.31-7.26 (m, 1H), 6.86-6.76 (m, 2H), 6.49-6.44 (dd, 2H), 4.88-4.74 (m, 2H), 3.85-3.82 (m, 4H), 3.76-3.73 (d, 3H) 1.87 (s, 3H).

LCMS: m/z: 423 $[M+H]^+$ $^1$H NMR ($CDCl_3$): δ 7.08-7.06 (m, 1H), 6.90-6.82 (m, 2H), 6.42 (s, 2H), 4.81 (t, 2H), 3.78 (s, 7H), 1.90 (s, 3H).

LCMS: m/z: 423 $[M+H]^+$

Example 8

Preparation of 1-(2-chloro-3,5-dimethoxyphenyl)-6-(2,4-difluorophenyl)-3,5-dimethyl-4(1H)-pyridazinone (Compound 33)

Step A: Preparation of 1-(2-chloro-3,5-dimethoxyphenyl)-6-(2,4-difluorophenyl)-5-methyl-3-[[(methylsulfonyl)oxy]methyl]-4(1H)-pyridazinone To a mixture of 1-(2-chloro-3,5-dimethoxyphenyl)-6-(2,4-difluorophenyl)-3-(hydroxymethyl)-5-methyl-4(1H)-pyridazinone (i.e. the product of Example 7, cmpd. no. 30) (400 mg, 0.95 mmol) in dichloromethane (4 mL) at 0° C. was added methanesulfonyl chloride (108 mg, 0.94 mmol) and triethylamine (105 mg, 1.04 mmol). The reaction mixture was stirred at 0° C. for 10 minutes and then at room temperature for 2 h. The reaction mixture was concentrated under reduced pressure and the resulting material was diluted with water (50 mL) and extracted with ethyl acetate (2×20 mL). The combined extracts were dried over sodium sulfate, filtered and concentrated under reduced pressure to provide the title compound as a pale-yellow solid.

Step B: Preparation of 1-(2-chloro-3,5-dimethoxyphenyl)-6-(2,4-difluorophenyl)-3,5-dimethyl-4(1H)-pyridazinone To a mixture of 1-(2-chloro-3,5-dimethoxyphenyl)-6-(2,4-difluorophenyl)-5-methyl-3-[[(methylsulfonyl)oxy]methyl]-4(1H)-pyridazinone (i.e. the product of Step A) (500 mg, 1.0 mmol) in dimethyl sulfoxide (5 mL) at 0° C. was added sodium borohydride (75 mg, 1.98 mmol). The reaction mixture was allowed to warm to room temperature and stirred for 2 h, and then diluted with water (20 mL). The resulting solid precipitate was collected by filtration, and rinsed with diethyl ether (10 mL), to provide the title compound, a compound of the present invention, as an off-white solid (190 mg).

$^1$H NMR (DMSO-$d_6$): δ 7.67-7.31 (m, 2H), 7.15-7.10 (m, 1H), 7.00-6.62 (m, 2H), 3.80 (d, 3H), 3.72 (s, 3H), 2.25 (d, 3H), 1.72 (d, 3H).

LCMS: m/z: 407 $[M+H]^+$

Example 9

Preparation of 6-(2-chloro-4-fluorophenyl)-1-(3,5-dimethoxyphenyl)-3-methyl-2,4(1H,3H)-pyrimidinedione (Compound 34)

Step A: Preparation of phenyl N-(3,5-dimethoxyphenyl)carbamate

To a mixture of 3,5-dimethoxybenzenamine (25 g, 0.16 mol) in dichloromethane (100 mL) was added triethylamine (34.1 mL, 0.24 mol), followed by phenyl chloroformate (38.2 mL, 0.30 mol). The reaction mixture was stirred at room temperature for 16 h, and then diluted with water (300 mL) and extracted with dichloromethane (3×200 mL). The combined organic extracts were dried over sodium sulfate, filtered and concentrated under reduced pressure. The resulting material was purified by silica gel column chromatography (eluting with 40% ethyl acetate in hexanes) to provide the title compound as a white solid (19.6 g).

$^1$H NMR (DMSO-$d_6$): δ 10.17 (s, 1H), 7.42 (t, 2H), 7.28-7.20 (m, 3H), 6.74 (d, 2H), 6.22 (t, 1H), 3.70 (s, 6H).

Step B: Preparation of N-(3,5-dimethoxyphenyl)-N'-methylurea

To a mixture of phenyl N-(3,5-dimethoxyphenyl)carbamate (i.e. the product of Step A) (19 g, 69.5 mmol) in tetrahydrofuran (200 mL) was added methylamine (2 M in tetrahydrofuran, 51.28 mL, 0.28 mol). The reaction mixture was stirred at room temperature for 16 h and then concentrated under reduced pressure. The resulting mixture was diluted with water (200 mL) and extracted with ethyl acetate (3×200 mL). The combined organic extracts were dried over sodium sulfate, filtered and concentrated under reduced pressure. The resulting material was purified by silica gel column chromatography (eluting with 40% ethyl acetate in hexanes) to provide the title compound as a white solid (12 g).

$^1$H NMR (DMSO-$d_6$): δ 8.48 (s, 1H), 6.22 (d, 2H), 6.04 (d, 1H), 5.59 (d, 1H), 3.67 (s, 6H), 2.61 (d, 3H).

Step C: Preparation of 1-(3,5-dimethoxyphenyl)-3-methyl-2,4,6(1H,3H,5H)-pyrimidinetrione To a mixture of N-(3,5-dimethoxyphenyl)-N'-methylurea (i.e. the product of Step B) (12 g, 57.1 mmol) in dichloromethane (150 mL) at 0° C. was added propanedioyl dichloride (5.59 mL, 57.5 mmol). The reaction mixture was stirred for 2 h at room temperature, and then diluted with water (150 mL) and extracted with ethyl acetate (3×150 mL). The combined organic extracts were dried over sodium sulfate, filtered and concentrated under reduced pressure to provide the title compound as a yellow oil (13.50 g).

$^1$H NMR ($CDCl_3$): δ 6.54 (d, 1H), 6.34 (d, 2H), 3.85 (s, 2H), 3.78 (s, 6H), 3.36 (s, 3H).

Step D: Preparation of 6-chloro-1-(3,5-dimethoxyphenyl)-3-methyl-2,4(1H,3H)-pyrimidinedione To a solution of phosphoric trichloride (35 mL, 0.38 mol) at 0° C. was added 1-(3,5-di methoxyphenyl)-3-methyl-2,4,6(1H,3H,5H)-pyrimidinetrione (i.e. the product of Step C) (6.5 g, 23.4 mmol). The reaction mixture was heated at 100° C. for 6 h and then concentrated under reduced pressure. The resulting mixture was diluted with ice-cold water (300 mL) and extracted with ethyl acetate (3×200 mL). The combined organic extracts were dried over sodium sulfate, filtered and concentrated under reduced pressure. The resulting material was purified by silica gel column chromatography (eluting with 30% ethyl acetate in hexanes) to provide the title compound as a white solid (2.1 g).

$^1$H NMR ($CDCl_3$): δ 6.58 (t, 1H), 6.39 (d, 2H), 6.03 (s, 1H), 3.80 (s, 6H), 3.36 (s, 3H).

Step E: Preparation of 6-(2-chloro-4-fluorophenyl)-1-(3,5-dimethoxyphenyl)-3-methyl-2,4(1H,3H)-pyrimidinedione To a mixture of 6-chloro-1-(3,5-dimethoxyphenyl)-3-methyl-2,4(1H,3H)-pyrimidinedione (i.e. the product of Step D) (4 g, 13.5 mmol) in 1,4-dioxane (40 mL) and water (4 mL) was added B-(2-chloro-4-fluorophenyl)boronic acid (3.50 g, 20.1 mmol) followed by cesium carbonate (13.2 g, 40.5 mmol). The reaction mixture was degassed by bubbling argon gas through the reaction for 10 minutes, and then tetrakis(triphenylphosphine)palladium (3.12 g, 2.7 mmol) was added. The reaction mixture was again degassed by bubbling argon gas through the reaction for 5 minutes, and then heated in a sealed tube at 100° C. for 24 h. The reaction mixture was filtered through a pad of Celite®, the filtrate was diluted with water (100 mL) and extracted with ethyl acetate (3×150 mL). The combined organic extracts were dried over sodium sulfate, filtered and concentrated under reduced pressure. The resulting material was purified by silica gel column chromatography (eluting with 60% ethyl acetate in hexanes) to provide the title compound, a compound of the present invention, as a light-yellow solid (1.8 g).

$^1$H NMR ($CDCl_3$): δ 7.26-7.10 (m, 1H), 7.05 (dd, 1H), 6.90-6.85 (m, 1H), 6.44 (br s, 1H), 6.31 (s, 1H), 6.21 (br s, 1H), 5.79 (s, 1H), 3.69 (s, 6H), 3.44 (s, 3H).

Example 10

Preparation of 5-chloro-1-(2-chloro-3,5-dimethoxyphenyl)-6-(2-chloro-4-fluorophenyl)-3-methyl-2,4(1H,3H)-pyrimidinedione (Compound 35) and 1-(2-chloro-3,5-dimethoxyphenyl)-6-(2-chloro-4-fluorophenyl)-3-methyl-2,4(1H,3H)-pyrimidinedione (Compound 36)

To a mixture of 6-(2-chloro-4-fluorophenyl)-1-(3,5-dimethoxyphenyl)-3-methyl-2,4(1H,3H)-pyrimidinedione (i.e. the product of Example 9, Step E) (500 mg, 1.28 mmol) in N,N-dimethylformamide (5 mL) was added N-chlorosuccinimide (343 mg, 2.57 mmol). The reaction mixture was heated in a sealed tube at 80° C. for 1 h while subjecting to microwave irradiation. The reaction mixture was concentrated under reduced pressure, diluted with water (10 mL) and extracted with ethyl acetate (3×50 mL). The combined organic extracts were dried over sodium sulfate, filtered and concentrated under reduced pressure. The resulting material was purified by silica gel column chromatography (eluting with 30% ethyl acetate in hexanes) to provide the title compounds, compounds of the present invention. Compound Number 35 was obtained as a white solid (150 mg) and Compound Number 36 was obtained as a white solid (125 mg).

$^1$H NMR ($CDCl_3$): δ 7.30-7.28 (m, 1H), 7.11 (dd, 1H), 6.92-6.87 (m, 1H), 6.54 (d, 1H), 6.41 (d, 1H), 3.81 (s, 3H), 3.70 (s, 3H), 3.52 (s, 3H).

$^1$H NMR ($CDCl_3$): δ 7.33-7.30 (m, 1H), 7.05-7.03 (dd, 1H), 6.88-6.83 (m, 1H), 6.58 (d, 1H), 6.40 (d, 1H), 5.81 (s, 1H), 3.80 (s, 3H), 3.70 (s, 3H), 3.45 (s, 3H).

Example 11

Preparation of 5-chloro-6-(2-chloro-4-fluorophenyl)-1-(3,5-dimethoxyphenyl)-3-methyl-2,4(1H,3H)-pyrimidinedione (Compound 38) and 1-(2-chloro-3,5-dimethoxyphenyl)-6-(2-chloro-4-fluorophenyl)-3-methyl-2,4(1H,3H)-pyrimidinedione (Compound 36)

To a mixture of 6-(2-chloro-4-fluorophenyl)-1-(3,5-dimethoxyphenyl)-3-methyl-2,4(1H,3H)-pyrimidinedione (i.e. the product of Example 9, Step E) (300 mg, 0.768 mmol) in N,N-dimethylformamide (3 mL) was added N-chlorosuccinimide (103 mg, 0.77 mmol). The reaction mixture was heated in a sealed tube at 80° C. for 2 h while subjecting to microwave irradiation. The reaction mixture was diluted with water (10 mL) and extracted with ethyl acetate (3×50 mL). The combined organic extracts were dried over sodium sulfate, filtered and concentrated under reduced pressure. The resulting material was purified by silica gel column chromatography (eluting with 30% ethyl acetate in hexanes) to provide the title compounds, compounds of the present invention. Compound Number 38 was obtained as a white solid (30 mg) and Compound Number 36 was obtained as a white solid (90 mg).

$^1$H NMR ($CDCl_3$): δ 7.09-7.05 (m, 2H), 6.93-6.89 (m, 1H), 6.41 (d, 1H), 6.31 (t, 1H), 6.25 (d, 1H), 3.64 (s, 3H), 3.63 (s, 3H), 3.38 (s, 3H).

$^1$H NMR ($CDCl_3$): δ 7.33-7.30 (m, 1H), 7.05-7.03 (dd, 1H), 6.88-6.83 (m, 1H), 6.58 (d, 1H), 6.40 (d, 1H), 5.81 (s, 1H), 3.80 (s, 3H), 3.70 (s, 3H), 3.45 (s, 3H).

Example 12

Preparation of 6-(2-chloro-4-fluorophenyl)-1-(3,5-dimethoxyphenyl)-3,5-dimethyl-2,4(1H,3H)-pyrimidinedione (Compound 39)

Step A: Preparation of phenyl N-(3,5-dimethoxyphenyl)carbamate

To a mixture of 3,5-dimethoxybenzenamine (25 g, 0.16 mol) in dichloromethane (100 mL) was added triethylamine (34.1 mL, 0.24 mol), followed by phenyl chloroformate (38.2 mL, 0.30 mol). The reaction mixture was stirred at room temperature for 16 h, and then diluted with water (300 mL) and extracted with dichloromethane (3×200 mL). The combined organic extracts were dried over sodium sulfate, filtered and concentrated under reduced pressure. The resulting material was purified by silica gel column chromatography (eluting with 40% ethyl acetate in hexanes) to provide the title compound as a white solid (19.6 g).

$^1$H NMR (DMSO-$d_6$): δ 10.17 (s, 1H), 7.42 (t, 2H), 7.28-7.20 (m, 3H), 6.74 (d, 2H), 6.22 (t, 1H), 3.70 (s, 6H).

Step B: Preparation of N-(3,5-dimethoxyphenyl)-N'-methylurea

To a mixture of phenyl N-(3,5-dimethoxyphenyl)carbamate (i.e. the product of Step A) (19 g, 69.5 mmol) in tetrahydrofuran (200 mL) was added methylamine (2 M in tetrahydrofuran, 51.28 mL, 0.28 mol). The reaction mixture was stirred at room temperature for 16 h and then concentrated under reduced pressure. The resulting mixture was diluted with water (200 mL) and extracted with ethyl acetate (3×200 mL). The combined organic extracts were dried over sodium sulfate, filtered and concentrated under reduced pressure. The resulting material was purified by silica gel column chromatography (eluting with 40% ethyl acetate in hexanes) to provide the title compound as a white solid (12 g).

$^1$H NMR (DMSO-$d_6$): δ 8.48 (s, 1H), 6.22 (d, 2H), 6.04 (d, 1H), 5.59 (d, 1H), 3.67 (s, 6H), 2.61 (d, 3H).

Step C: Preparation of 1-(3,5-dimethoxyphenyl)-3,5-dimethyl-2,4,6(1H,3H,5H)-pyrimidinetrione To a mixture of N-(3,5-dimethoxyphenyl)-N-methylurea (i.e. the product of Step B) (3.0 g, 14.27 mmol) in acetic anhydride (9 mL) at 0° C. was added 2-methylpropanedioic acid (1.68 g, 14.23 mmol). The reaction mixture was heated at 80° C. for 2 h and then concentrated under reduced pressure. The resulting material was diluted with saturated aqueous sodium hydrogen carbonate solution (50 mL) and washed with ethyl acetate (2×10 mL). The aqueous layer was acidified with concentrated hydrochloric acid and extracted with ethyl acetate (3×100 mL). The combined organic extracts were dried over sodium sulfate, filtered and concentrated under reduce pressure. To the resulting material was added methanol (15 mL) and sodium hydroxide (2 M aqueous solution, 9 mL) and the reaction mixture was heated at 70° C. for 6 h. The reaction mixture was concentrated under reduced pressure and hydrochloric acid (1 M aqueous solution) was added to bring the pH to 6. The resulting mixture was extracted with ethyl acetate (3×100 mL), and the combined organic extracts were dried over sodium sulfate, filtered and concentrated under reduce pressure to provide the title compound as an oil (3 g).

Step D: Preparation of 6-chloro-1-(3,5-dimethoxyphenyl)-3,5-dimethyl-2,4(1H,3H)-pyrimidinedione To a solution of phosphoric trichloride (15.7 mL, 0.17 mol) at 0° C. was added 1-(3,5-dimethoxyphenyl)-3,5-dimethyl-2,4,6(1H,3H,5H)-pyrimidinetrione (i.e. the product of Step C) (3.0 g, 10.26 mmol). The reaction mixture was heated at 100° C. for 16 h, and then concentrated under reduced pressure and diluted with ice-cold water (100 mL). The resulting mixture was extracted with ethyl acetate (3×100 mL) and the combined organic extracts were dried over sodium sulfate, filtered and concentrated under reduced pressure. The resulting material was purified by silica gel column chromatography (eluting with 60% ethyl acetate in hexanes) to provide the title compound as a white solid (1 g).

$^1$H NMR ($CDCl_3$): δ 6.55 (s, 1H), 6.39 (d, 2H), 3.80 (s, 6H), 3.39 (s, 3H), 2.12 (s, 3H).

Step E: Preparation of 6-(2-chloro-4-fluorophenyl)-1-(3,5-dimethoxyphenyl)-3,5-dimethyl-2,4(1H,3H)-pyrimidinedione To a mixture of 6-chloro-1-(3,5-dimethoxyphenyl)-3,5-dimethyl-2,4(1H,3H)-pyrimidinedione (i.e. the product of Step D) (900 mg, 2.9 mmol) in 1,4-dioxane (9 mL) and water (1 mL) was added B-(2-chloro-4-fluorophenyl)boronic acid (0.78 g, 4.44 mmol) and cesium carbonate (2.16 g, 6.63 mmol). The reaction mixture was degassed by bubbling argon gas through the reaction for 10 minutes, and then tetrakis(triphenylphosphine)palladium (1.02 g, 0.89 mmol) was added. The reaction mixture was again degassed by bubbling argon gas through the reaction for 5 minutes, and then heated in a sealed tube at 120° C. for 2 h while subjecting to microwave irradiation. The reaction mixture was filtered through a pad of Celite® and the filtrate was diluted with water (50 mL) and extracted with ethyl acetate (3×50 mL). The combined organic extracts were dried over sodium sulfate, filtered and concentrated under reduced pressure. The resulting material was purified by silica gel column chromatography (eluting with 50% ethyl acetate in hexanes) to provide the title compound, a compound of the present invention, as a white solid (550 mg).

$^1$H NMR ($CDCl_3$): δ 7.13-7.01 (m, 2H), 6.90-6.85 (m, 1H), 6.49-6.46 (m, 1H), 6.29-6.24 (m, 2H), 3.69 (s, 3H), 3.67 (s, 3H), 3.47 (s, 3H), 1.72 (s, 3H).

Example 13

Preparation of 1-(2-chloro-3,5-dimethoxyphenyl)-6-(2-chloro-4-fluorophenyl)-3,5-dimethyl-2,4(1H,3H)-pyrimidinedione (Compound 37)

To a mixture of 6-(2-chloro-4-fluorophenyl)-1-(3,5-dimethoxyphenyl)-3,5-dimethyl-2,4(1H,3H)-pyrimidinedione (i.e. the product of Example 12, Step E) (500 mg, 1.24 mmol) in tetrahydrofuran (5 mL) was added N-chlorosuccinimide (269 mg, 2.01 mmol). The reaction mixture was heated in a sealed tube at 100° C. for 2 h while subjecting to microwave irradiation, and then concentrated under reduced pressure. The resulting material was diluted with water (20 mL) and extracted with ethyl acetate (3×50 mL). The combined organic extracts were dried over sodium sulfate, filtered and concentrated under reduced pressure. The resulting material was purified by silica gel column chromatography (eluting with 60% ethyl acetate in hexanes) to provide the title compound, a compound of the present invention, as a white solid (360 mg).

$^1$H NMR ($CDCl_3$): δ 7.26-7.23 (m, 1H), 7.08 (dd, 1H), 6.89-6.84 (m, 1H), 6.52 (d, 1H), 6.38 (d, 1H), 3.80 (s, 3H), 3.68 (s, 3H), 3.48 (s, 3H), 1.72 (s, 3H).

Example 14

Preparation of 5-(2-chloro-4-fluorophenyl)-4-(3,5-dimethoxyphenyl)-2,6-dimethylpyrimidine (Compound 44)

Step A: Preparation of 4-chloro-5-(2-chloro-4-fluorophenyl)-2,6-dimethylpyrimidine To a mixture of 4-chloro-5-iodo-2,6-dimethylpyrimidine (0.50 g, 1.86 mmol) and B-(2-chloro-4-fluorophenyl)boronic acid (0.39 g, 2.24 mmol) in 1,4-dioxane (5 mL) and water (1 mL) was added potassium carbonate (0.62 g, 4.49 mmol) and tetrakis(triphenylphosphine)palladium (0.21 g, 0.18 mmol). The reaction mixture was heated at 100° C. for 18 h, and then cooled to room temperature and diluted with water and ethyl acetate. The layers were separated and the aqueous layer was extracted with ethyl acetate. The combined organics were washed with saturated aqueous sodium chloride solution, dried over magnesium sulfate, filtered and concentrated under reduced pressure. The resulting oil was purified by MPLC column chromatography (eluting with a gradient of 0 to 50% ethyl acetate in hexanes) to provide the title compound as a white solid (0.32 g).

$^1$H NMR ($CDCl_3$): δ 7.29 (d, 1H), 7.19 (m, 1H), 7.12 (m, 1H), 2.74 (s, 3H), 2.27 (s, 3H).

Step B: Preparation of 5-(2-chloro-4-fluorophenyl)-4-(3,5-dimethoxyphenyl)-2,6-dimethylpyrimidine To a mixture of 4-chloro-5-(2-chloro-4-fluorophenyl)-2,6-dimethylpyrimidine (i.e. the product of Step A) (0.3 g, 1.11 mmol) and B-(3,5-dimethoxyphenyl)boronic acid (0.30 g, 1.65 mmol) in toluene (36 mL) was added potassium carbonate (0.30 g, 2.17 mmol), tetrakis(triphenylphosphine)palladium (0.12 g, 0.104 mmol) and water (1 mL). The reaction mixture was heated at reflux for 24 h, cooled to room temperature and diluted with water and ethyl acetate. The layers were separated and the aqueous layer was extracted with ethyl acetate. The combined organics were washed with saturated aqueous sodium chloride solution, dried over magnesium sulfate, filtered and concentrated under reduced pressure. The resulting material was purified by MPLC column chromatography (eluting with a gradient of 0 to 20% ethyl acetate in hexanes) to provide the title compound, a compound of the present invention, as a solid (0.16 g).

$^1$H NMR ($CDCl_3$): δ 7.21 (d, 1H), 7.92-7.02 (m, 2H), 6.48 (s, 1H), 6.38 (s, 1H), 3.66 (s, 6H), 2.81 (s, 3H), 2.30 (s, 3H).

Example 15

Preparation of 4-(2-chloro-3,5-dimethoxyphenyl)-5-(2-chloro-4-fluorophenyl)-2,6-dimethylpyrimidine (Compound 42)

To a mixture of 5-(2-chloro-4-fluorophenyl)-4-(3,5-dimethoxyphenyl)-2,6-dimethylpyrimidine (i.e. the product of Example 14, Step B) (0.1 g, 0.27 mmol) in acetonitrile (3 mL) was added N-chlorosuccinimide (35 mg, 0.26 mmol). The reaction mixture was heated at 82° C. for 4 h, then allowed to stand at room temperature overnight, and then heated at reflux for 21 h. After cooling, the reaction mixture was diluted with water and ethyl acetate. The layers were separated and the aqueous layer was extracted with ethyl acetate. The combined organic layers were washed with saturated aqueous sodium chloride solution, dried over magnesium sulfate, filtered, and concentrated under reduced pressure. The resulting material was purified by MPLC column chromatography (eluting with a gradient of 0 to 30% ethyl acetate in hexanes) to provide the title compound, a compound of the present invention, as a solid (60 mg).

$^1$H NMR ($CDCl_3$): δ 7.12 (d, 1H), 6.88 (t, 1H), 6.48 (s, 1H), 6.39 (d, 1H), 6.32 (d, 1H), 3.81 (s, 3H), 3.67 (s, 3H), 3.66 (s, 3H), 2.82 (s, 3H), 2.32 (s, 3H).

Example 16

Preparation of 2-chloro-5-(2,6-difluorophenyl)-4-(3,5-dimethoxyphenyl)-6-methylpyrimidine (Compound 46)

Step A: Preparation of 5-(2,6-difluorophenyl)-2,4-dimethoxy-6-methyl-pyrimidine

A mixture of 1,3-difluorobenzene (2.25 g, 19.72 mmol) in tetrahydrofuran (26 mL) was cooled to −78° C., and then n-butyllithium (2.5 M in hexanes, 8.6 mL, 21.5 mmol) was added dropwise while maintaining the reaction temperature at −60° C. The reaction mixture was stirred for 1 h at about −78° C., and then a mixture of zinc chloride in 2-methyltetrahydrofuran (1.9 M, 12.5 mL, 23.7 mmol) was added dropwise while maintaining the reaction temperature at −65° C. The reaction mixture was allowed to warm to room temperature, stirred for 1 h, and then a mixture of 5-bromo-2,4-dimethoxy-6-methylpyrimidine (2.0 g, 8.58 mmol), dicyclohexyl[2',4',6'-tris(1-methylethyl)[1,1'-biphenyl]-2-yl]-phosphine (82 mg, 0.17 mmol) and XPhosPdG3 (CAS Number 1445085-55-1) (145 mg, 0.17 mmol) in tetrahydrofuran (38 mL) was added. The reaction mixture was heated at 70° C. for 18 h, cooled to room temperature and diluted with ice-cold water (30 mL). The resulting mixture was extracted with ethyl acetate, the layers were separated and the organic layer was washed with saturated aqueous sodium chloride solution, dried over magnesium sulfate, filtered, and concentrated under reduced pressure. The resulting material was purified by MPLC column chromatography (eluting with a gradient of 0 to 30% ethyl acetate in hexanes) to provide the title compound as an oil (1.8 g).

$^1$H NMR ($CDCl_3$): δ 7.34 (m, 1H), 6.97 (t, 2H), 4.03 (s, 3H), 3.93 (s, 3H), 2.23 (s, 3H).

Step B: Preparation of 5-(2,6-difluorophenyl)-6-methyl-2,4(1H,3H)-pyrimidinedione To a mixture of 5-(2,6-difluorophenyl)-2,4-dimethoxy-6-methyl-pyrimidine (i.e. the product of Step A) (1.74 g, 6.54 mmol) in methanol (65 mL) was added concentrated hydrochloric acid (4.5 mL). The reaction mixture was heated at 80° C. for 18 h, and then more concentrated hydrochloric acid (3 mL) was added to the reaction mixture. After an additional 6 h at 80° C., the reaction mixture was cooled to room temperature and concentrated under reduced pressure. The resulting material was partitioned between water and ethyl acetate. The layers were separated and the aqueous layer was extracted with ethyl acetate. The combined organics were washed with saturated aqueous sodium chloride solution, dried over magnesium sulfate, filtered, and concentrated under reduced pressure. The resulting material was mixed with diethyl ether and filtered to provide the title compound as a white solid (1.23 g).

$^1$H NMR (DMSO-$d_6$): δ 7.49 (m, 1H), 7.16 (t, 2H), 1.90 (s, 3H).

Step C: Preparation of 2,4-dichloro-5-(2,6-difluorophenyl)-6-methyl-pyrimidine

A mixture of 5-(2,6-difluorophenyl)-6-methyl-2,4(1H,3H)-pyrimidinedione (i.e. the product of Step B) (789 mg, 3.31 mmol) and phosphoric trichloride (20 mL, 0.21 mmol) was heated at 105° C. for 6 h, cooled to room temperature, diluted with toluene and concentrated under reduced pressure. The resulting material was purified by MPLC column chromatography (eluting with a gradient of 0 to 30% ethyl acetate in hexanes) to provide the title compound as a white solid (0.83 g).

$^1$H NMR ($CDCl_3$): δ 7.50 (m, 1H), 7.07 (t, 2H), 2.39 (s, 3H).

Step D: Preparation of 2-chloro-5-(2,6-difluorophenyl)-4-(3,5-dimethoxyphenyl)-6-methylpyrimidine To a mixture of 2,4-dichloro-5-(2,6-difluorophenyl)-6-methyl-pyrimidine (i.e. the product of Step C) (0.83 g, 3.02 mmol) and B-(3,5-dimethoxyphenyl)boronic acid (0.63 g, 3.46 mmol) in toluene (50 mL) was added potassium carbonate (1.25 g, 9.0 mmol), tetrakis-(triphenylphosphine) palladium (0.35 g, 0.30 mmol) and water (2.75 mL). The reaction mixture was heated at reflux for 20 h, cooled to room temperature and diluted with water and ethyl acetate. The layers were separated and the aqueous layer was extracted with ethyl acetate. The combined organics were washed with saturated aqueous sodium chloride solution, dried over magnesium sulfate, filtered, and concentrated under reduced pressure. The resulting oil was purified by MPLC column chromatography (eluting with a gradient of 0 to 30% ethyl acetate in hexanes) to provide the title compound, a compound of the present invention, as an oil (50 mg).

$^1$H NMR ($CDCl_3$): δ 6.38 (m, 1H), 6.93 (t, 2H), 6.50 (s, 2H), 6.41 (s, 1H), 3.65 (s, 6H), 2.40 (s, 3H).

Example 17

Preparation of 2-chloro-4-(2-chloro-3,5-dimethoxyphenyl)-5-(2,6-difluorophenyl)-6-methylpyrimidine (Compound 48)

To a mixture of 2-chloro-5-(2,6-difluorophenyl)-4-(3,5-dimethoxyphenyl)-6-methyl-pyrimidine (i.e. the product of Example 16, Step D) (50 mg, 0.13 mmol) in acetonitrile (3 mL) was added N-chlorosuccinimide (18 mg, 0.13 mmol). The reaction mixture was heated at 80° C. for 20 h, cooled to room temperature and diluted with water. The layers were separated and the aqueous layer was extracted with ethyl acetate. The combined organics were washed with saturated aqueous sodium chloride solution, dried over magnesium sulfate, filtered, and concentrated under reduced pressure to provide the title compound, a compound of the present invention, as an oil (80 mg).

$^1$H NMR ($CDCl_3$): δ 7.29 (m, 1H), 6.86 (t, 2H), 6.42 (s, 1H), 6.37 (s, 1H), 3.79 (s, 3H), 3.71 (s, 3H), 2.44 (s, 3H).

Example 18

Preparation of 2-chloro-5-(2-chloro-4-fluorophenyl)-4-(3,5-dimethoxyphenyl)-6-methylpyrimidine (Compound 45)

Step A: Preparation of 5-(2-chloro-4-fluorophenyl)-2,4-dimethoxy-6-methylpyrimidine To a mixture of 5-bromo-2,4-dimethoxy-6-methylpyrimidine (2.10 g, 9.01 mmol) and B-(2-chloro-4-fluorophenyl) boronic acid (2.35 g, 13.5 mmol) in 1,4-dioxane (24 mL) was added potassium carbonate (3.0 g, 21.7 mmol), tetrakis (triphenylphosphine)palladium (1.04 g, 0.90 mmol) and water (4 mL). The reaction mixture was heated at 100° C. for 20 h, cooled to room temperature and diluted with water and ethyl acetate. The layers were separated and the aqueous layer was extracted with ethyl acetate. The combined organics were washed with saturated aqueous sodium chloride solution, dried over magnesium sulfate, filtered and concentrated under reduced pressure. The resulting material was purified by MPLC column chromatography (eluting with a gradient of 0 to 20% ethyl acetate in hexanes) to provide the title compound as an oil (1.69 g).

$^1$H NMR ($CDCl_3$): δ 6.38 (m, 1H), 6.93 (t, 2H), 6.50 (s, 2H), 6.41 (s, 1H), 3.65 (s, 6H), 2.40 (s, 3H).

Step B: Preparation of 5-(2-chloro-4-fluorophenyl)-6-methyl-2,4(1H,3H)-pyrimidinedione To a mixture of 5-(2-chloro-4-fluorophenyl)-2,4-dimethoxy-6-methylpyrimidine (i.e. the product of Step A) (1.59 g, 5.62 mmol) in methanol (51 mL) was added concentrated hydrochloric acid (3 mL). The reaction mixture was heated at 80° C. for 3.5 h, then allowed to stand at room temperature overnight, and then heated at reflux for 20 h. After cooling, the reaction mixture was concentrated under reduced pressure and then partitioned between water and ethyl acetate. The layers were separated and the aqueous layer was extracted with ethyl acetate. The combined organic layers were washed with saturated aqueous sodium chloride solution, dried over magnesium sulfate, filtered and concentrated under reduced pressure. The resulting material was mixed with diethyl ether and filtered to provide the title compound as a white solid (1.09 g).

$^1$H NMR (DMSO-$d_6$): δ 7.50 (d, 1H), 7.32 (m, 1H), 7.24 (t, 1H), 1.82 (s, 3H).

Step C: Preparation of 2,4-dichloro-5-(2-chloro-4-fluorophenyl)-6-methylpyrimidine A mixture of 5-(2-chloro-4-fluorophenyl)-6-methyl-2,4 (1H,3H)-pyrimidinedione (i.e. the product of Step B) (1.07 g, 4.21 mmol) and phosphoric trichloride (26 mL, 0.28 mol) was heated at 105° C. for 4 h, cooled to room temperature, diluted with toluene and concentrated under reduced pressure. The resulting material was purified by MPLC column chromatography (eluting with a gradient of 0 to 30% ethyl acetate in hexanes) to provide the title compound as a white solid (1.08 g).

$^1$H NMR (DMSO-$d_6$): δ 7.73 (d, 1H), 7.59 (t, 1H), 7.06 (t, 1H), 2.25 (s, 3H).

Step D: Preparation of 2-chloro-5-(2-chloro-4-fluorophenyl)-4-(3,5-dimethoxyphenyl)-6-methylpyrimidine To a mixture of 2,4-dichloro-5-(2-chloro-4-fluorophenyl)-6-methylpyrimidine (i.e. the product of Step C) (0.79 g, 2.71 mmol) and B-(3,5-dimethoxyphenyl)boronic acid (0.60 g, 3.3 mmol) in toluene (45 mL) was added potassium carbonate (1.12 g, 8.10 mmol), tetrakis(triphenylphosphine) palladium (0.31 g, 0.27 mmol) and water (2.5 mL). The reaction mixture was heated at reflux for 20 h, cooled to room temperature and diluted with water and ethyl acetate. The layers were separated and the aqueous layer was extracted with ethyl acetate. The combined organics were washed with saturated aqueous sodium chloride solution, dried over magnesium sulfate, filtered and concentrated under reduced pressure. The resulting oil was purified by MPLC column chromatography (eluting with a gradient of 0 to 20% ethyl acetate in hexanes) to provide the title compound, a compound of the present invention, as an oil (100 mg).

$^1$H NMR ($CDCl_3$): δ 7.00 (m, 2H), 6.49 (s, 2H), 6.40 (s, 1H), 6.02 (s, 1H), 3.76 (s, 3H), 3.66 (s, 6H), 2.33 (s, 3H).

Example 19

Preparation of 2-chloro-4-(2-chloro-3,5-dimethoxyphenyl)-5-(2-chloro-4-fluorophenyl)-6-methylpyrimidine (Compound 49)

To a mixture of 2-chloro-5-(2-chloro-4-fluorophenyl)-4-(3,5-dimethoxyphenyl)-6-methylpyrimidine (i.e. the product of Example 18, Step D) (100 mg, 0.25 mmol) in acetonitrile (4 mL) was added N-chlorosuccinimide (44 mg, 0.33 mmol). The reaction mixture was heated at 82° C. for 4 h, and then cooled to room temperature and diluted with water. The layers were separated and the aqueous layer was extracted with ethyl acetate. The combined organics were washed with saturated aqueous sodium chloride solution, dried over magnesium sulfate, filtered and concentrated under reduced pressure. The resulting material was purified by MPLC column chromatography (eluting with 20% ethyl acetate in heptanes) to provide the title compound, a compound of the present invention, as a solid (30 mg).

$^1$H NMR ($CDCl_3$): δ 7.26 (d, 1H), 7.14 (d, 1H), 7.00 (m, 1H), 6.91 (t, 1H), 6.49 (s, 1H), 6.40 (s, 1H), 6.30 (s, 1H), 3.82 (s, 3H), 3.68 (s, 3H), 2.36 (s, 3H).

Example 20

Preparation of 5-(2-chloro-4-fluorophenyl)-4-(2-chloro-5-methoxyphenyl)-2,6-dimethylpyrimidine (Compound 50)

To a mixture of 4-chloro-5-(2-chloro-4-fluorophenyl)-2,6-dimethylpyrimidine (i.e. the product of Example 14, Step A) (0.37 g, 1.37 mmol) and B-(2-chloro-5-methoxyphenyl) boronic acid (0.38 g, 2.04 mmol) in toluene (45 mL) and water (1.35 mL) was added potassium carbonate (0.37 g, 2.68 mmol) and tetrakis(triphenylphosphine)palladium (0.16 g, 0.14 mmol). The reaction mixture was heated at 110° C. overnight, cooled to room temperature and then diluted with water. The resulting mixture was extracted with ethyl acetate and the combined organics were washed with saturated aqueous sodium chloride solution, dried over magnesium sulfate, filtered and concentrated under reduced pressure. The resulting material was purified by MPLC column chromatography (eluting with a gradient of 0 to 20% ethyl acetate in hexanes) to provide the title compound, a compound of the present invention, as a solid (0.13 g).

$^{1}$H NMR ($CDCl_3$): δ 7.17 (d, 1H), 7.14 (m, 1H), 7.12. (d, 1H), 6.89 (t, 1H), 6.72 (m, 1H), 6.70 (s, 1H), 3.68 (s, 3H), 2.83 (s, 3H), 2.33 (s, 3H).

Example 21

Preparation of 4-chloro-6-(3,5-dimethoxyphenyl)-2-methyl-5-(2,4,6-trifluorophenyl)pyrimidine (Compound 65)

Step A: Preparation of ethyl 2-(2,4,6-trifluorophenyl)acetate

To a mixture of 2,4,6-trifluorobenzeneacetic acid (45 g, 0.24 mol) in ethyl alcohol (120 mL) was added concentrated sulfuric acid (1.2 mL). The reaction mixture was heated at reflux overnight, cooled to room temperature and then concentrated under reduced pressure. The resulting material was diluted with water and extracted with ethyl acetate. The combined organics were washed with saturated aqueous sodium chloride solution, dried over magnesium sulfate, filtered and concentrated under reduced pressure to provide the title compound as an oil (48.3 g).

$^{1}$H NMR ($CDCl_3$): δ 6.67 (dd, 2H), 4.18 (q, 2H), 3.64 (s, 2H), 1.26 (t, 3H).

$^{19}$F NMR ($CDCl_3$): δ−111.63 (m, 2F), −109.18 (m, 1F).

Step B: Preparation of 1,3-diethyl 2-(2,4,6-trifluorophenyl)propanedioate

To a mixture of ethyl 2-(2,4,6-trifluorophenyl)acetate (i.e. the product of Step A) (6.36 g, 29.2 mmol) in tetrahydrofuran (62 mL) at −78° C. was added dropwise a solution of lithium bis(trimethylsilyl)amide (1 M in THF, 35 mL, 0.035 mol). The reaction mixture was stirred for 45 minutes at about −78° C., and then a solution of ethyl 1H-imidazole-1-carboxylate (5.2 mL, 43.1 mmol) in tetrahydrofuran (62 mL) was added dropwise. The reaction mixture was allowed to gradually warm to 0° C., then cooled to about −78° C. and saturated aqueous ammonium chloride solution was added. The resulting mixture was extracted with ethyl acetate and the combined organics were washed with saturated aqueous sodium chloride solution, dried over sodium sulfate, filtered and concentrated under reduced pressure. The resulting material was purified by MPLC column chromatography (eluting with a gradient of 0 to 10% ethyl acetate in hexanes) to provide the title compound as an oil (5.03 g)

$^{1}$H NMR ($CDCl_3$): δ 6.78-6.60 (m, 2H), 4.90 (s, 1H), 4.26 (q, 4H), 1.37-1.21 (m, 6H).

$^{19}$F NMR ($CDCl_3$): δ−109.42-−109.06 (m, 1F), −107.50-−107.09 (m, 1F).

Step C: Preparation of 2-methyl-5-(2,4,6-trifluorophenyl)pyrimidine-4,6-diol A mixture of 1,3-diethyl 2-(2,4,6-trifluorophenyl)propanedioate (i.e. the product of Step B) (3.01 g, 10.4 mmol), acetamidine hydrochloride (1.5 g, 15.9 mmol) and 1,8-diazabicyclo[5.4.0]undec-7-ene (DBU) (2.33 g, 20.8 mmol) in 1-methyl-2-pyrrolidinone (10 mL) was heated at 95° C. for 5 h, and then heated at 100° C. for 1 h. The reaction mixture was cooled to room temperature and then hydrochloric acid (1 N in water) was added. The resulting solid precipitate was collected by filtration, rinsing with water, to provide the title compound as a white solid (1.1 g).

$^{1}$H NMR (DMSO-$d_6$): δ 12.68-11.87 (m, 2H), 7.10 (dd, 2H), 2.32 (s, 3H).

$^{19}$F NMR (DMSO-$d_6$): δ −110.82 (br s, 1F), −109.36 (t, 1F), −106.41 (br s, 1F).

Step D: Preparation of 4,6-dichloro-2-methyl-5-(2,4,6-trifluorophenyl)pyrimidine A mixture of 2-methyl-5-(2,4,6-trifluorophenyl)pyrimidine-4,6-diol (i.e. the product of Step C) (300 mg, 1.17 mmol) and phosphoric trichloride (7.2 mL) was heated at 105° C. for 3 h, and then allow to cool to room temperature. The reaction mixture was diluted with toluene and concentrated under reduced pressure, and then dichloromethane was added and again concentrated under reduced pressure. The resulting material was purified by MPLC column chromatography (eluting with a gradient of 0 to 100% ethyl acetate in hexanes) to provide the title compound as a white solid (0.3 g).

$^{1}$H NMR ($CDCl_3$): δ 6.91-6.75 (m, 2H), 2.78 (s, 3H).

Step E: Preparation of 4-chloro-6-(3,5-dimethoxyphenyl)-2-methyl-5-(2,4,6-trifluorophenyl)pyrimidine To a mixture of 4,6-dichloro-2-methyl-5-(2,4,6-trifluorophenyl)pyrimidine (i.e. the product of Step D) (1.2 g, 4.1 mmol) and B-(3,5-dimethoxyphenyl)boronic acid (0.89 g, 4.9 mmol) in toluene (110 mL) and water (3.5 mL) was added potassium carbonate (1.13 g, 8.18 mmol) and tetrakis(triphenylphosphine)palladium (0.47 g, 0.41 mmol). The reaction mixture was heated at 110° C. for 6 h, cooled to room temperature and diluted with water. The resulting mixture was extracted with ethyl acetate and the combined organics were washed with saturated sodium aqueous chloride solution, dried over magnesium sulfate, filtered and concentrated under reduced pressure. The resulting material was purified by MPLC column chromatography (eluting with a gradient of 0 to 30% ethyl acetate in hexanes) to provide the title compound, a compound of the present invention, as a solid (1.08 g).

$^{1}$H NMR ($CDCl_3$): δ 6.70-6.67 (m, 2H), 6.51-6.46 (m, 2H), 6.45-6.43 (m, 1H), 3.69 (s, 6H), 2.84 (s, 3H).

$^{19}$F NMR ($CDCl_3$): δ−107.14 (t, 1F), −105.28 (t, 1F).

Example 22

Preparation of 4-(3,5-dimethoxyphenyl)-2,6-dimethyl-5-(2,4,6-trifluorophenyl)pyrimidine (Compound 53)

To a mixture of 4-chloro-6-(3,5-dimethoxyphenyl)-2-methyl-5-(2,4,6-trifluorophenyl)pyrimidine (i.e. the product of Example 21, Step E) (300 mg, 0.76 mmol) in tetrahydrofuran (10 mL) at −78° C. was added methylmagnesium bromide (3.4 M in 2-methyltetrahydrofuran, 1.2 mL). The reaction mixture was allowed to warm to room temperature and stirred overnight. The reaction mixture was cooled to 0° C., and then iron(III) acetylacetonate (27 mg, 0.076 mmol)

in tetrahydrofuran (1 mL) was added, and the mixture was allowed to warm to room temperature. The reaction mixture was cooled to 0° C., and then diluted with water and extracted with ethyl acetate. The combined organics were washed with saturated aqueous sodium chloride solution, dried over magnesium sulfate, filtered and concentrated under reduced pressure. The resulting material was purified by MPLC column chromatography (eluting with a gradient of 0 to 30% ethyl acetate in hexanes) to provide the title compound, a compound of the present invention, as an oil (0.16 g).

$^1$H NMR ($CDCl_3$): δ 6.68 (dd, 2H), 6.46 (d, 2H), 6.41-6.39 (m, 1H), 3.69 (s, 6H), 2.82 (s, 3H), 2.37 (s, 3H).

$^{19}$F NMR ($CDCl_3$): δ−107.50 (t, 1F), −106.83−−106.34 (t, 1F).

Example 23

Preparation of 4-(2-chloro-3,5-dimethoxyphenyl)-2,6-dimethyl-5-(2,4,6-trifluorophenyl)pyrimidine (Compound 54)

A mixture of 4-(3,5-dimethoxyphenyl)-2,6-dimethyl-5-(2,4,6-trifluorophenyl)pyrimidine (i.e. the product of Example 22) (40 mg, 0.11 mmol) and N-chlorosuccinimide (13 mg, 0.097 mmol) in acetonitrile (3 mL) was heated at 80° C. overnight. The reaction mixture was cooled to room temperature, diluted with water and extracted with ethyl acetate. The combined organics were washed with water, saturated aqueous sodium chloride solution, dried over magnesium sulfate, filtered and concentrated under reduced pressure. The resulting material was purified by MPLC column chromatography (eluting with a gradient of 0 to 20% ethyl acetate in hexanes) to provide the title compound, a compound of the present invention, as a solid (60 mg).

$^1$H NMR ($CDCl_3$): δ 6.74-6.51 (m, 2H), 6.43 (d, 1H), 6.38 (s, 1H), 3.81 (s, 3H), 3.73 (s, 3H), 2.82 (s, 3H), 2.39 (s, 3H).

$^{19}$F NMR ($CDCl_3$): δ−106.43 (m, 1F).

Example 24

Preparation of 4-(3,5-dimethoxyphenyl)-6-ethyl-2-methyl-5-(2,6-difluorophenyl)pyrimidine (Compound 66)

To a mixture of 4-chloro-6-(3,5-dimethoxyphenyl)-2-methyl-5-(2,6-difluorophenyl)pyrimidine (prepared analogous to the method of Example 21, Steps A-E) (390 mg, 1.04 mmol) in tetrahydrofuran (12 mL) at −50° C. was added ethylmagnesium bromide (3.4 M in THF, 0.69 g, 1.522 mL, 0.005 mol). The reaction mixture was allowed to warm to room temperature and stirred overnight. The reaction mixture was cooled to 0° C. and then iron(III) acetylacetonate (37 mg, 0.104 mmol) in tetrahydrofuran (1 mL) was added. The reaction mixture was allowed to warm to room temperature and stirred for 30 minutes, cooled, and then diluted with water. The resulting mixture was extracted with ethyl acetate and the combined organics were washed with saturated aqueous sodium chloride solution, dried over magnesium sulfate, filtered and concentrated under reduced pressure. The resulting material was purified by MPLC column chromatography (eluting with a gradient of 0 to 25% ethyl acetate in hexanes) to provide the title compound, a compound of the present invention, as an oil (0.18 g).

$^1$H NMR ($CDCl_3$): δ 7.35-7.28 (m, 1H), 6.92-6.84 (m, 2H), 6.48 (d, 2H), 6.37 (t, 1H), 3.65 (s, 6H), 2.83 (s, 3H), 2.59 (q, 2H), 1.18 (t, 3H).

$^{19}$F NMR ($CDCl_3$): δ−111.69 (t, 1F), −110.28 (t, 1F).

Example 25

Preparation of 3-(2-chloro-3,5-dimethoxyphenyl)-4-(2-chloro-4-fluorophenyl)-5-methyl-6H-1,2-oxazin-6-one (Compound 64)

Step A: Preparation of ethyl 2-chloro-4-fluoro-β-hydroxy-α-methylenebenzenepropanoate To a mixture of 2-chloro-4-fluorobenzaldehyde (20 g, 0.13 mol) and ethyl 2-propenoate (13.65 mL, 0.13 mol) was added 1,4-diazabicyclo[2.2.2]octane (7.07 g, 63.03 mmol). The reaction mixture was stirred at room temperature for 16 h, and then ice-cold water (500 mL) was added. The resulting mixture was extracted with ethyl acetate (2×500 mL) and the combined organics were washed with saturated aqueous sodium chloride solution, dried over sodium sulfate, filtered and concentrated under reduced pressure. The resulting material was purified by silica gel column chromatography (eluting with 5% ethyl acetate in hexanes) to provide the title compound as a light brown oil (20 g).

$^1$H NMR (DMSO-$d_6$): δ 7.42-7.38 (m, 2H), 7.23-7.19 (m, 1H), 6.25 (s, 1H), 5.91 (d, 1H), 5.78-5.75 (m, 2H), 4.10-4.03 (m, 2H), 1.12 (t, 3H).

Step B: Preparation of ethyl 2-(bromomethyl)-3-(2-chloro-4-fluorophenyl)-2-propenoate A mixture of ethyl 2-chloro-4-fluoro-β-hydroxy-α-methylenebenzenepropanoate (i.e. the product of Step A) (20 g, 77.51 mmol) in hydrobromic acid (47% aqueous solution, 40 mL, 77.51 mmol) was heated at 75° C. After 4 h, the reaction mixture was cooled, and then ice-cold water (500 mL) was added. The resulting mixture was extracted with ethyl acetate (2×400 mL) and the combined organics were washed with saturated aqueous sodium chloride solution, dried over sodium sulfate, filtered and concentrated under reduced pressure. The resulting material was purified by silica gel column chromatography (eluting with 5% ethyl acetate in hexanes) to provide the title compound as a pale-yellow oil (16 g, mixture of cis and trans isomers).

LCMS: m/z: 321 $[M+H]^+$

Step C: Preparation of ethyl 2-chloro-3-(2-chloro-4-fluorophenyl)-7-hydroxy-3,5-dimethoxy-α-methylenebenzenebutanoate To a mixture of ethyl 2-(bromomethyl)-3-(2-chloro-4-fluorophenyl)-2-propenoate (i.e. the product of Step B) (8 g, 25.07 mmol) and 2-chloro-3,5-dimethoxybenzaldehyde (5.01 g, 25.07 mmol) in tetrahydrofuran (100 mL) and water (100 mL) was added portionwise indium powder (3.14 g, 27.35 mmol). The reaction mixture was allowed to stir at room temperature for 24 h, and then filtered through a pad of Celite®. The filtrate was extracted with ethyl acetate (2×200 mL) and the combined organics were washed with saturated aqueous sodium chloride solution (2×500 mL), dried over sodium sulfate, filtered and concentrated under reduced pressure. The resulting material was mixed with n-pentane and filtered to provide the title compound as an off-white solid (7 g).

$^1$H NMR (DMSO-$d_6$): δ 7.57-7.53 (m, 1H), 7.18-7.14 (m, 2H), 6.53 (d, 1H), 6.33 (s, 1H), 6.12 (s, 1H), 6.07 (d, 1H), 5.79 (d, 1H), 5.52 (t, 1H), 4.66-4.65 (m, 1H), 4.01-3.91 (m, 2H), 3.80 (s, 3H), 3.51 (s, 3H), 1.05 (t, 3H).

Step D: Preparation of ethyl 2-chloro-3-(2-chloro-4-fluorophenyl)-3,5-dimethoxy-α-methylene-T-oxobenzenebutanoate To a mixture of ethyl 2-chloro-3-(2-chloro-4-fluorophenyl)-7-hydroxy-3,5-dimethoxy-α-methylenebenzenebutanoate (i.e. the product of Step C) (7 g, 15.8 mmol) in dichloromethane (100 mL) at 0° C. was added pyridinium chlorochromate (5.12 g, 23.75 mmol). The reaction mixture was allowed to warm to room temperature and stirred for 16 h, and then filtered through a pad of Celite®, rinsing with dichloromethane (100 mL). The filtrate was concentrated under reduced pressure and the resulting material was purified by silica gel column chromatography (eluting with 15% ethyl acetate in hexanes) to provide the title compound as a pale-yellow solid (6 g).

$^1$H NMR ($CDCl_3$): δ 7.33-7.29 (m, 1H), 7.15 (dd, 1H), 7.00-6.96 (m, 1H), 6.88 (d, 1H), 6.55 (d, 1H), 6.47 (s, 1H), 6.22 (s, 1H), 5.34 (s, 1H), 4.23 (q, 2H), 3.84 (s, 3H), 3.81 (s, 3H), 1.28 (t, 3H).

Step E: Preparation of ethyl 4-(2-chloro-3,5-dimethoxyphenyl)-3-(2-chloro-4-fluorophenyl)-2-methyl-4-oxo-2-butenoate To a mixture of ethyl 2-chloro-3-(2-chloro-4-fluorophenyl)-3,5-dimethoxy-α-methylene-γ-oxobenzenebutanoate (i.e. the product of Step D) (6 g, 13.63 mmol) in N,N-dimethylformamide (80 mL) was added triethylamine (2.01 mL, 13.63 mmol) and the reaction mixture was heated at 90° C. for 16 h, and then ice-cold water (500 mL) was added. The resulting mixture was extracted with ethyl acetate (2×200 mL) and the combined organics were washed with saturated aqueous sodium chloride solution, dried over sodium sulfate and concentrated under reduced pressure. The resulting material was purified by silica gel column chromatography (eluting with 15% ethyl acetate in hexanes) to provide the title compound as a pale-yellow solid (2.5 g, mixture of cis and trans isomers).

Step F: Preparation of ethyl 4-(2-chloro-3,5-dimethoxyphenyl)-3-(2-chloro-4-fluorophenyl)-4-(hydroxyimino)-2-methyl-2-butenoate To a mixture of ethyl 4-(2-chloro-3,5-dimethoxyphenyl)-3-(2-chloro-4-fluorophenyl)-2-methyl-4-oxo-2-butenoate (i.e. the product of Step E) (0.25 g, 0.58 mmol) in dichloromethane (20 mL) at 0° C. was added triethylamine (0.16 mL, 1.17 mmol), glacial acetic acid (0.07 mL, 1.17 mmol) and hydroxylamine hydrochloride (0.081 g, 1.17 mmol). The reaction mixture was allowed to warm to room temperature and stirred for 48 h, and then ice-cold water (50 mL) was added. The resulting mixture was extracted with dichloromethane (2×100 mL) and the combined organic layers were washed with saturated aqueous sodium chloride solution, dried over sodium sulfate, filtered and concentrated under reduced pressure. The resulting material (0.28 g) was used directly in the next step without further purification.

LCMS m/z: 456 $[M+H]^+$

Step G: Preparation of 3-(2-chloro-3,5-dimethoxyphenyl)-4-(2-chloro-4-fluorophenyl)-5-methyl-6H-1,2-oxazin-6-one To a mixture of ethyl 4-(2-chloro-3,5-dimethoxyphenyl)-3-(2-chloro-4-fluorophenyl)-4-(hydroxyimino)-2-methyl-2-butenoate (i.e. the product of Step F) (0.28 g) in glacial acetic acid (20 mL) was heated at 100° C. for 16 h, and then ice-cold water (50 mL) was added. The resulting mixture was extracted with ethyl acetate (2×50 mL) and the combined organics were washed with saturated aqueous sodium chloride solution, dried over sodium sulfate, filtered and concentrated under reduced pressure. The resulting material was purified by preparative HPLC (YMC Triart C18 (150×25 mm 10μ) column; mobile phase: A. 0.10% formic acid in water and B. acetonitrile; gradient 0/40, 4/75, 8/75, 9/95, 10/95, 12/40% B over 14 minutes) to provide the title compound, a compound of the present invention, as a brown solid (25 mg).

$^1$H NMR (DMSO-$d_6$): δ 7.53 (dd, 1H), 7.45-7.41 (m, 1H), 7.35-7.25 (m, 1H), 6.72-6.60 (m, 2H), 3.81 (s, 3H), 3.72 (s, 3H), 1.90 (s, 3H).

LCMS m/z: 410 $[M+H]^+$

Example 26

Preparation of 3-(2-chloro-4-fluorophenyl)-4-(2-chloro-5-methoxyphenyl)-2,6-dimethylpyridine (Compound 138)

Step A: Preparation of 1-(2-chloro-4-fluorophenyl)-2-propanone

To a mixture of 2-chloro-4-fluorobenzenamine (30.0 g, 0.21 mol) in trifluoroacetic acid (300 mL) at 0° C. was added sodium nitrite (15.6 g, 0.23 mol) portionwise. After 30 minutes, sulfamic acid (2.0 g, 0.02 mol) was added and stirring was continued for an additional 30 minutes at 0° C.

In a separate reaction flask, a mixture of isopropenyl acetate (41.2 g, 0.41 mol) in acetonitrile (300 mL) at 0° C. was charged with ferrocene (2.3 g, 0.012 mol). After 1 h at 0° C., the above reaction mixture (i.e. diazonium salt) was added dropwise while maintaining the reaction temperature at 0° C. The reaction mixture was allowed to warm to room temperature, and then diluted with saturated aqueous sodium bicarbonate solution (1 L). The resulting mixture was extracted with ethyl acetate (2×500 mL) and the combined organic extracts were washed with saturated aqueous sodium chloride solution (500 mL), dried over sodium sulfate, filtered and concentrated under reduced pressure. The resulting material was purified by silica gel column chromatography (eluting with 8% ethyl acetate in diethyl ether) to provide the title compound as an oil (16.0 g).

$^1$H NMR ($CDCl_3$): δ 7.19-7.14 (m, 2H), 6.98-6.95 (m, 1H), 3.81 (s, 2H), 2.20 (s, 3H).

Step B: Preparation of 3-(2-chloro-4-fluorophenyl)-2,6-dimethyl-4H-pyran-4-one

To a mixture of 1-(2-chloro-4-fluorophenyl)-2-propanone (i.e. the product of Step A) (16.0 g, 0.086 mol) in acetic anhydride (34 mL) at 0° C. was added a solution of phosphorus pentoxide-methanesulfonic acid (also known as Eaton's reagent, CAS no. 39394-84-8) (80 mL) in acetic anhydride (34 mL, 0.66 mol). The reaction mixture was stirred at 0° C. for 5 minutes and then heated at 50° C. for 2 h. The reaction mixture was diluted with ice-cold water (300 mL) and extracted with ethyl acetate (2×300 mL). The combined organic extracts were washed with water (2×200 mL) and saturated aqueous sodium chloride solution (300 mL), dried over sodium sulfate, filtered and concentrated under reduced pressure. The resulting material was purified by silica gel column chromatography (eluting with 30% ethyl acetate in diethyl ether) to provide the title compound as an oil (8.0 g).

$^1$H NMR ($CDCl_3$): δ 7.24-7.21 (m, 1H), 7.18-7.15 (m, 1H), 7.06-7.04 (m, 1H), 6.20 (s, 1H), 2.35 (s, 3H), 2.09 (s, 3H).

LCMS m/z: 253 $[M+H]^+$

Step C: Preparation of 3-(2-chloro-4-fluorophenyl)-2,6-dimethylpyridin-4(1H)-one To a mixture of 3-(2-chloro-4-fluorophenyl)-2,6-dimethyl-4H-pyran-4-one (i.e. the product of Step B) (8.0 g, 0.029 mol) in ethanol (7 mL) was added ammonium hydroxide (100 mL). The reaction mixture was heated in a steel pressure reactor at 180° C. for 24 h. The resulting mixture was allowed to cool to room temperature and then concentrated under reduced pressure. The resulting material was purified by trituration with 10-20% diethyl ether in pentane to provide the title compound as a pale brown solid (7.1 g) melting at 292-295° C.

$^1$H NMR (DMSO-$d_6$): δ 11.18 (br s, 1H), 7.47-7.44 (dd, 1H), 7.22-7.18 (t, 2H), 5.91 (s, 1H), 2.20 (s, 3H), 1.92 (s, 3H).

LCMS m/z: 252 $[M+H]^+$

Step D: Preparation of 4-bromo-3-(2-chloro-4-fluorophenyl)-2,6-dimethylpyridine

To a mixture of 3-(2-chloro-4-fluorophenyl)-2,6-dimethylpyridin-4(1H)-one (i.e. the product of Step C) (7.1 g, 0.03 mol) was added phosphoryl bromide (30 g, 0.11 mol). The reaction mixture was heated in a steel pressure reactor at 180° C. for 1 h. The resulting mixture was diluted with ice-cold water (100 mL) and saturated aqueous sodium bicarbonate solution, and then extracted with ethyl acetate (2×200 mL). The combined organic extracts were concentrated under reduced pressure. The resulting material was purified by silica gel column chromatography (eluting with 60% ethyl acetate in diethyl ether) to provide the title compound (3.4 g) as an off-white solid.

$^1$H NMR ($CDCl_3$): δ 7.35 (s, 1H), 7.28 (d, 1H), 7.16-7.07 (m, 2H), 2.55 (s, 3H), 2.27 (s, 3H).

LCMS m/z: 314 $[M+H]^+$

Step E: Preparation of 3-(2-chloro-4-fluorophenyl)-4-(2-chloro-5-methoxyphenyl)-2,6-dimethylpyridine To a mixture of 4-bromo-3-(2-chloro-4-fluorophenyl)-2,6-dimethylpyridine (i.e. the product of Step D) (500 mg, 1.59 mmol) and 2-chloro-5-methoxyphenylboronic acid (592 mg, 3.18 mmol) in ethanol (2 mL), toluene (8 mL) and water (1 mL), was added sodium carbonate (334 mg, 3.18 mmol). The reaction mixture was degassed by bubbling nitrogen gas through the reaction mixture for 5 minutes, and then tetrakis(triphenylphosphine)palladium (459 mg, 0.398 mmol) was added and the mixture was heated at 100° C. After 16 h, the reaction mixture was diluted with ice-cold water (30 mL) and extracted with ethyl acetate (2×30 mL). The combined organic extracts were washed with water (2×20 mL) and saturated aqueous sodium chloride solution (50 mL), dried over sodium sulfate, filtered and concentrated under reduced pressure. The resulting material was purified by preparative HPLC to provide the title compound, a compound of the present invention, as an off white solid (150 mg) melting at 106-108° C.

$^1$H NMR (DMSO-$d_6$): δ 7.49-7.47 (d, 1H), 7.39-7.30 (m, 1H), 7.15-7.13 (d, 2H), 7.10-7.09 (d, 1H), 6.83-6.77 (m, 1H), 6.63-6.62 (d, 1H), 3.63 (s, 3H), 2.50 (s, 3H), 2.18 (s, 3H).

LCMS m/z: 376 [M+H]+

Example 27

Preparation of 1,2-dihydro-5-(3,5-dimethoxyphenyl)-1-methyl-2-oxo-6-(2,4,6-trifluorophenyl)-3-pyridinecarbonitrile (Compound 67)

Step A: Preparation of methyl 2,4,6-trifluorobenzoate

To a mixture of 2,4,6-trifluorobenzoic acid (20 g, 113.5 mmol) in methanol (200 mL) was added sulfuric acid (5 mL). The reaction mixture was heated at 80° C. for 16 h, cooled to room temperature and concentrated under reduced pressure. The resulting material was diluted with ice-cold water and extracted with dichloromethane (3×300 mL). The combined organic extracts were washed with saturated aqueous sodium bicarbonate solution (100 mL) and saturated aqueous sodium chloride solution (100 mL), dried over sodium sulfate, filtered and concentrated under reduced pressure to provide a colorless oil. The oil was combined with toluene (2×150 mL) and concentrated under reduced pressure to provide the title compound as an oil (17 g).

$^1$H NMR ($CDCl_3$): δ 7.75 (m, 2H), 7.2 (m, 2H), 3.96 (s, 3H).

Step B: Preparation of 2-(3,5-dimethoxyphenyl)-1-(2,4,6-trifluorophenyl)ethanone To a mixture of 2-(3,5-dimethoxyphenyl)acetic acid (15.5 g, 79 mmol) in tetrahydrofuran (155 mL) at −78° C. was added dropwise lithiumbis(trimethylsilyl)amide (1 M in tetrahydrofuran, 237 mL, 237 mmol). The reaction mixture was stirred for 1 h at −78° C., and then a solution of methyl 2,4,6-trifluorobenzoate (i.e. the product of Step A) (16.5 g, 86.9 mmol) in tetrahydrofuran (50 mL) was added dropwise. The reaction mixture was allowed to warm to room temperature and stirred for 5 h, and then brought to pH 6 by adding hydrochloric acid (1 N aqueous solution). The resulting mixture was extracted with ethyl acetate (3×300 mL). The organic extracts were washed with water (200 mL) and saturated aqueous sodium chloride solution (200 mL), dried over sodium sulfate, filtered and concentrated under reduced pressure. The resulting material was purified by silica gel column chromatography (eluting with 0-20% ethyl acetate in petroleum ether) to provide the title compound as a yellow oil (7.5 g).

$^1$H NMR ($CDCl_3$): δ 6.67 (m, 2H), 6.35 (s, 3H), 4.06 (s, 2H), 3.75 (s, 6H).

LCMS m/z: 322 $[M+H]^+$

Step C: Preparation of (E)-2-(3,5-dimethoxyphenyl)-3-(dimethylamino)-1-(2,4,6-trifluorphenyl)-2-propen-1-one To a mixture of 2-(3,5-dimethoxyphenyl)-1-(2,4,6-trifluorophenyl)ethanone (i.e. the product of Step B) (7.5 g, 24 mmol) in toluene (75 mL) was added 1,1-dimethoxy-N,N-dimethylmethanamine (4.3 g, 36 mmol). The reaction mixture was heated at 120° C. for 16 h, allowed to cool to room temperature and concentrated under reduced pressure. The resulting material was triturated with diethyl ether and n-pentane (30 mL: 90 mL). The precipitate was collected on a glass frit funnel to provide the title compound as a yellow solid (7.5 g).

$^1$H NMR ($CDCl_3$): δ 7.80 (br s, 1H), 6.60-6.20 (br m, 5H), 3.75-3.73 (two s, total 6H), 3.4-2.4 (br m, 6H).

LCMS m/z: 365 $[M+H]^+$

Step D: Preparation of 1,2-dihydro-5-(3,5-dimethoxyphenyl)-6-(2,4,6-trifluorophenyl)-2-oxo-3-pyridinecarbonitrile To a solution of sodium ethoxide (prepared from sodium (1 g, 41 mmol) and ethanol 75 mL) at 0° C. was added 2-cyanoacetamide (1.9 g, 22.59 mmol). The reaction mixture was stirred at room temperature for 1 h, and then a solution of (E)-2-(3,5-dimethoxyphenyl)-3-(dimethylamino)-1-(2,4,6-trifluorphenyl)-2-propen-1-one (i.e. the product of Step C) (7.5 g, 20.54 mmol) in ethanol (10 mL) was added. The reaction mixture was heated at reflux for 6 h, and then diluted with ice-cold water (100 mL) and extracted with ethyl acetate (3×250 mL). The combined organic extracts were washed with saturated aqueous sodium chloride solution, dried over sodium sulfate, filtered and concentrated under reduced pressure. The resulting material was purified by silica gel column chromatography (eluting with 0-50% ethyl acetate in petroleum ether) to provide the title compound as a white solid (3 g) melting at 290-293° C.

$^1$H NMR ($CDCl_3$): δ 8.01 (s, 1H), 6.75 (m, 2H), 6.37 (t, 1H), 6.19 (d, 2H), 3.69 (s, 6H).

LCMS m/z: 387 $[M+H]^+$

Step E: Preparation of 1,2-dihydro-5-(3,5-dimethoxyphenyl)-1-methyl-2-oxo-6-(2,4,6-trifluorophenyl)-3-pyridinecarbonitrile To a mixture of 1,2-dihydro-5-(3,5-dimethoxyphenyl)-6-(2,4,6-trifluorophenyl)-2-oxo-3-pyridinecarbonitrile (i.e. the product of Step C) (1.2 g, 3.1 mmol) in N,N-dimethylformamide (10 mL) was added potassium carbonate (0.85 g, 6.21 mmol), followed by iodomethane (4.66 mmol). After 4 h, the reaction mixture was diluted with ice-cold water (50 mL) and the resulting mixture was stirred for 30 minutes. The resulting solid precipitate was collected on a glass frit funnel, air-dried and then triturated with petroleum ether. The obtained solid was dried under reduced pressure to provide the title compound, a compound of the present invention, as a yellow solid (800 mg) melting at 180-183° C.

$^1$H NMR ($CDCl_3$): δ 7.87 (s, 1H), 6.71 (m, 2H), 6.33 (t, 1H), 6.15 (d, 2H), 3.69 (s, 6H), 3.43 (s, 3H).

LCMS m/z: 401 $[M+H]^+$

Example 28

Preparation of 5-(2-chloro-3,5-dimethoxyphenyl)-1,2-dihydro-1-methyl-2-oxo-6-(2,4,6-trifluorophenyl)-3-pyridinecarbonitrile (Compound 68) and 5-(4-chloro-3,5-dimethoxyphenyl)-1,2-dihydro-1-methyl-2-oxo-6-(2,4,6-trifluorophenyl)-3-pyridinecarbonitrile (Compound 71)

To a mixture of 1,2-dihydro-5-(3,5-dimethoxyphenyl)-1-methyl-2-oxo-6-(2,4,6-trifluorophenyl)-3-pyridinecarbonitrile (i.e. the product of Example 27) (530 mg, 1.32 mmol) in N,N-dimethylformamide (10 mL) at 0° C. was added N-chlorosuccinimide (176 mg, 1.32 mmol). The reaction mixture was heated at 60° C. for 6 h, and then diluted with ice-cold water (50 mL) and extracted with ethyl acetate (3×50 mL). The combined organic extracts were washed with saturated aqueous sodium chloride solution, dried over sodium sulfate, filtered and concentrated under reduced pressure. The resulting material was crystallized from methanol and water (2:1), and then purified by preparative HPLC to provide the title compounds, compounds of the present invention. Compound Number 68 was obtained as a white solid (215 mg) melting at 159-163° C.; and Compound Number 71 was obtained as a white solid (20 mg) melting at 223-227° C.

$^1$H NMR ($CDCl_3$): δ 7.80 (s, 1H), 6.64-6.73 (m, 2H), 6.41 (m, 1H), 6.16 (m, 2H), 3.84 (s, 3H), 3.68 (s, 3H), 3.44 (s, 3H).

LCMS m/z: 435 $[M+H]^+$ $^1$H NMR ($CDCl_3$): δ 7.89 (s, 1H), 6.73 (m, 2H), 6.25 (s, 2H), 3.78 (s, 6H), 3.44 (s, 3H).

LCMS m/z: 435 $[M+H]^+$

Example 29

Preparation of 5-chloro-1-(2-chloro-5-methoxyphenyl)-1,4-dihydro-6-(4-fluorophenyl)-4-oxo-3-pyridazinecarboxylic acid (Compound 104)

Step A: Preparation of ethyl (2E)-2-[2-(2-chloro-5-methoxyphenyl)hydrazinylidene]-3-oxobutanoate To hydrochloric acid (50 mL) at 0° C. was added 2-chloro-5-methoxybenzenamine hydrochloride (1:1, 5.00 g, 25.8 mmol). The reaction mixture was stirred for 15 minutes, and then a solution of sodium nitrite (2.04 g, 30.0 mmol) in water (20 mL) was added dropwise over 2 minutes.

In a separate reaction flask, ethyl acetoacetate (3.69 g, 28.3 mmol), sodium acetate (5.00 g) and ethanol (30 mL) were combined and cooled to 0° C., and then the above reaction mixture was added dropwise over 5 minutes. The reaction mixture was maintained at approximately pH 5 by the addition of sodium acetate (30 g). The reaction mixture was stirred overnight, and then filtered collecting a solid precipitate which was washed with water. The solid was dissolved in ethyl acetate, dried over magnesium sulfate, filtered and concentrated under reduced pressure to provide the title compound as a solid (7.18 g).

$^1$H NMR ($CDCl_3$): δ 7.28-7.24 (m, 2H), 6.64 (m, 1H), 4.41 (m, 2H), 3.84 (s, 3H), 2.51 (s, 3H), 1.43-1.39 (m, 3H).

Step B: Preparation of ethyl 1-(2-chloro-5-methoxyphenyl)-1,4-dihydro-4-oxo-3-pyridazinecarboxylate To ethyl (2E)-2-[2-(2-chloro-5-methoxyphenyl)hydrazinylidene]-3-oxobutanoate (i.e. the product of Step A) (7.18 g, 24.04 mmol) was added N,N-dimethylformamide dimethyl acetal (30 mL). The reaction mixture was heated at 70° C. overnight, cooled and concentrated under reduced pressure. The resulting material was purified by MPLC (eluting with a gradient of 0 to 100% ethyl acetate in hexanes) to provide the title compound as a solid (5.54 g).

$^1$H NMR ($CDCl_3$): δ 7.86 (d, 1H), 7.34 (d, 1H), 7.20 (d, 1H), 6.54 (m, 1H), 6.06 (d, 1H), 4.32 (m, 2H), 3.83 (s, 3H), 1.40 (m, 3H).

Step C: Preparation of ethyl 5-chloro-1-(2-chloro-5-methoxyphenyl)-1,4-dihydro-4-oxo-3-pyridazinecarboxylate To a mixture of ethyl 1-(2-chloro-5-methoxyphenyl)-1,4-dihydro-4-oxo-3-pyridazinecarboxylate (i.e. the product of Step B) (6.92 g, 22.4 mmol) in N,N-dimethylformamide (50 mL) was added N-chlorosuccinimide (3.00 g, 22.4 mmol). The reaction mixture was stirred overnight and then diluted with water and extracted with ethyl acetate (4×100 mL). The combined organic extracts were washed with water and saturated aqueous sodium chloride solution, dried over sodium sulfate, filtered and concentrated under reduced pressure. The resulting material was purified by MPLC (eluting with a gradient of 0 to 100% ethyl acetate in hexanes) to provide the title compound as a solid (5.54 g).

$^1$H NMR ($CDCl_3$): δ 8.23 (s, 1H), 7.44 (m, 1H), 7.05 (m, 1H), 7.02 (m, 1H), 4.45 (m, 2H), 3.86 (s, 3H), 1.40 (m, 3H).

Step D: Preparation of ethyl 5-chloro-1-(2-chloro-5-methoxyphenyl)-6-(4-fluorophenyl)-1,4-dihydro-4-oxo-3-pyridazinecarboxylate Combined 1-fluoro-4-iodobenzene (4.30 g, 19.4 mmol), tris(dibenzylideneacetone)-dipalladium (0.739 g, 0.807 mmol) and tri-2-furanylphosphine (0.375 g, 1.61 mmol) in tetrahydrofuran (25 mL) and stirred for 10 minutes.

In a separate reaction flask, zinc chloro 2,2,6,6-tetramethylpiperidide lithium chloride complex (0.7 M in tetrahydrofuran, 34.6 mL, 24.2 mmol), ethyl 5-chloro-1-(2-chloro-5-methoxyphenyl)-1,4-dihydro-4-oxo-3-pyridazinecarboxylate (i.e. the product of Step C) (5.54 g, 16.1 mmol) and tetrahydrofuran (35 mL) were combined and cooled to 0° C., stirred for 10 minutes, and then the above reaction mixture was added dropwise over 5 minutes. The reaction mixture was allowed to warm to room temperature and stirred for 1 h, and then concentrated under reduced pressure. The resulting material was purified by MPLC (eluting with a gradient of 20 to 100% ethyl acetate in hexanes) to provide the title compound as a solid (4.71 g).

$^1$H NMR ($CDCl_3$): δ 7.42-7.38 (m, 1H), 7.23-7.19 (m, 1H), 7.19-7.14 (m, 1H), 7.05-7.01 (m, 2H), 6.84-6.76 (m, 2H), 4.51-4.42 (m, 2H), 3.73 (s, 3H), 1.45-1.37 (m, 3H).

Step E: Preparation of 5-chloro-1-(2-chloro-5-methoxyphenyl)-1,4-dihydro-6-(4-fluorophenyl)-4-oxo-3-pyridazinecarboxylic Acid To a mixture of ethyl 5-chloro-1-(2-chloro-5-methoxyphenyl)-6-(4-fluorophenyl)-1,4-dihydro-4-oxo-3-pyridazinecarboxylate (i.e. the product of Step D) (3.05 g, 6.98 mmol) in methanol (30 mL) and water (30 mL) was added sodium hydroxide (50% aqueous solution, 2 mL). The reaction mixture was stirred for 3 h and then concentrated under reduced pressure to about 50% of the total volume. The resulting mixture was acidified by the addition of hydrochloric acid (1 N), and then extracted with ethyl acetate (3×50 mL). The combined organic extracts were dried over magnesium sulfate, filtered and concentrated to provide the title compound, a compound of the present invention, as a tan solid (2.48 g).

$^1$H NMR ($CDCl_3$): δ 7.50-7.43 (m, 1H), 7.25-7.17 (m, 2H), 7.11-7.04 (m, 3H), 6.86-6.83 (m, 1H), 3.75 (s, 3H).

Example 30

Preparation of 5-chloro-1-(2-chloro-5-methoxyphenyl)-1,4-dihydro-6-(4-fluorophenyl)-3-(hydroxymethyl)-4(1H)-pyridazinone (Compound 128)

To a mixture of 5-chloro-1-(2-chloro-5-methoxyphenyl)-1,4-dihydro-6-(4-fluorophenyl)-4-oxo-3-pyridazinecarboxylic acid (i.e. the product of Example 29) (2.44 g, 5.96 mmol) in tetrahydrofuran (10 mL) at 0° C. was added isobutyl chloroformate (1.22 g, 8.94 mmol), followed by N-methylmorpholine (1.31 mL, 1.21 g, 11.9 mmol). The reaction mixture was stirred at 0° C. for 30 minutes, and then a solution of sodium borohydride (0.271 g, 7.15 mmol) in water was added. After 30 minutes, the reaction mixture was diluted with a saturated aqueous solution of ammonium chloride and extracted with methylene chloride. The organic extract was dried over magnesium sulfate, filtered and concentrated under reduce pressure. The resulting material was purified by MPLC (eluting with a gradient of 30 to 100% ethyl acetate in hexanes) to provide the title compound, a compound of the present invention as a solid (1.13 g).

$^1$H NMR ($CDCl_3$): δ 7.42-7.35 (m, 1H), 7.25-7.17 (m, 2H), 7.06-7.00 (m, 2H), 6.83 (m, 1H), 6.80-6.73 (m, 1H), 4.91-4.79 (m, 2H), 3.74 (s, 3H).

Example 31

Preparation of 5-chloro-1-(2-chloro-5-methoxyphenyl)-6-(4-fluorophenyl)-3-methyl-4(1H)-pyridazinone (Compound 105)

Step A: Preparation of 5-chloro-1-(2-chloro-5-methoxyphenyl)-6-(4-fluorophenyl)-3-[[(methylsulfonyl)oxy]methyl]-4(1H)-pyridazinone To a mixture of 5-chloro-1-(2-chloro-5-methoxyphenyl)-1,4-dihydro-6-(4-fluorophenyl)-3-(hydroxymethyl)-4(1H)-pyridazinone (i.e. the product of Example 30) (1.13 g, 2.86 mmol) in methylene chloride (20 mL) at 0° C. was added triethylamine (0.318 g, 3.14 mmol) and methanesulfonyl chloride (0.36 g, 3.14 mmol). The reaction mixture was stirred at room temperature overnight and then concentrated under reduced pressure. The resulting material was purified by MPLC (eluting with a gradient of 0 to 100% ethyl acetate in hexanes) to provide the title compound as a tan solid (0.64 g).

$^1$H NMR ($CDCl_3$): δ 7.45-7.27 (m, 1H), 7.25-7.19 (m, 2H), 7.07-6.97-(m, 2H), 6.86-6.79 (m, 1H), 6.75 (d, 1H), 4.82-4.61 (m, 2H), 3.73 (s, 3H), 2.70-2.68 (m, 3H).

Step B: Preparation of ethyl 1-(2-chloro-5-methoxyphenyl)-1,4-dihydro-4-oxo-3-pyridazinecarboxylate To a mixture of 5-chloro-1-(2-chloro-5-methoxyphenyl)-6-(4-fluorophenyl)-3-[[(methylsulfonyl)oxy]methyl]-4(1H)-pyridazinone (i.e. the product of Step A) (0.576 g, 1.22 mmol) in dimethyl sulfoxide (5 mL) at 0° C. was added sodium borohydride (0.092 g, 2.43 mmol). The reaction mixture was stirred at room temperature for 2 h, and then diluted with water and extracted with ethyl acetate (3×50 mL). The combined organic extracts were dried over magnesium sulfate, filtered and concentrated under reduce pressure. The resulting material was purified by MPLC (eluting with a gradient of 0 to 100% ethyl acetate in hexanes) to provide a solid. The solid was recrystallized from methanol and diethyl ether to provide the title compound, a compound of the present invention as an off-white solid (235 mg) melting at 207-210° C.

$^1$H NMR ($CDCl_3$): δ 7.43-7.31 (m, 1H), 7.25-7.14 (m, 2H), 7.00 (m, 2H), 6.80 (m, 1H), 6.74 (m, 1H), 3.73 (s, 3H), 2.47 (s, 3H).

LCMS m/z: 379 $[M+H]^+$

Formulation/Utility

A compound of Formula 1 of this invention (including N-oxides and salts thereof), or a mixture (i.e. composition) comprising the compound with at least one additional fungicidal compound as described in the Summary of the Invention, will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

A compound of Formula 1, or mixture thereof, can be formulated in a number of ways, including:

(65) the compound of Formula 1 and optionally one or more other biologically active compounds or agents can be formulated separately and applied separately or applied simultaneously in an appropriate weight ratio, e.g., as a tank mix; or (ii) the compound of Formula 1 and optionally one or more other biologically active compounds or agents can be formulated together in the proper weight ratio.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* $2^{nd}$ Ed., Dorland Books, Caldwell, New Jersey.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* $2^{nd}$ Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 m can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, $4^{th}$ Ed., McGraw-Hill, New York, 1963, pp 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566. One embodiment of the present invention relates to a method for controlling fungal pathogens, comprising diluting the fungicidal composition of the present invention (a compound of Formula 1 formulated with surfactants, solid diluents and liquid diluents or a formulated mixture of a compound of Formula 1 and at least one other fungicide) with water, and optionally adding an adjuvant to form a diluted composition, and contacting the fungal pathogen or its environment with an effective amount of said diluted composition.

Although a spray composition formed by diluting with water a sufficient concentration of the present fungicidal composition can provide sufficient efficacy for controlling fungal pathogens, separately formulated adjuvant products can also be added to spray tank mixtures. These additional adjuvants are commonly known as "spray adjuvants" or "tank-mix adjuvants", and include any substance mixed in a spray tank to improve the performance of a pesticide or alter the physical properties of the spray mixture. Adjuvants can be anionic or nonionic surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

The amount of adjuvants added to spray mixtures is generally in the range of about 0.1% to 2.5% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet® (Helena Chemical Company) polyalkyleneoxide modified heptamethyltrisiloxane and Assist® (BASF) 17% surfactant blend in 83% paraffin based mineral oil.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1 and a film former or adhesive agent. Seeds can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9$^{th}$ International Congress on Pesticide Chemistry, The Royal Society of Chemistry, Cambridge, 1999, pp. 120-133. Also see U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8$^{th}$ Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Active ingredient refers to the compounds in Index Tables A-G disclosed herein. Without further elaboration, it is believed that one skilled in the art using the preceding description can utilize the present invention to its fullest extent. The following Examples are, therefore, to be constructed as merely illustrative, and not limiting of the disclosure in any way whatsoever.

Example A

| High Strength Concentrate | |
|---|---|
| Compound 33 | 98.5% |
| silica aerogel | 0.5% |
| synthetic amorphous fine silica | 1.0% |

Example B

| Wettable Powder | |
|---|---|
| Compound 29 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 26 | 10.0% |
| attapulgite granules (low volatile matter, 0.71/0.30 mm; U.S.S. No. 25-50 sieves) | 90.0% |

Example D

| Extruded Pellet | |
|---|---|
| Compound 48 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 49 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 54 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 55 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
|---|---|
| Compound 59 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

| Suspension Concentrate | |
|---|---|
| Compound 35 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| Compound 37 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| Compound 33 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| Compound 63 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Water-soluble and water-dispersible formulations are typically diluted with water to form aqueous compositions before application. Aqueous compositions for direct applications to the plant or portion thereof (e.g., spray tank compositions) typically contain at least about 1 ppm or more (e.g., from 1 ppm to 100 ppm) of the compound(s) of this invention.

Seed is normally treated at a rate of from about 0.001 g (more typically about 0.1 g) to about 10 g per kilogram of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Ascomycota, Basidiomycota, Zygomycota phyla, and the fungal-like Oomycota class. They are effective in controlling a broad spectrum of plant diseases, particularly foliar pathogens of ornamental, turf, vegetable, field, cereal, and fruit crops. These pathogens include but are not limited to those listed in Table 1-1. For Ascomycetes and Basidiomycetes, names for both the sexual/teleomorph/perfect stage as well as names for the asexual/anamorph/imperfect stage (in parentheses) are listed where known. Synonymous names for pathogens are indicated by an equal sign. For example, the sexual/teleomorph/perfect stage name Phaeosphaeria *nodorum* is followed by the corresponding asexual/anamorph/imperfect stage name Stagnospora *nodorum* and the synonymous older name *Septoria nodorum*.

TABLE 1-1

| |
|---|
| Ascomycetes in the order Pleosporales including *Alternaria solani*, *A. alternata* and *A. brassicae*, *Guignardia bidwellii*, *Venturia inaequalis*, *Pyrenophora tritici-repentis* (*Dreschlera tritici-repentis* = *Helminthosporium tritici-repentis*) and *Pyrenophora teres* (*Dreschlera teres* = *Helminthosporium teres*), *Corynespora cassiicola*, *Phaeosphaeria nodorum* (*Stagonospora nodorum* = *Septoria nodorum*), *Cochliobolus carbonum* and *C. heterostrophus*, *Leptosphaeria biglobosa* and *L. maculans*; |
| Ascomycetes in the order Mycosphaerellales including *Mycosphaerella graminicola* (*Zymoseptoria tritici* = *Septoria tritici*), *M. berkeleyi* (*Cercosporidium personatum*), *M. arachidis* (*Cercospora arachidicola*), *Passalora sojina* (*Cercospora sojina*), *Cercospora zeae-maydis* and *C. beticola*; |
| Ascomycetes in the order Erysiphales (the powdery mildews) such as *Blumeria graminis* f. sp. *tritici* and *Blumeria graminis* f. sp. *hordei*, *Erysiphe polygoni*, *E. necator* (=*Uncinula necator*), *Podosphaera fuliginea* (=*Sphaerotheca fuliginea*), and *Podosphaera leucotricha* (=*Sphaerotheca fuliginea*); |
| Ascomycetes in the order Helotiales such as *Botryotinia fuckeliana* (*Botrytis cinerea*), *Oculimacula yallundae* (=*Tapesia yallundae*; anamorph *Helgardia herpotrichoides* = *Pseudocercosporella herpetrichoides*), *Monilinia fructicola*, *Sclerotinia sclerotiorum*, *Sclerotinia minor*, and *Sclerotinia homoeocarpa*; |
| Ascomycetes in the order Hypocreales such as *Giberella zeae* (*Fusarium graminearum*), *G. monoliformis* (*Fusarium moniliforme*), *Fusarium solani* (=*Neocosmopora solani*) and *Verticillium* 109nocul; |
| Ascomycetes in the order Eurotiales such as *Aspergillus flavus* and *A. parasiticus*; |
| Ascomycetes in the order Diaporthales such as *Cryptosphorella viticola* (=*Phomopsis viticola*), *Phomopsis longicolla*, and *Diaporthe phaseolorum*; |
| Other Ascomycete pathogens including *Magnaporthe grisea*, *Gaeumannomyces graminis*, *Rhynchosporium secalis*, and anthracnose pathogens such as *Glomerella acutata* (*Colletotrichum acutatum*), *G. graminicola* (*C. graminicola*) and *G. lagenaria* (*C. orbiculare*); |
| Basidiomycetes in the order Urediniales (the rusts) including *Puccinia recondita*, *P. striiformis*, *Puccinia hordei*, *P. graminis* and *P. arachidis*), *Hemileia vastatrix* and *Phakopsora pachyrhizi*; |
| Basidiomycetes in the order Ceratobasidiales such as *Thanatophorum cucumeris* (*Rhizoctonia solani*) and *Ceratobasidium oryzae-sativae* (*Rhizoctonia oryzae*); |
| Basidiomycetes in the order Polyporales such as *Athelia rolfsii* (*Sclerotium rolfsii*); |
| Basidiomycetes in the order Ustilaginales such as *Ustilago maydis*; |
| Zygomycetes in the order Mucorales such as *Rhizopus stolonifer*; |
| Oomycetes in the order Pythiales, including *Phytophthora infestans*, *P. megasperma*, *P. parasitica*, *P. sojae*, *P. cinnamomi* and *P. capsici*, and *Pythium* pathogens such as *Pythium aphanidermatum*, *P. graminicola*, *P. irregulare*, *P. ultimum* and *P. dissoticum*; |
| Oomycetes in the order Peronosporales such as *Plasmopara viticola*, *P. halstedii*, *Peronospora hyoscyami* (=*Peronospora tabacina*), *P. manshurica*, *Hyaloperonospora parasitica* (=*Peronospora parasitica*), *Pseudoperonospora cubensis* and *Bremia lactucae*; |
| and other genera and species closely related to all of the above pathogens. |

In addition to their fungicidal activity, the compositions or combinations also have activity against bacteria such as *Erwinia amylovora, Xanthomonas campestris, Pseudomonas syringae*, and other related species. By controlling harmful microorganisms, the compounds of the invention are useful for improving (i.e. increasing) the ratio of beneficial to harmful microorganisms in contact with crop plants or their propagules (e.g., seeds, corms, bulbs, tubers, cuttings) or in the agronomic environment of the crop plants or their propagules. Compounds of the invention are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance.

Treatment of genetically modified plants and seeds with compounds of the invention may result in super-additive or enhanced effects. For example, reduction in application rates, broadening of the activity spectrum, increased tolerance to biotic/abiotic stresses or enhanced storage stability may be greater than expected from just simple additive effects of the application of compounds of the invention on genetically modified plants and seeds.

Compounds of this invention are useful in seed treatments for protecting seeds from plant diseases. In the context of the present disclosure and claims, treating a seed means contacting the seed with a biologically effective amount of a compound of this invention, which is typically formulated as a composition of the invention. This seed treatment protects the seed from soil-borne disease pathogens and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with compounds of this invention can also increase vigor of plants growing from the seed.

Compounds of this invention and their compositions, both alone and in combination with other fungicides, nematicides and insecticides, are particularly useful in seed treatment for crops including, but not limited to, maize or corn, soybeans, cotton, cereal (e.g., wheat, oats, barley, rye and rice), potatoes, vegetables and oilseed rape.

Furthermore, the compounds of this invention are useful in treating postharvest diseases of fruits and vegetables caused by fungi, oomycetes and bacteria. These infections can occur before, during and after harvest. For example, infections can occur before harvest and then remain dormant until some point during ripening (e.g., host begins tissue changes in such a way that infection can progress or conditions become conducive for disease development); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g., fruits, seeds, foliage, stems, bulbs, tubers) can be stored refrigerated or un-refrigerated after harvest, and remain edible and free from noticeable or harmful degradation or contamination by fungi or other microorganisms. Treatment of edible plant parts before or after harvest with compounds of the invention can also decrease the formation of toxic metabolites of fungi or other microorganisms, for example, mycotoxins such as aflatoxins.

Plant disease control is ordinarily accomplished by applying an effective amount of a compound of this invention either pre- or post-infection, to the portion of the plant to be protected such as the roots, stems, foliage, fruits, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants. Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

The compounds can also be applied using an unmanned aerial vehicle (UAV) for the dispension of the compositions disclosed herein over a planted area. In some embodiments the planted area is a crop-containing area. In some embodiments, the crop is selected from a monocot or dicot. In some embodiments, the crop is selected form rice, corn, barley, sobean, wheat, vegetable, tobacco, tea tree, fruit tree and sugar cane. In some embodiments, the compositions disclosed herein are formulated for spraying at an ultra-low volume. Products applied by drones may use water or oil as the spray carrier. Typical spray volume (including product) used for drone applications globally is 5.0 liters/ha-100 liters/ha (approximately 0.5-10 gpa). This includes the range of ultra low spray volume (ULV) to low spray volume (LV). Although not common there may be situations where even lower spray volumes could be used as low as 1.0 liter/ha (0.1 gpa).

Suitable rates of application for the compounds of this invention (i.e. a fungicidally effective amount) can be influenced by factors such as the plant diseases to be controlled, the plant species to be protected, the population structure of the pathogen to be controlled, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.001 g (more typically about 0.1 g) to about 10 g per kilogram of seed. One skilled in the art can easily determine through simple experimentation the application rates for the compounds of this invention, and compositions thereof, needed to provide the desired spectrum of plant protection and control of plant diseases and optionally other plant pests.

Compounds of the present invention may also be useful for increasing vigor of a crop plant. This method comprises contacting the crop plant (e.g., foliage, flowers, fruit or roots) or the seed from which the crop plant is grown with a compound of Formula 1 in amount sufficient to achieve the desired plant vigor effect (i.e. biologically effective amount). Typically the compound of Formula 1 is applied in a formulated composition. Although the compound of Formula 1 is often applied directly to the crop plant or its seed, it can also be applied to the locus of the crop plant, i.e. the environment of the crop plant, particularly the portion of the environment in close enough proximity to allow the compound of Formula 1 to migrate to the crop plant. The locus relevant to this method most commonly comprises the growth medium (i.e. medium providing nutrients to the plant), typically soil in which the plant is grown. Treatment of a crop plant to increase vigor of the crop plant thus comprises contacting the crop plant, the seed from which the crop plant is grown or the locus of the crop plant with a biologically effective amount of a compound of Formula 1.

Increased crop vigor can result in one or more of the following observed effects: (a) optimal crop establishment as demonstrated by excellent seed germination, crop emergence and crop stand; (b) enhanced crop growth as demonstrated by rapid and robust leaf growth (e.g., measured by leaf area index), plant height, number of tillers (e.g., for rice), root mass and overall dry weight of vegetative mass of the crop; (c) improved crop yields, as demonstrated by time to flowering, duration of flowering, number of flowers, total biomass accumulation (i.e. yield quantity) and/or fruit or grain grade marketability of produce (i.e. yield quality); (d) enhanced ability of the crop to withstand or prevent plant disease infections and arthropod, nematode or mollusk pest infestations; and I increased ability of the crop to withstand environmental stresses such as exposure to thermal extremes, suboptimal moisture or phytotoxic chemicals.

The compounds of the present invention may increase the vigor of treated plants compared to untreated plants by preventing and/or curing plant diseases caused by fungal plant pathogens in the environment of the plants. In the absence of such control of plant diseases, the diseases reduce plant vigor by consuming plant tissues or sap, or transmitting plant pathogens such as viruses. Even in the absence of fungal plant pathogens, the compounds of the invention may increase plant vigor by modifying metabolism of plants. Generally, the vigor of a crop plant will be most significantly increased by treating the plant with a compound of the invention if the plant is grown in a nonideal environment, i.e. an environment comprising one or more aspects adverse to the plant achieving the full genetic potential it would exhibit in an ideal environment.

Of note is a method for increasing vigor of a crop plant wherein the crop plant is grown in an environment comprising plant diseases caused by fungal plant pathogens. Also of note is a method for increasing vigor of a crop plant wherein the crop plant is grown in an environment not comprising plant diseases caused by fungal plant pathogens. Also of note is a method for increasing vigor of a crop plant wherein the crop plant is grown in an environment comprising an amount of moisture less than ideal for supporting growth of the crop plant.

Compounds of this invention can also be mixed with one or more other biologically active compounds or agents including fungicides, insecticides, nematicides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

As mentioned in the Summary of the Invention, one aspect of the present invention is a fungicidal composition comprising (i.e. a mixture or combination of) a compound of Formula 1, an N-oxide, or a salt thereof (i.e. component a), and at least one other fungicide (i.e. component b). Of note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a fungicidally effective amount of at least one additional fungicidal active ingredient having a similar spectrum of control but a different site of action.

Of note is a composition which in addition to the Formula 1 compound of component (a), includes as component (b) at least one fungicidal compound selected from the group consisting of the FRAC-defined mode of action (MOA) classes, including (A) nucleic acids metabolism, (B) cytoskeleton and motor protein, (C) respiration, (D) amino acids and protein synthesis, (E) signal transduction, (F) lipid synthesis or transport and membrane integrity or function, (G) sterol biosynthesis in membranes, (H) cell wall biosynthesis, (I) melanin synthesis in cell wall, (P) host plant defense induction, (U) unknown mode of action, (M) chemicals with multi-site activity and (BM) biologicals with multiple modes of action.

FRAC-recognized or proposed target sites of action along with their FRAC target site codes belonging to the above MOA classes are (A1) RNA polymerase I, (A2) adenosine deaminase, (A3) DNA/RNA synthesis (proposed), (A4) DNA topoisomerase type II (gyrase), (B1)-(B3) B-tubulin assembly in mitosis, (B4) cell division (unknown site), (B5) delocalization of spectrin-like proteins, (B6) actin/myosin/fimbrin function, (C1) complex I NADH odxido-reductase, (C2) complex II: succinate dehydrogenase, (C3) complex III: cytochrome bc1 (ubiquinol oxidase) at Qo site, (C4) complex III: cytochrome bc1 (ubiquinone reductase) at Qi site, (C5) uncouplers of oxidative phosphorylation, (C6) inhibitors of oxidative phosphorylation, ATP synthase, (C7) ATP production (proposed), (C8) complex III: cytochrome bc1 (ubiquinone reductase) at Qo site, stigmatellin binding sub-site (D1) methionine biosynthesis (proposed), (D2) protein synthesis (ribosome, termination step), (D3) protein synthesis (ribosome, initiation step), (D4) protein synthesis (ribosome, initiation step), (D5) protein synthesis (ribosome, elongation step), (E1) signal transduction (mechanism unknown), (E2)-(E3) MAP/histidine kinase in osmotic signal transduction, (F2) phospholipid biosynthesis, methyl transferase, (F3) cell peroxidation (proposed), (F4) cell membrane permeability, fatty acids (proposed), (F6) microbial disrupters of pathogen cell membranes, (F7) cell membrane disruption, (F8) ergosterol binding, (F9) lipid homeostasis and transfer/storage, (G1) C14-demethylase in sterol biosynthesis, (G2) A14-reductase and $\Delta 8 \rightarrow \Delta 7$-isomerase in sterol biosynthesis, (G3) 3-keto reductase, C4-demethylation, (G4) squalene epoxidase in sterol biosynthesis, (H4) chitin synthase, (H5) cellulose synthase, (I1) reductase in melanin biosynthesis, (I2) dehydratase in melanin biosynthesis, (I3) polyketide synthase in melanin biosynthesis, (P1)-(P3) salicylate-related, (P4) polysaccharide elicitors, (P5) anthraquinone elicitors, (P6) microbial elicitors, (P7) phosphonates, (BM01) plant extract, and (BM02) microbial, living microbes or extract, metabolites.

Of note is a composition which in addition to the Formula 1 compound of component (a), includes as component (b) at least one fungicidal compound selected from the group consisting of the classes (b1) methyl benzimidazole carbamate (MBC) fungicides; (b2) dicarboximide fungicides; (b3) demethylation inhibitor (DMI) fungicides; (b4) phenylamide (PA) fungicides; (b5) amine/morpholine fungicides; (b6) phospholipid biosynthesis inhibitor fungicides; (b7) succinate dehydrogenase inhibitor (SDHI) fungicides; (b8) hydroxy(2-amino-)pyrimidine fungicides; (b9) anilinopyrimidine (AP) fungicides; (b10) N-phenyl carbamate fungicides; (b11) quinone outside inhibitor (QoI) fungicides; (b12) phenylpyrrole (PP) fungicides; (b13) azanaphthalene fungicides; (b14) cell peroxidation inhibitor fungicides; (b15) melanin biosynthesis inhibitor-reductase (MBI-R)

fungicides; (b16a) melanin biosynthesis inhibitor-dehydratase (MBI-D) fungicides; (b16b) melanin biosynthesis inhibitor-polyketide synthase (MBI-P) fungicides; (b17) keto reductase inhibitor (KRI) fungicides; (b18) squalene-epoxidase inhibitor fungicides; (b19) polyoxin fungicides; (b20) phenylurea fungicides; (b21) quinone inside inhibitor (QiI) fungicides; (b22) benzamide and thiazole carboxamide fungicides; (b23) enopyranuronic acid antibiotic fungicides; (b24) hexopyranosyl antibiotic fungicides; (b25) glucopyranosyl antibiotic: protein synthesis fungicides; (b26) glucopyranosyl antibiotic fungicides; (b27) cyanoacetamideoxime fungicides; (b28) carbamate fungicides; (b29) oxidative phosphorylation uncoupling fungicides; (b30) organo tin fungicides; (b31) carboxylic acid fungicides; (b32) heteroaromatic fungicides; (b33) phosphonate fungicides; (b34) phthalamic acid fungicides; (b35) benzotriazine fungicides; (b36) benzene-sulfonamide fungicides; (b37) pyridazinone fungicides; (b38) thiophene-carboxamide fungicides; (b39) complex I NADH oxido-reductase inhibitor fungicides; (b40) carboxylic acid amide (CAA) fungicides; (b41) tetracycline antibiotic fungicides; (b42) thiocarbamate fungicides; (b43) benzamide fungicides; (b44) microbial fungicides; (b45) quinone outside inhibitor, stigmatellin binding (QoSI) fungicides; (b46) plant extract fungicides; (b47) cyanoacrylate fungicides; (b48) polyene fungicides; (b49) oxysterol binding protein inhibitor (OSBPI) fungicides; (b50) aryl-phenyl-ketone fungicides; (b51) host plant defense induction fungicides; (b52) multi-site activity fungicides; (b53) biologicals with multiple modes of action; (b54) fungicides other than fungicides of component (a) and components (b1) through (b53); and salts of compounds of (b1) through (b54).

Also of note are embodiments wherein component (b) comprises at least one fungicidal compound from each of two different groups selected from (b1) through (b54).

Further descriptions of groups (b1) through (b54) are as follows.

(b1) "Methyl benzimidazole carbamate (MBC) fungicides" (FRAC code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(b2) "Dicarboximide fungicides" (FRAC code 2) inhibit a mitogen-activated protein (MAP)/histidine kinase in osmotic signal transduction. Examples include chlozolinate, dimethachlone, iprodione, procymidone and vinclozolin.

(b3) "Demethylation inhibitor (DMI) fungicides" (FRAC code 3) (Sterol Biosynthesis Inhibitors (SBI): Class I) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: piperazines, pyridines, pyrimidines, imidazoles, triazoles and triazolinthiones. The piperazines include triforine. The pyridines include buthiobate, pyrifenox, pyrisoxazole and (αS)-[3-(4-chloro-2-fluorophenyl)-5-(2,4-difluorophenyl)-4-isoxazolyl]-3-pyridinemethanol. The pyrimidines include fenarimol, nuarimol and triarimol. The imidazoles include econazole, imazalil, oxpoconazole, pefurazoate, prochloraz and triflumizole. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, ipfentrifluconazole, mefentrifluconazole, metconazole, myclobutanil, penconazole, propiconazole, quinconazole, simeconazole, tebuconazole, tetraconazole, triadimefon, triadimenol, triticonazole, uniconazole, uniconazole-β,α-(1-chlorocyclopropyl)-α-[2-(2,2-dichlorocyclopropyl)ethyl]-1H-1,2,4-triazole-1-ethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione and rel-1-[[(2R,3S)-3-(2-chlorophenyl)-2-(2,4-difluorophenyl)-2-oxiranyl]methyl]-5-(2-propen-1-ylthio)-1H-1,2,4-triazole. The triazolinthiones include prothioconazole. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(b4) "Phenylamide fungicides" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M (also known as kiralaxyl), furalaxyl, metalaxyl and metalaxyl-M (also known as mefenoxam). The oxazolidinones include oxadixyl. The butyrolactones include ofurace.

(b5) "Amine/morpholine fungicides" (FRAC code 5) (SBJ: Class II) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(b6) "Phospholipid biosynthesis inhibitor fungicides" (FRAC code 6) inhibit growth of fungi by affecting phospholipid biosynthesis. Phospholipid biosynthesis fungicides include phophorothiolate and dithiolane fungicides. The phosphorothiolates include edifenphos, iprobenfos and pyrazophos. The dithiolanes include isoprothiolane.

(b7) "Succinate dehydrogenase inhibitor (SDHI) fungicides" (FRAC code 7) inhibit complex II fungal respiration by disrupting a key enzyme in the Krebs Cycle (TCA cycle) named succinate dehydrogenase. Inhibiting respiration prevents the fungus from making ATP, and thus inhibits growth and reproduction. SDHI fungicides include phenylbenzamide, phenyloxoethylthiophene amide, pyridinylethylbenzamide, phenylcyclobutylpyridineamide, furan carboxamide, oxathiin carboxamide, thiazole carboxamide, pyrazole-4-carboxamide, N-cyclopropyl-N-benzyl-pyrazole carboxamide, N-methoxy-(phenyl-ethyl)-pyrazole carboxamide, pyridine carboxamide and pyrazine carboxamide fungicides. The phenylbenzamides include benodanil, flutolanil and mepronil. The phenyloxoethylthiophene amides include isofetamid. The pyridinylethylbenzamides include fluopyram. The phenylcyclobutylpyridineamide include cyclobutrifluram. The furan carboxamides include fenfuram. The oxathiin carboxamides include carboxin and oxycarboxin. The thiazole carboxamides include thifluzamide. The pyrazole-4-carboxamides include benzovindiflupyr, bixafen, flubeneteram (provisional common name, Registry Number 1676101-39-5), fluindapyr, fluxapyroxad, furametpyr, inpyrfluxam, isopyrazam, penflufen, penthiopyrad, pyrapropoyne (provisional common name, Registry Number 1803108-03-3), sedaxane and N-[2-(2,4-dichlorophenyl)-2-methoxy-1-methylethyl]-3-(difluoromethyl)-1-methyl-1H-pyrazole-4-carboxamide. The N-cyclopropyl-N-benzyl-pyrazole carboxamides include isoflucypram. The N-methoxy-(phenyl-ethyl)-pyrazole carboxamides include pydiflumetofen. The pyridine carboxamides include boscalid. The pyrazine carboxamides include pyraziflumid.

(b8) "Hydroxy-(2-amino-)pyrimidine fungicides" (FRAC code 8) inhibit nucleic acid synthesis by interfering with adenosine deaminase. Examples include bupirimate, dimethirimol and ethirimol.

(b9) "Anilinopyrimidine fungicides" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(b10) "N-Phenyl carbamate fungicides" (FRAC code 10) inhibit mitosis by binding to 3-tubulin and disrupting microtubule assembly. Inhibition of microtubule assembly can disrupt cell division, transport within the cell and cell structure. Examples include diethofencarb.

(b11) "Quinone outside inhibitor (QoI) fungicides" (FRAC code 11) inhibit complex III mitochondrial respiration in fungi by affecting ubiquinol oxidase. Oxidation of ubiquinol is blocked at the "quinone outside" (Qo) site of the cytochrome $bc_1$ complex, which is located in the inner mitochondrial membrane of fungi. Inhibiting mitochondrial respiration prevents normal fungal growth and development. Quinone outside inhibitor fungicides include methoxyacrylate, methoxyacetamide, methoxycarbamate, oximinoacetate, oximinoacetamide and dihydrodioxazine fungicides (collectively also known as strobilurin fungicides), and oxazolidinedione, imidazolinone and benzylcarbamate fungicides. The methoxyacrylates include azoxystrobin, coumoxystrobin, enoxastrobin (also known as enestroburin), flufenoxystrobin, picoxystrobin and pyraoxystrobin. The methoxyacetamides include mandestrobin. The methoxycarbamates include pyraclostrobin, pyrametostrobin and triclopyricarb. The oximinoacetates include kresoxim-methyl and trifloxystrobin. The oximinoacetamides include dimoxystrobin, fenaminstrobin, metominostrobin and orysastrobin. The dihydrodioxazines include fluoxastrobin. The oxazolidinediones include famoxadone. The imidazolinones include fenamidone. The benzylcarbamates include pyribencarb.

(b12) "Phenylpyrrole fungicides" (FRAC code 12) inhibit a MAP/histidine kinase associated with osmotic signal transduction in fungi. Fenpiclonil and fludioxonil are examples of this fungicide class.

(b13) "Azanaphthalene fungicides" (FRAC code 13) are proposed to inhibit signal transduction by a mechanism which is as yet unknown. They have been shown to interfere with germination and/or appressorium formation in fungi that cause powdery mildew diseases. Azanaphthalene fungicides include aryloxyquinolines and quinazolinones. The aryloxyquinolines include quinoxyfen. The quinazolinones include proquinazid.

(b14) "Lipid peroxidation inhibitor fungicides" (FRAC code 14) are proposed to inhibit lipid peroxidation which affects membrane synthesis in fungi. Members of this class, such as etridiazole, may also affect other biological processes such as respiration and melanin biosynthesis. Cell peroxidation fungicides include aromatic hydrocarbon and 1,2,4-thiadiazole fungicides. The aromatic hydrocarboncarbon fungicides include biphenyl, chloroneb, dicloran, quintozene, tecnazene and tolclofos-methyl. The 1,2,4-thiadiazoles include etridiazole.

(b15) "Melanin biosynthesis inhibitors-reductase (MBI-R) fungicides" (FRAC code 16.1) inhibit the naphthal reduction step in melanin biosynthesis. Melanin is required for host plant infection by some fungi. Melanin biosynthesis inhibitor-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(b16a) "Melanin biosynthesis inhibitors-dehydratase (MBI-D) fungicides" (FRAC code 16.2) inhibit scytalone dehydratase in melanin biosynthesis. Melanin is required for host plant infection by some fungi. Melanin biosynthesis inhibitor-dehydratase fungicides include cyclopropanecarboxamide, carboxamide and propionamide fungicides. The cyclopropanecarboxamides include carpropamid. The carboxamides include diclocymet. The propionamides include fenoxanil.

(b16b) "Melanin biosynthesis inhibitor-polyketide synthase (MBI-P) fungicides" (FRAC code 16.3) inhibit polyketide synthase in melanin biosynthesis. Melanin is required for host plant infection by some fungi. Melanin biosynthesis inhibitor-polyketide synthase fungicides include trifluoroethylcarbamate fungicides. The trifluoroethylcarbamates include tolprocarb.

(b17) "Sterol Biosynthesis Inhibitor (SBI): Class III fungicides (FRAC code 17) inhibit 3-keto reductase during C4-demethylation in sterol production. Keto reductase inhibitor fungicides (also known as Sterol Biosynthesis Inhibitors (SBI): Class III) include hydroxyanilides and amino-pyrazolinones. Hydroxyanilides include fenhexamid. Amino-pyrazolinones include fenpyrazamine. Quinofumelin (provisional common name, Registry Number 861647-84-9) and ipflufenoquin (provisional common name, Registry Number 1314008-27-9) are also believed to be keto reductase inhibitor fungicides.

(b18) "Squalene-epoxidase inhibitor fungicides" (FRAC code 18) (SBI: Class IV) inhibit squalene-epoxidase in the sterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(b19) "Polyoxin fungicides" (FRAC code 19) inhibit chitin synthase. Examples include polyoxin.

(b20) "Phenylurea fungicides" (FRAC code 20) are proposed to affect cell division. Examples include pencycuron.

(b21) "Quinone inside inhibitor (QiI) fungicides" (FRAC code 21) inhibit complex III mitochondrial respiration in fungi by affecting ubiquinone reductase. Reduction of ubiquinone is blocked at the "quinone inside" (Qi) site of the cytochrome $bc_i$ complex, which is located in the inner mitochondrial membrane of fungi. Inhibiting mitochondrial respiration prevents normal fungal growth and development.

Quinone inside inhibitor fungicides include cyanoimidazole, sulfamoyltriazole and picolinamide fungicides. The cyanoimidazoles include cyazofamid. The sulfamoyltriazoles include amisulbrom. The picolinamides include fenpicoxamid (Registry Number 517875-34-2).

(b22) "Benzamide and thiazole carboxamide fungicides" (FRAC code 22) inhibit mitosis by binding to β-tubulin and disrupting microtubule assembly. Inhibition of microtubule assembly can disrupt cell division, transport within the cell and cell structure. The benzamides include toluamides such as zoxamide. The thiazole carboxamides include ethylaminothiazole carboxamides such as ethaboxam.

(b23) "Enopyranuronic acid antibiotic fungicides" (FRAC code 23) inhibit growth of fungi by affecting protein biosynthesis. Examples include blasticidin-S.

(b24) "Hexopyranosyl antibiotic fungicides" (FRAC code 24) inhibit growth of fungi by affecting protein biosynthesis. Examples include kasugamycin.

(b25) "Glucopyranosyl antibiotic: protein synthesis fungicides" (FRAC code 25) inhibit growth of fungi by affecting protein biosynthesis. Examples include streptomycin.

(b26) "Glucopyranosyl antibiotic fungicides" (FRAC code U18, previously FRAC code 26 reclassified to U18) are proposed to inhibit trehalase and inositol biosynthesis. Examples include validamycin.

(b27) "Cyanoacetamideoxime fungicides (FRAC code 27) include cymoxanil.

(b28) "Carbamate fungicides" (FRAC code 28) are considered multi-site inhibitors of fungal growth. They are proposed to interfere with the synthesis of fatty acids in cell membranes, which then disrupts cell membrane permeability. Iodocarb, propamacarb and prothiocarb are examples of this fungicide class.

(b29) "Oxidative phosphorylation uncoupling fungicides" (FRAC code 29) inhibit fungal respiration by uncoupling oxidative phosphorylation. Inhibiting respiration prevents normal fungal growth and development. This class includes 2,6-dinitroanilines such as fluazinam, and dinitrophenyl crotonates such as dinocap, meptyldinocap and binapacryl.

(b30) "Organo tin fungicides" (FRAC code 30) inhibit adenosine triphosphate (ATP) synthase in oxidative phosphorylation pathway. Examples include fentin acetate, fentin chloride and fentin hydroxide.

(b31) "Carboxylic acid fungicides" (FRAC code 31) inhibit growth of fungi by affecting deoxyribonucleic acid (DNA) topoisomerase type II (gyrase). Examples include oxolinic acid.

(b32) "Heteroaromatic fungicides" (FRAC code 32) are proposed to affect DNA/ribonucleic acid (RNA) synthesis. Heteroaromatic fungicides include isoxazoles and isothiazolones. The isoxazoles include hymexazole and the isothiazolones include octhilinone.

(b33) "Phosphonate fungicides" (FRAC code P07, previously FRAC code 33 reclassified to P07) include phosphorous acid and its various salts, including fosetyl-aluminum.

(b34) "Phthalamic acid fungicides" (FRAC code 34) include teclofthalam.

(b35) "Benzotriazine fungicides" (FRAC code 35) include triazoxide.

(b36) "Benzene-sulfonamide fungicides" (FRAC code 36) include flusulfamide.

(b37) "Pyridazinone fungicides" (FRAC code 37) include diclomezine.

(b38) "Thiophene-carboxamide fungicides" (FRAC code 38) are proposed to affect ATP production. Examples include silthiofam.

(b39) "Complex I NADH oxidoreductase inhibitor fungicides" (FRAC code 39) inhibit electron transport in mitochondria and include pyrimidinamines such as diflumetorim, pyrazole-5-carboxamides such as tolfenpyrad, and quinazoline such as fenazaquin.

(b40) "Carboxylic acid amide (CAA) fungicides" (FRAC code 40) inhibit cellulose synthase which prevents growth and leads to death of the target fungus. Carboxylic acid amide fungicides include cinnamic acid amide, valinamide carbamate and mandelic acid amide fungicides. The cinnamic acid amides include dimethomorph, flumorph and pyrimorph. The valinamide carbamates include benthiavalicarb, benthiavalicarb-isopropyl, iprovalicarb, tolprocarb and valifenalate (also known as valiphenal). The mandelic acid amides include mandipropamid, N-[2-[4-[[3-(4-chlorophenyl)-2-propyn-1-yloxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(b41) "Tetracycline antibiotic fungicides" (FRAC code 41) inhibit growth of fungi by affecting protein synthesis. Examples include oxytetracycline.

(b42) "Thiocarbamate fungicides" (FRAC code M12, previously FRAC code 42 reclassified to M12) include methasulfocarb.

(b43) "Benzamide fungicides" (FRAC code 43) inhibit growth of fungi by delocalization of spectrin-like proteins. Examples include pyridinylmethyl benzamides such as fluopicolide and fluopimomide.

(b44) "Microbial fungicides" (FRAC code BM02, previously FRAC code 44 reclassified to BM02) disrupt fungal pathogen cell membranes. Microbial fungicides include *Bacillus* species such as *Bacillus amyloliquefaciens* strains AP-136, AP-188, AP-218, AP-219, AP-295, QST713, FZB24, F727, MB1600, D747, TJ100 (also called strain 1 BE; known from EP2962568), and the fungicidal lipopeptides which they produce.

(b45) "Quinone outside inhibitor, stigmatellin binding (QoSI) fungicides" (FRAC code 45) inhibit complex III mitochondrial respiration in fungi by affecting ubiquinone reductase at the "quinone outside" (Qo) site, stigmatellin binding sub-site, of the cytochrome $bc_i$ complex. Inhibiting mitochondrial respiration prevents normal fungal growth and development. QoSI fungicides include triazolopyrimidylamines such as ametoctradin.

(b46) "Plant extract fungicides" (FRAC code 46) cause cell membrane disruption. Plant extract fungicides include terpene hydrocarbons, terpene alcohols and terpen phenols such as the extract from *Melaleuca* alternifolia (tea tree) and plant oils (mixtures) such as eugenol, geraniol and thymol.

(b47) "Cyanoacrylate fungicides" (FRAC code 47) bind to the myosin motor domain and effect motor activity and actin assembly. Cyanoacrylates include fungicides such as phenamacril.

(b48) "Polyene fungicides" (FRAC code 48) cause disruption of the fungal cell membrane by binding to ergosterol, the main sterol in the membrane. Examples include natamycin (pimaricin).

(b49) "Oxysterol binding protein inhibitor (OSBPI) Fungicides" (FRAC code 49) bind to the oxysterol-binding protein in oomycetes causing inhibition of zoospore release, zoospore motility and sporangia germination. Oxysterol binding fungicides include piperdinylthiazoleisoxazolines such as oxathiapiprolin and fluoxapiprolin.

(b50) "Aryl-phenyl-ketone fungicides" (FRAC code 50, previously FRAC code U8 reclassified to 50) inhibit the growth of mycelium in fungi. Aryl-phenyl ketone fungicides include benzophenones such as metrafenone, and benzoylpyridines such as pyriofenone.

(b51) "Host plant defense induction fungicides" induce host plant defense mechanisms. Host plant defense induction fungicides include benzothiadiazole (FRAC code P01), benzisothiazole (FRAC code P02), thiadiazole carboxamide (FRAC code P03), polysaccharide (FRAC code P04), plant extract (FRAC code P05), microbial (FRAC code P06) and phosphonate fungicides (FRAC code P07, see (b33) above). The benzothiadiazoles include acibenzolar-S-methyl. The benzisothiazoles include probenazole. The thiadiazole carboxamides include tiadinil and isotianil. The polysaccharides include laminarin. The plant extracts include extract from *Reynoutria sachalinensis* (giant knotweed). The microbials include *Bacillus mycoides* isolate J and cell walls of *Saccharomyces cerevisiae* strain LAS117.

(b52) "Multi-site activity fungicides" inhibit fungal growth through multiple sites of action and have contact/preventive activity. Multi-site activity fungicides include copper fungicides (FRAC code M01), sulfur fungicides (FRAC code M02), dithiocarbamate fungicides (FRAC code M03), phthalimide fungicides (FRAC code M04), chloronitrile fungicides (FRAC code M05), sulfamide fungicides (FRAC code M06), multi-site contact guanidine fungicides (FRAC code M07), triazine fungicides (FRAC code M08), quinone fungicides (FRAC code M09), quinoxaline fungicides (FRAC code M10), maleimide fungicides (FRAC code M11) and thiocarbamate (FRAC code M12, see (b42) above) fungicides. Copper fungicides are inorganic compounds containing copper, typically in the copper(II) oxidation state; examples include copper oxychloride, copper sulfate and copper hydroxide, including compositions such as Bordeaux mixture (tribasic copper sulfate). Sulfur fungicides are inorganic chemicals containing rings or chains of sulfur atoms; examples include elemental sulfur. Dithiocarbamate fungicides contain a dithiocarbamate molecular moiety; examples include ferbam, mancozeb, maneb, metiram, propineb, thiram, zinc thiazole, zineb and ziram. Phthalimide fungicides contain a phthalimide molecular moiety; examples include folpet, captan and captafol. Chloronitrile fungicides contain an aromatic ring substituted with chloro and cyano; examples include chlorothalonil. Sulfamide fungicides include dichlofluanid and tolyfluanid. Multi-site contact guanidine fungicides include, guazatine, iminoctadine albesilate and iminoctadine triacetate. Triazine fungicides include anilazine. Quinone fungicides include dithianon. Quinoxaline fungicides include quinomethionate (also known as chinomethionate). Maleimide fungicides include fluoroimide.

(b53) "Biologicals with multiple modes of action" include agents from biological origins showing multiple mechanisms of action without evidence of a dominating mode of action. This class of fungicides includes polypeptide (lectin), phenol, sesquiterpene, tritepenoid and coumarin fungicides (FRAC code BM01) such as extract from the cotyledons of lupine plantlets. This class also includes momicrobial fungicides (FRAC code BM02, see (b44) above).

(b54) "Fungicides other than fungicides of component (a) and components (b1) through (b53)"; include certain fungicides whose mode of action may be unknown. These include: (b54.1) "phenyl-acetamide fungicides" (FRAC code U06), (b54.2) "guanidine fungicides" (FRAC code U12), (b54.3) "thiazolidine fungicides" (FRAC code U13), (b54.4) "pyrimidinone-hydrazone fungicides" (FRAC code U14), (b54.5) "4-quinolylacetate fungicides" (FRAC code U16), (54.6) "tetrazolyloxime fungicides" (FRAC code U17) and "glucopyranosyl antibiotic fungicides" (FRAC code U18, see (b26) above). The phenyl-acetamides include cyflufenamid. The guanidines include dodine. The thiazolidines include flutianil. The pyrimidinonehydrazones include ferimzone. The 4-quinolylacetates include tebufloquin. The tetrazolyloximes include picarbutrazox.

The (b54) class also includes bethoxazin, dichlobentiazox (provisional common name, Registry Number 957144-77-3), dipymetitrone (provisional common name, Registry Number 16114-35-5), flometoquin, neo-asozin (ferric methanearsonate), pyrrolnitrin, tolnifanide (Registry Number 304911-98-6), N'-[4-[4-chloro-3-(trifluoromethyl)phenoxy]-2,5-dimethylphenyl]-N-ethyl-N-methylmethanimidamide, 5-fluoro-2-[(4-fluorophenyl)methoxy]-4-pyrimidinamine and 4-fluorophenyl N-[1-[[[1-(4-cyanophenyl)ethyl]sulfonyl]methyl]propyl]carbamate.

Additional "Fungicides other than fungicides of classes (b1) through (b54)" whose mode of action may be unknown, or may not yet be classified include a fungicidal compound selected from components (b54.7) through (b54.12), as shown below.

Component (54.7) relates to (1S)-2,2-bis(4-fluorophenyl)-1-methylethyl N-[[3-(acetyloxy)-4-methoxy-2-pyridinyl]carbonyl]-L-le (provisional common name florylpicoxamid, Registry Number 1961312-55-9) which is believed to be a Quinone inside inhibitor (QiI) fungicide (FRAC code 21) inhibiting the Complex III mitochondrial respiration in fungi.

Component (54.8) relates to 1-[2-[[[1-(4-chlorophenyl)-1H-pyrazol-3-yl]oxy]methyl]-3-methylphenyl]-1,4-dihydro-4-methyl-5H-tetrazol-5-one (provisional common name metyltetraprole, Registry Number 1472649-01-6), which is believed to be a quinone outside inhibitor (QoI) fungicide (FRAC code 45) inhibiting the Complex III mitochondrial respiration in fungi, and is effective against QoI resistant strains.

Component (54.9) relates to 3-chloro-4-(2,6-difluorophenyl)-6-methyl-5-phenylpyridazine (provisional common name pyridachlometyl, Registry Number 1358061-55-8), which is believed to be promoter tubulin polymerization, resulting antifungal activity against fungal species belonging to the phyla Ascomycota and Basidiomycota.

Component (54.10) relates to (4-phenoxyphenyl)methyl 2-amino-6-methyl-pyridine-3-carboxylate (provisional common name aminopyrifen, Registry Number 1531626-08-0) which is believed to inhibit GWT-1 protein in glycosylphosphatidylinositol-anchor biosynthesis in *Neurospora crassa*.

Component (b54.11) relates a compound of Formula b54.11 b54.11

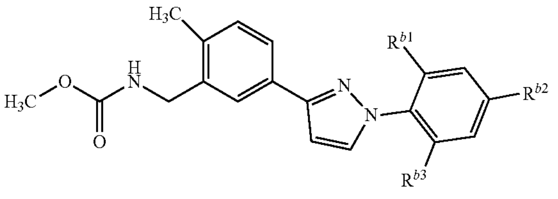

wherein $R^{b1}$ and $R^{b3}$ are each independently halogen; and $R^{b2}$ is H, halogen, $C_1$-$C_3$ alkyl, $C_1$-$C_3$ haloalkyl or $C_3$-$C_6$ cycloalkyl.

Examples of compounds of Formula b54.11 include (b54.11a) methyl N-[[5-[1-(2,6-difluoro-4-formylphenyl)-1H-pyrazol-3-yl]-2-methylphenyl]methyl]carbamate, (b54.11b) methyl N-[[5-[1-(4-cyclopropyl-2,6-dichlorophenyl)-1H-pyrazol-3-yl]-2-methylphenyl]methyl]carbamate, (b54.11c) methyl N-[[5-[1-(4-chloro-2,6-difluorophenyl)-1H-pyrazol-3-yl]-2-methylphenyl]-methyl]carbamate, (b54.11d) methyl N-[[5-[1-(4-cyclopropyl-2,6-difluorophenyl)-1H-pyrazol-3-yl]-2-methylphenyl]methyl]carbamate, (b54.11e) methyl N-[[5-[1-[2,6-difluoro-4-(1-methylethyl)phenyl]-1H-pyrazol-3-yl]-2-methylphenyl]methyl]carbamate and (b54.11f) methyl N-[[5-[1-[2,6-difluoro-4-(trifluoromethyl)phenyl]-1H-pyrazol-3-yl]-2-methylphenyl]methyl]carbamate. Compounds of Formula b54.11, their use as fungicides and methods of preparation are generally known; see, for example, PCT Patent Publications WO 2008/124092, WO 2014/066120 and WO 2020/097012.

Component (b54.12) relates to a compound of Formula b54.12

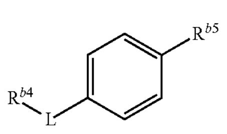

b54.12 wherein $R^{b4}$ is

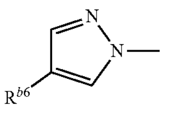

or

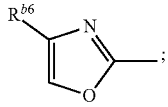

;

$R^{b6}$ is $C_2$-$C_4$ alkoxycarbonyl or $C_2$-$C_4$ haloalkylaminocarbonyl;

L is $CH_2$ or $CH_2O$, wherein the atom to the right is connected to the phenyl ring in Formula b54.12;

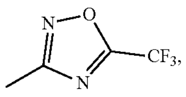

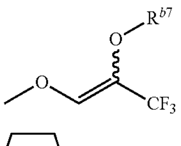

or

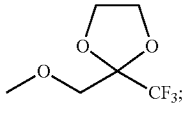

and $R^{b7}$ is $C_1$-$C_3$ alkyl, wherein the wavy bond indicates the adjacent double bond is either (Z)- or (E)-configuration, or a mixture thereof.

Examples of compounds of Formula b54.12 include (b54.12a) N-(2,2,2-trifluoroethyl)-2-[[4-[5-(trifluoromethyl)-1,2,4-oxadiazol-3-yl]phenyl]methyl]-4-oxazolecarboxamide, (b54.12b) ethyl 1-[[4-[5-(trifluoromethyl)-1,2,4-oxadiazol-3-yl]phenoxy]methyl]-1H-pyrazole-4-carboxylate, (b54.12c) ethyl 1-[[4-[[(1Z)-2-ethoxy-3,3,3-trifluoro-1-propen-1-yl]oxy]phenyl]methyl]-1H-pyrazole-4-carboxylate and (b54.12d) ethyl 1-[[4-[[2-(trifluoromethyl)-1,3-dioxolan-2-yl]methoxy]phenyl]methyl]-1H-pyrazole-4-carboxylate. Compounds of Formula b54.12, their use as fungicides and methods of preparation are generally known; see, for example, PCT Patent Publications WO 2008/187553 and WO 2020/056090.

Therefore of note is a mixture (i.e. composition) comprising a compound of Formula 1 and at least one fungicidal compound selected from the group consisting of the afore-described classes (b1) through (b54), including (b54.7) through (b54.12). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (b1) through (b54). Also of particular note is a composition comprising said mixture (in fungicidally effective amount) and further comprising at least one additional surfactant selected from the group consisting of surfactants, solid diluents and liquid diluents.

Examples of component (b) fungicides include acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, captafol, captan, carbendazim, carboxin, carpropamid, chloroinconazide, chloroneb, chlorothalonil, chlozolinate, clotrimazole, copper hydroxide, copper oxychloride, copper sulfate, coumoxystrobin, cyazofamid, cyclobutrifluram, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, dipymetitrone, econazole, edifenphos, enoxastrobin (also known as enestroburin), epoxiconazole, etaconazole, ethaboxam, ethirimol, etridiazole, famoxadone, fenamidone, fenarimol, fenaminstrobin, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, flometoquin, florylpicoxamid, fluazinam, fludioxonil, flufenoxadiazam, flufenoxystrobin, fluindapyr, flumetylsulforim, flumorph, fluopicolide, fluopimomide, fluopyram, flouroimide, fluoxastrobin, fluoxytioconazole, fluquinconazole, flusilazole, flusulfamide, flutianil, flutolanil, flutriafol, fluxapyroxad, folpet, fthalide, fuberidazole, furalaxyl, furametpyr, guazatine, hexaconazole, hymexazole, imazalil, imibenconazole, iminoctadine albesilate, iminoctadine triacetate, iodocarb, ipconazole, ipfentrifluconazole, iprobenfos, iprodione, iprovalicarb, isoconazole, isofetamid, isoprothiolane, isoflucypram, isopyrazam, isotianil, kasugamycin, kresoxim-methyl, mancozeb, mandepropamid, mandestrobin, maneb, mepanipyrim, mepronil, meptyldinocap, metalaxyl (including metalaxyl-M/mefenoxam), mefentrifluconazole, metarylpicoxamid, metconazole, methasulfocarb, metiram, metominostrobin, metrafenone, miconazole, myclobutanil, naftifine, neo-asozin, nuarimol, octhilinone, ofurace, orysastrobin, oxadixyl, oxathiapiprolin, oxolinic acid, oxpoconazole, oxycarboxin, oxytetracycline, pefurazoate, penconazole, pencycuron, penflufen, penthiopyrad, phosphorous acid (including salts thereof, e.g., fosetyl-aluminum), picarbutrazox, picoxystrobin, piperalin, polyoxin, probenazole, prochloraz, procymidone, propamacarb, propiconazole, propineb, proquinazid, prothiocarb, prothioconazole, pyraclostrobin, pyrametostrobin, pyraoxystrobin, pyrazophos, pyribencarb, pyributicarb, pyrifenox, pyrimethanil, pyriofenone, pyrisoxazole, pyroquilon, pyrrolnitrin, quinconazole, quinofumelin (Registry Number 861647-84-9) quinomethionate, quinoxyfen, quintozene, sedaxane, silthiofam, simeconazole, spiroxamine, streptomycin, sulfur, tebuconazole, tebufloquin, teclofthalam, tecnazene, terbinafine, tetraconazole, thiabendazole, thifluzamide, thiophanate, thiophanate-methyl, thiram, tiadinil, tolclofos-methyl, tolnifanide, tolprocarb, tolyfluanid, triadimefon, triadimenol, triarimol, triticonazole, triazoxide, tribasic copper sulfate, tricyclazole, triclopyricarb, tridemorph, trifloxystrobin, triflumizole, triforine, trimorphamide, uniconazole, uniconazole-P, validamycin, valifenalate (also known as valiphenal), vinclozolin, zineb, ziram, zoxamide, N-[2-(1S,2R)-[1,1'-bicyclopropyl]-2-ylphenyl]-3-(difluoromethyl)-1-methyl-1H-pyrazole-4-carboxamide, α-(1-chlorocyclopropyl)-α-[2-(2,2-dichlorocyclopropyl)ethyl]-1H-1,2,4-triazole-1-ethanol, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, rel-1-[[(2R,3S)-3-(2-chlorophenyl)-2-(2,4-difluorophenyl)-2-oxiranyl]-methyl]-5-(2-propen-1-ylthio)-1H-1,2,4-triazole, N-[2-[4-[[3-(4-chlorophenyl)-2-propyn-1-yl]-oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]-butanamide, N'-[4-[4-chloro-3-(trifluoromethyl)phenoxy]-2,5-dimethylphenyl]-N-ethyl-N-methylmethanimidamide, N-[[(cyclopropylmethoxy)amino][6-(difluoromethoxy)-2,3-difluorophenyl]methylene]benzeneacetamide, N-[2-(2,4-dichlorophenyl)-2-methoxy-1-methylethyl]-3-(difluoromethyl)-1-methyl-1H-pyrazole-4-carboxamide, N-(3',4'-difluoro[1,1'-biphenyl]-2-yl)-3-(trifluoromethyl)-2-pyrazinecarboxamide, 3-(difluoromethyl)-N-(2,3-dihydro-1,1,3-trimethyl-1H-inden-4-yl)-1-methyl-1H-pyrazole-4-carboxamide, 5,8-difluoro-N-[2-[3-methoxy-4-[[4-(trifluoromethyl)-2-pyridinyl]oxy]phenyl]ethyl]-4-quinazolinamine, 1-[4-[4-[5R-[(2,6-difluorophenoxy)methyl]-4,5-dihydro-3-isoxazolyl]-2-thiazolyl]-1-piperdinyl]-2-[5-methyl-3-(trifluoromethyl)-1H-pyrazol-1-yl]ethanone, 4-fluorophenyl N-[1-[[[1-(4-cyanophenyl)ethyl]-sulfonyl]methyl]propyl]carbamate, 5-fluoro-2-[(4-fluorophenyl)methoxy]-4-pyrimidinamine, α-(methoxyimino)-N-methyl-2-[[[1-[3-(trifluoromethyl)phenyl]ethoxy]imino]methyl]benzeneacetamide, [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropan-oate, methyl 2-[2-chloro-4-(4-chlorophenoxy)phenyl]-2-hydroxy-3-(1H-1,2,4-triazol-1-yl) propanoate, methyl 3-[(4-chlorophenyl)methyl]-2-hydroxy-1-methyl-2-(1H-1,2,4-triazol-1-ylmethyl) cyclopentanecarboxylate, and 6-(4-chlorophenoxy)-α-methyl-α-(1H-1,2,4-triazol-1-yl-methyl)-2-(trifluoromethyl)-3-pyridinemethanol. Therefore of note is a fungicidal composition comprising as component (a) a compound of Formula 1 (or an N-oxide or salt thereof) and as component (b) at least one fungicide selected from the preceding list.

Of particular note are combinations of compounds of Formula 1 (or an N-oxide or salt thereof) (i.e. Component (a) in compositions) with aminopyrifen (Registry Number 1531626-08-0), azoxystrobin, benzovindiflupyr, bixafen, captan, carpropamid, chlorothalonil, copper hydroxide, copper oxychloride, copper sulfate, cymoxanil, cyproconazole, cyprodinil, dichlobentiazox (Registry Number 957144-77-3), diethofencarb, difenoconazole, dimethomorph, dipymetitrone, epoxiconazole, ethaboxam, fenarimol, fenhexamid, fluazinam, fludioxonil, fluindapyr, fluopyram, flusilazole, flutianil, flutriafol, fluxapyroxad, folpet, ipflufenoquin (Registry Number 1314008-27-9), iprodione, isofetamid, isoflucypram, isopyrazam, kresoxim-methyl, mancozeb, mandestrobin, meptyldinocap, metalaxyl (including metalaxyl-M/mefenoxam), mefentrifluconazole, metarylpicoxamid, metconazole, metrafenone, metyltetraprole (Registry Number 1472649-01-6), myclobutanil, oxathiapiprolin, penflufen, penthiopyrad, phosphorous acid (including salts thereof, e.g., fosetyl-aluminum), picoxystrobin, propiconazole, proquinazid, prothioconazole, pyridachlometyl (Registry Number 1358061-55-8), pyraclostrobin, pyrapropoyne (Registry Number 1803108-03-3), pyrimethanil, sedaxane spiroxamine, sulfur, tebuconazole, thiophanate-methyl, trifloxystrobin, zoxamide, α-(1-chlorocyclopropyl)-α-[2-(2,2-dichlorocyclopropyl)ethyl]-1H-1,2,4-triazole-1-ethanol, N-[2-(2,4-dichlorophenyl)-2-methoxy-1-methylethyl]-3-(difluoromethyl)-1-methyl-1H-pyrazole-4-carboxamide, 3-(difluoromethyl)-N-(2,3-dihydro-1,1,3-trimethyl-1H-inden-4-yl)-1-methyl-1H-pyrazole-4-carboxamide, 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 1,1-di-methylethyl N-[6-[[[[(1-methyl-1H-tetrazol-5-yl)phenylmethylene]amino]oxy]methyl]-2-pyridinyl]carbamate, 5-fluoro-2-[(4-fluorophenyl)methoxy]-4-pyrimidinamine, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, and rel-1-[[(2R,3S)-3-(2-chlorophenyl)-2-(2,4-difluorophenyl)-2-oxiranyl]methyl]-5-(2-propen-1-ylthio)-1H-1,2,4-triazole (i.e. as Component (b) in compostions).

Generally preferred for better control of plant diseases caused by fungal plant pathogens (e.g., lower use rate or broader spectrum of plant pathogens controlled) or resistance management are mixtures of a compound of Formula 1, an N-oxide, or salt thereof, with a fungicidal compound selected from the group: amisulbrom, azoxystrobin, boscalid, carbendazim, carboxin, cymoxanil, cyproconazole, difenoconazole, dimethomorph, dimoxystrobin, fenpropimorph, florylpicoxamid, fluazinam, fludioxonil, flufenoxystrobin, fluindapyr, fluquinconazole, fluopicolide, fluoxastrobin, flutriafol, fluxapyroxad, ipconazole, ipfentrifluconazole, iprodione, kresoxim-methyl, metalaxyl, mefenoxam, mefentrifluconazole, metconazole, metominostrobin, myclobutanil, paclobutrazole, penflufen, picoxystrobin, prothioconazole, pyraclostrobin, pyrametostrobin, pyraoxystrobin, pyriofenone, sedaxane, silthiofam, tebuconazole, thiabendazole, thiophanate-methyl, thiram, trifloxystrobin and triticonazole.

Examples of other biologically active compounds or agents with which compounds of this invention can be formulated are: invertebrate pest control compounds or agents such as abamectin, acephate, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl]methyl cyclopropanecarboxylate), amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1H-pyrazole-5-carboxamide), cycloxaprid ((5S, 8R)-1-[(6-chloro-3-pyridinyl)methyl]-2,3,5,6,7,8-hexahydro-9-nitro-5,8-epoxy-1H-imidazo[1,2-a]azepine), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, flufenoxystrobin (methyl (αE)-2-[[2-chloro-4-(trifluoromethyl)phenoxy]methyl]-α-(methoxymethylene)benzeneacetate), fluensulfone (5-chloro-2-[(3,4,4-trifluoro-3-buten-1-yl)sulfonyl]thiazole), flupiprole (1-[2,6-dichloro-4-(trifluoromethyl)phenyl]-5-[(2-methyl-2-propen-1-yl)amino]-4-[(trifluoro-methyl) sulfinyl]-1H-pyrazole-3-carbonitrile), flupyradifurone (4-[[(6-chloro-3-pyridinyl)-methyl](2,2-difluoroethyl)amino]-2(5H)-furanone), tau-fluvalinate, flufenerim (UR-50701), flufenoxuron, fonophos, halofenozide, heptafluthrin ([2,3,5,6-tetrafluoro-4-(methoxymethyl)-phenyl]methyl 2,2-dimethyl-3-1[(1Z)-3,3,3-trifluoro-1-propen-1-yl]cyclopropanecarboxylate), hexaflumuron, hydramethylnon, imidacloprid, indoxacarb, isofenphos, lufenuron, malathion, meperfluthrin ([2,3,5,6-tetrafluoro-4-(methoxymethyl)phenyl]methyl (1R,3S)-3-(2,2-dichloro-ethenyl)-2,2-dimethyl-cyclopropanecarboxylate), metaflumizone, metaldehyde, methamidophos, methidathion, methomyl, methoprene, methoxychlor, methoxyfenozide, metofluthrin, milbemycin oxime, momfluorothrin ([2,3,5,6-tetrafluoro-4-(methoxymethyl)phenyl]methyl-3-(2-cyano-1-propen-1-yl)-2,2-dimethylcyclopropanecarboxylate), monocrotophos, nicotine, nitenpyram, nithiazine, novaluron, noviflumuron (XDE-007), oxamyl, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxy-methylene) benzeneacetate), pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai, Bacillus thuringiensis* subsp. kurstaki, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

One embodiment of biological agents for mixing with compounds of this disclosure include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Indiana, USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and *granulosis* virus (GV) such as *Cydia pomonella granulosis* virus (CpGV).

General references for these agricultural protectants (i.e. insecticides, fungicides, nematocides, acaricides, herbicides and biological agents) include *The Pesticide Manual,* 13th Edition, C. D. S. Tomlin, Ed., British Crop Protection Council, Farnham, Surrey, U. K., 2003 and *The BioPesticide Manual,* 2nd Edition, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:3000 to about 3000:1, and more typically between about 1:500 and about 500:1. Of note are compositions where in the weight ratio of component (a) to component (b) is from about 125:1 to about 1:125. With many fungicidal compounds of component (b), these compositions are particularly effective for controlling plant diseases caused by fungal plant pathogens. Of particular note are compositions wherein the weight ratio of component (a) to component (b) is from about 25:1 to about 1:25, or from about 5:1 to about 1:5. One skilled in the art can easily determine through simple experimentation the weight ratios and application rates of fungicidal compounds necessary for the desired spectrum of fungicidal protection and control. It will be evident that including additional fungicidal compounds in component (b) may expand the spectrum of plant diseases controlled beyond the spectrum controlled by component (a) alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Also in certain instances, combinations of a compound of the invention with other biologically active compounds or agents can result in a less-than-additive (i.e. safening) effect on organisms beneficial to the agronomic environment. For example, a compound of the invention may safen a herbicide on crop plants or protect a beneficial insect species (e.g., insect predators, pollinators such as bees) from an insecticide.

Fungicides of note for formulation with compounds of Formula 1 to provide mixtures useful in seed treatment include but are not limited to amisulbrom, azoxystrobin, boscalid, carbendazim, carboxin, cymoxanil, cyproconazole, difenoconazole, dimethomorph, florylpicoxamid, fluazinam, fludioxonil, flufenoxystrobin, fluquinconazole, fluopicolide, fluoxastrobin, flutriafol, fluxapyroxad, ipconazole, iprodione, metalaxyl, mefenoxam, mefentrifluconazole, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Invertebrate pest control compounds or agents with which compounds of Formula 1 can be formulated to provide mixtures useful in seed treatment include but are not limited to abamectin, acetamiprid, acrinathrin, afidopyropen, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyclaniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, fluensulfone, flufenoxuron, flufiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, momfluorothrin, nitenpyram, nithiazine, novaluron, oxamyl, pyflubumide, pymetrozine, pyrethrin, pyridaben, pyriminostrobin, pyridalyl, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumuron, *Bacillus thuringiensis* delta-endotoxins, strains of *Bacillus thuringiensis* and strains of Nucleo polyhydrosis viruses.

Compositions comprising compounds of Formula 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM I-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium* verrucaria, *Paecilomyces lilacinus* and Purpureocillium lilacinum.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by *rhizobia* bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

Remarkably, 3-pyridinecarbonitrile compounds of Formula 1 (i.e. Formula 1 wherein J is J-8 and $R^4$ is cyano) have been discovered to have significantly improved fungicidal properties compared to corresponding compounds wherein $R^4$ is other than cyano. Illustrative of 3-pyridinecarbonitrile compounds of Formula 1 wherein J is J-8 and $R^4$ is cyano are Compound numbers 68, 69 and 70.

The following TESTS demonstrate the control efficacy of compounds of this invention on specific pathogens. The pathogen control protection afforded by the compounds is not limited, however, to these species. See Index Tables A-G below for compound descriptions. The abbreviation "Cmpd." stands for "Compound", and the abbreviation "Ex." Stands for "Example" and is followed by a number indicating in which example the compound is prepared. The numerical value reported in the column "MS" is the molecular weight of the highest isotopic abundance positively charged parent ion (M+1) formed by addition of H+ (molecular weight of 1) to the molecule having the highest isotopic abundance, or the highest isotopic abundance negatively charged ion (M-1) formed by loss of H+ (molecular weight of 1). The presence of molecular ions containing one or more higher atomic weight isotopes of lower abundance (e.g., $^{37}Cl$, $^{81}Br$) is not reported. The reported MS peaks were observed by mass spectrometry using electrospray ionization (ESI) or atmospheric pressure chemical ionization (APCI).

INDEX TABLE A

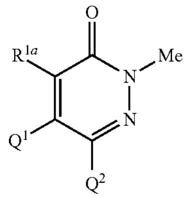

| Cmpd. No. | $R^{1a}$ | $Q^1$ | Q2 | m.p. (° C.) | MS (M + 1) |
|---|---|---|---|---|---|
| 1 | H | 2,6-di-F—Ph | 3-thienyl | | 305 |
| 2 | H | 2,6-di-F—Ph | 3-pyridinyl | | 300 |
| 3 | H | 2,6-di-F—Ph | 3-furanyl | | 289 |
| 4 (Ex. 2) | Cl | 2-C1, 4-F—Ph | 4-Me-3-pyridinyl | | 364 |
| 5 | Me | 2-C1, 4-F—Ph | 3-thienyl | 113-115 | 335 |
| 6 | Me | 2-C1, 4-F—Ph | 2-Br-3-thienyl | 135-136 | 415 |
| 7 (Ex. 1) | Me | 2-C1, 4-F—Ph | 2-C1-3-thienyl | | 369 |
| 8 | Me | 2-C1, 4-F—Ph | 2-Me-3-thienyl | 92-95 | 349 |
| 9 | Me | 2-C1, 4-F—Ph | 2-thienyl | 126-128 | 335 |
| 10 | Me | 2-Cl, 4-F—Ph | 5-Cl-2-thienyl | 120-122 | 369 |
| 11 | Me | 2-Cl, 4-F—Ph | 4-Me-1H-pyrazol-1-yl | 68-70 | 333 |
| 12 | Me | 2-Cl—Ph | 4-Me-1H-pyrazol-1-yl | | 315 |
| 13 | Me | 2-Cl, 4-F—Ph | 2,5-di-Br-3-thienyl | 125-127 | 493 |
| 14 | Me | 2-Cl, 4-F—Ph | 4-Me-3-thienyl | 113-115 | 349 |
| 15 | Me | 2-Cl, 4-F—Ph | 4-Me, 5-Br-3-thienyl | | 429 |
| 16 | Me | 2-Cl, 4-F—Ph | 3,5-di-Br-2-thienyl | 130-132 | 493 |
| 17 | Me | 2-Cl, 4-F—Ph | 5-Br-2-thienyl | 62-65 | 415 |
| 18 | Me | 2-Me-3-thienyl | 2-C1, 5-MeO—Ph | | 361 |
| 19 | H | 2-Me-3-thienyl | 2-C1, 5-MeO—Ph | | 361 |
| 20 | Me | 2-Cl, 4-F—Ph | 1-Me-1H-pyrazol-3-yl | | 333 |
| 21 (Ex. 3) | Me | 4-Me-3-pyridinyl | 2-C1, 5-MeO—Ph | 155-158 | 356 |
| 22 | Me | 2-Cl, 4-F—Ph | 1-Me-4-Cl-1H-pyrazol-3-yl | | 367 |

INDEX TABLE B

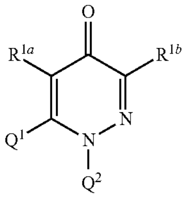

| Cmpd. No. | $R^{1a}$ | $R^{1b}$ | $Q^1$ | $Q^2$ | m.p (° C.) | MS (M + 1) |
|---|---|---|---|---|---|---|
| 23 (Ex. 6) | Me | $CH_2OH$ | 2,4-di-F—Ph | 3,5-di-MeO—Ph | 157-160 | |
| 24 | Me | C(═O)OMe | 2,4-di-F—Ph | 3,5-di-MeO—Ph | 157-160 | |
| 25 | Me | $CH_2Cl$ | 2,4-di-F—Ph | 3,5-di-MeO—Ph | 120-123 | |
| 26 | Me | $CH_2F$ | 2,4-di-F—Ph | 3,5-di-MeO—Ph | 125-129 | |
| 27 (Ex. 4) | Me | C(═O)OH | 2,4-di-F—Ph | 3,5-di-MeO—Ph | 195-198 | |
| 28 (Ex. 5) | Me | C(═O)OEt | 2,4-di-F—Ph | 3,5-di-MeO—Ph | 146-149 | |
| 29 | Me | Me | 2,4-di-F—Ph | 3,5-di-MeO—Ph | 124-127 | |
| 30 (Ex. 7) | Me | $CH_2OH$ | 2,4-di-F—Ph | 2-Cl, 3,5-di-MeO—Ph | 166-169 | |
| 31 | Me | $CH_2C{\equiv}N$ | 2,4-di-F—Ph | 3,5-di-MeO—Ph | | 398 |
| 32 (Ex. 7) | Me | $CH_2OH$ | 2,4-di-F—Ph | 4-Cl, 3,5-di-MeO—Ph | 255-258 | |
| 33 (Ex. 8) | Me | Me | 2,4-di-F—Ph | 2-Cl, 3,5-di-MeO—Ph | 135-138 | |
| 73 | Cl | Cl | 2,4-di-F—Ph | 2-Cl, 5-MeO—Ph | 163-166 | |
| 74 | Br | Cl | 2,4-di-F—Ph | 2-Cl, 5-MeO—Ph | | 461 |
| 75 | Br | Br | 2,4-di-F—Ph | 2-Cl, 5-MeO—Ph | 212-215 | |
| 76 | H | MeO | 2,4-di-F—Ph | 2-Cl, 5-MeO—Ph | 193-196 | |
| 77 | Cl | C(═O)OH | 4-F—Ph | 2-Cl, 3-MeO—Ph | | |
| 78 | Cl | Br | 2,4-di-F—Ph | 2-Cl, 5-MeO—Ph | 193-196 | |
| 79 | Cl | $CH_2OH$ | 4-F—Ph | 2-Cl, 3-MeO—Ph | | |
| 80 | Cl | Me | 4-F—Ph | 2-Cl, 3-MeO—Ph | | |
| 81 | EtOC(═O) | EtOC(═O) | 2,4-di-F—Ph | 2-Cl, 5-MeO—Ph | | 493 |
| 82 | EtOC(═O) | EtOC(═O) | 4-F—Ph | 2-Cl, 5-MeO—Ph | | 475 |
| 83 | Me | N≡C | 2-Cl, 4-F—Ph | 2-Cl, 3,5-di-MeO—Ph | 222-225 | |
| 84 | Me | Me | 2-Cl, 4-F—Ph | 2-Cl, 3,5-di-MeO—Ph | 147-150 | |
| 85 | Me | $CH_2F$ | 2-Cl, 4-F—Ph | 2-Cl, 3,5-di-MeO—Ph | 153-156 | |
| 86 | Me | t-BuOC(═O)NH | 2-Cl, 4-F—Ph | 2-Cl, 3,5-di-MeO—Ph | 239-242 | |

-continued

INDEX TABLE B

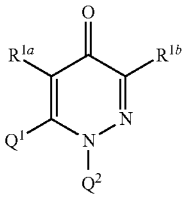

| Cmpd. No. | $R^{1a}$ | $R^{1b}$ | $Q^1$ | $Q^2$ | m.p (° C.) | MS (M + 1) |
|---|---|---|---|---|---|---|
| 87 | Me | $NH_2$ | 2-Cl, 4-F—Ph | 2-Cl, 3,5-di-MeO—Ph | 209-212 | |
| 88 | EtOC(═O) | EtOC(═O) | 2,4-di-F—Ph | 3,5-di-MeO—Ph | | 489 |
| 89 | EtOC(═O) | C(═O)OH | 2,4-di-F—Ph | 3,5-di-MeO—Ph | | |
| 90 | Me | $CH_2F$ | 2-Cl, 4-F—Ph | 3,5-di-MeO—Ph | 135-138 | |
| 91 | Me | $CH_2OH$ | 2-Cl, 4-F—Ph | 3,5-di-MeO—Ph | 321-324 | |
| 92 | Me | Cl | 2-Cl, 4-F—Ph | 2-Cl, 3,5-di-MeO—Ph | 192-195 | |
| 93 | Me | C(═O)OH | 2-Cl, 4-F—Ph | 3,5-di-MeO—Ph | 185-188 | |
| 94 | Me | Br | 2-C1, 4-F—Ph | 2-C1, 3,5-di-MeO—Ph | 191-194 | |
| 95 | Me | C(═O)OH | 2-Cl, 4-F—Ph | 2-Cl, 3,5-di-MeO—Ph | 240-243 | |
| 96 | Me | I | 2-Cl, 4-F—Ph | 2-C1, 3,5-di-MeO—Ph | 228-231 | |
| 97 | Me | Me | 2-Cl, 4-F—Ph | 3,5-di-MeO—Ph | 148-151 | |
| 98 | Me | EtOC(═O) | 2-Cl, 4-F—Ph | 2-Cl, 3,5-di-MeO—Ph | 179-182 | |
| 99 | Cl | $CH_2OH$ | 2-Cl, 4-F—Ph | 2-Cl, 3,5-di-MeO—Ph | 177-178 | |
| 100 | H | H | 2-Cl, 4-F—Ph | 2-Cl, 5-MeO—Ph | 174-177 | |
| 101 | Cl | Br | 2-Cl, 4-F—Ph | 2-Cl, 5-MeO—Ph | 205-208 | |
| 102 | Br | Br | 2-Cl, 4-F—Ph | 2-Cl, 5-MeO—Ph | 215-218 | |
| 103 | Cl | Cl | 2-Cl, 4-F—Ph | 2-Cl, 5-MeO—Ph | 159-161 | |
| 104 (Ex. 29) | Cl | C(═O)OH | 4-F—Ph | 2-Cl, 5-MeO—Ph | * | |
| 105 (Ex. 31) | Cl | Me | 4-F—Ph | 2-Cl, 5-MeO—Ph | 207-210 | 380 |
| 106 | H | C(═O)OH | 2,4-di-F—Ph | 2-Cl, 5-MeO—Ph | 190-193 | |
| 107 | H | EtOC(═O) | 2,4-di-F—Ph | 2-Cl, 5-MeO—Ph | 130-133 | |
| 108 | H | $CH_2OH$ | 2,4-di-F—Ph | 2-Cl, 5-MeO—Ph | 164-168 | |
| 109 | H | Me | 2,4-di-F—Ph | 2-Cl, 5-MeO—Ph | 95-98 | |
| 110 | Cl | Me | 2,4-di-F—Ph | 2-Cl, 5-MeO—Ph | 161-164 | |
| 111 | Br | Me | 2,4-di-F—Ph | 2-Cl, 5-MeO—Ph | 176-178 | |
| 112 | H | t-BuOC(═O)NH | 2,4-di-F—Ph | 2-Cl, 5-MeO—Ph | 180-182 | |
| 113 | H | $NH_2$ | 2,4-di-F—Ph | 2-Cl, 5-MeO—Ph | 183-186 | |
| 114 | H | Cl | 2,4-di-F—Ph | 2-Cl, 5-MeO—Ph | 168-170 | |
| 115 | H | Br | 2,4-di-F—Ph | 2-Cl, 5-MeO—Ph | 171-174 | |
| 116 | H | H | 2,4-di-F—Ph | 2-Cl, 5-MeO—Ph | 192-195 | |
| 117 | H | C(═O)OH | 2-C1, 4-F—Ph | 2-Cl, 5-MeO—Ph | 217-220 | |
| 118 | H | MeO | 2-C1, 4-F—Ph | 2-Cl, 5-MeO—Ph | 157-160 | |
| 119 | H | EtOC(═O) | 2-C1, 4-F—Ph | 2-C1, 5-MeO—Ph | 135-137 | |
| 120 | H | $CH_2OH$ | 2-Cl, 4-F—Ph | 2-Cl, 5-MeO—Ph | 171-174 | |
| 121 | H | Me | 2-C1, 4-F—Ph | 2-Cl, 5-MeO—Ph | 156-159 | |
| 122 | Cl | MeOC(═O) | 2-F—Ph | 2-Cl, 5-MeO—Ph | | |
| 123 | Cl | Me | 2-C1, 4-F—Ph | 2-Cl, 5-MeO—Ph | 231-233 | |
| 124 | Br | Me | 2-C1, 4-F—Ph | 2-Cl, 5-MeO—Ph | 155-158 | |
| 125 | EtOC(═O) | EtOC(═O) | 4-F—Ph | 3,5-di-MeO—Ph | | 471 |
| 126 | EtOC(═O) | EtOC(═O) | 4-F—Ph | 2-Cl, 3,5-di-MeO—Ph | | 505 |
| 127 | EtOC(═O) | EtOC(═O) | 2,4-di-F—Ph | 2-Cl, 3,5-di-MeO—Ph | | 523 |
| 128 (Ex. 30) | Cl | $CH_2OH$ | 4-F—Ph | 2-Cl, 5-MeO—Ph | * | |
| 129 | Cl | Me | 2-Cl, 4-MeO—Ph | 2-Cl, 5-MeO—Ph | 216-218 | |
| 130 | Br | Me | 2-Cl, 4-MeO—Ph | 2-Cl, 5-MeO—Ph | 213-216 | |
| 131 | H | t-BuOC(═O)NH | 2-Cl, 4-F—Ph | 2-Cl, 5-MeO—Ph | 190-193 | |
| 132 | H | $NH_2$ | 2-C1, 4-F—Ph | 2-Cl, 5-MeO—Ph | 207-210 | |
| 133 | H | Cl | 2-Cl, 4-F—Ph | 2-Cl, 5-MeO—Ph | 193-196 | |
| 134 | Br | Cl | 2-Cl, 4-F—Ph | 2-Cl, 5-MeO—Ph | 194-197 | |
| 135 | H | MeC(═O)NH | 2-Cl, 4-F—Ph | 2-Cl, 5-MeO—Ph | 203-206 | |
| 136 | H | Br | 2-Cl, 4-F—Ph | 2-Cl, 5-MeO—Ph | 178-181 | |

*See Index Table H for $^1H$ NMR data.

INDEX TABLE C

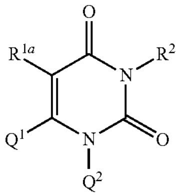

| Cmpd. No. | $R^{1a}$ | $R^2$ | $Q^1$ | $Q^2$ | m.p. (° C.) |
|---|---|---|---|---|---|
| 34 (Ex. 9) | H | Me | 2-Cl, 4-F—Ph | 3,5-di-MeO—Ph | 145-148 |
| 35 (Ex. 10) | Cl | Me | 2-Cl, 4-F—Ph | 2-Cl, 3,5-di-MeO—Ph | 213-216 |
| 36 (Ex. 10 and Ex. 11) | H | Me | 2-Cl, 4-F—Ph | 2-Cl, 3,5-di-MeO—Ph | 167-170 |
| 37 (Ex. 13) | Me | Me | 2-Cl, 4-F—Ph | 2-Cl, 3,5-di-MeO—Ph | 196-199 |
| 38 (Ex. 11) | Cl | Me | 2-Cl, 4-F—Ph | 3,5-di-MeO—Ph | |
| 39 (Ex. 12) | Me | Me | 2-Cl, 4-F—Ph | 3,5-di-MeO—Ph | |

INDEX TABLE D

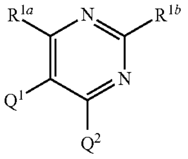

| Cmpd. No. | $R^{1a}$ | $R^{1b}$ | $Q^1$ | $Q^2$ | m.p. (°C.) | MS (M+1) |
|---|---|---|---|---|---|---|
| 40 | H | H | 2,4,6-tri-F—Ph | 3,5-di-MeO—Ph | | 347 |
| 41 | H | Me | 2,4,6-tri-F—Ph | 3,5-di-MeO—Ph | | 361 |
| 42 (Ex. 15) | Me | Me | 2-Cl, 4-F—Ph | 2-Cl, 3,5-di-MeO—Ph | | 407 |
| 43 | Me | H | 2-Cl, 4-F—Ph | 2-Cl, 4-F—Ph | | * |
| 44 (Ex. 14) | Me | Me | 2-Cl, 4-F—Ph | 3,5-di-MeO—Ph | | 373 |
| 45 (Ex. 18) | Me | Cl | 2-Cl, 4-F—Ph | 3,5-di-MeO—Ph | | 393 |
| 46 (Ex. 16) | Me | Cl | 2,6-di-F—Ph | 3,5-di-MeO—Ph | | 377 |
| 47 | Me | Cl | 2-Cl, 4-F—Ph | 3,5-di-MeO—Ph | | 393 |
| 48 (Ex. 17) | Me | Cl | 2,6-di-F—Ph | 2-Cl, 3,5-di-MeO—Ph | | 411 |
| 49 (Ex. 19) | Me | Cl | 2-Cl, 4-F—Ph | 2-Cl, 3,5-di-MeO—Ph | | 427 |
| 50 (Ex. 20) | Me | Me | 2-Cl, 4-F—Ph | 2-Cl, 5-MeO—Ph | | 377 |
| 51 | MeO | H | 2,4,6-tri-F—Ph | 3,5-di-MeO—Ph | | 377 |
| 52 | Cl | Me | 2-Cl, 4-F—Ph | 3,5-di-MeO—Ph | | 393 |
| 53 (Ex.22) | Me | Me | 2,4,6-tri-F—ph | 3,5-di-MeO—Ph | | 375 |
| 54 (Ex. 23) | Me | Me | 2,4,6-tri-F—Ph | 2-Cl, 3,5-di-MeO—Ph | | 409 |
| 55 | Me | Me | 2,6-di-F—Ph | 2-Cl, 3,5-di-MeO—Ph | | 391 |
| 56 | Et | Me | 2-Cl, 4-F—Ph | 2-Cl, 3,5-di-MeO—Ph | | 421 |
| 57 | Et | Me | 2,6-di-F—Ph | 2-Cl, 3,5-di-MeO—Ph | | 405 |
| 58 | MeO | Me | 2-Cl, 4-F—Ph | 3,5-di-MeO—Ph | | 390 |
| 59 | Me | Me | 2-Cl, 4-F—Ph | 2-Br, 3,5-di-MeO—Ph | | 451 |
| 65 (Ex. 21) | Cl | Me | 2,4,6-tri-F—Ph | 3,5-di-MeO—Ph | | 451 |
| 66 (Ex. 24) | Et | Me | 2,6-di-F—Ph | 3,5-di-MeO—Ph | | 371 |
| 147 | Me | Me | 2,4-di-F—Ph | 2-Cl, 3,5-di-MeO—Ph | 112-115 | |
| 148 | Me | Me | 2,4-di-F—Ph | 2-Br, 5-MeO—Ph | 132-135 | |
| 149 | Me | Me | 2,4-di-F—Ph | 2-Cl, 5-MeO—Ph | 99-101 | |
| 150 | Me | Me | 2,4-di-F—Ph | 2-Me, 5-MeO—Ph | 109-111 | |

*See Index Table H for $^1H$ NMR data.

INDEX TABLE E

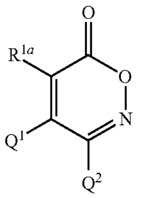

| Cmpd. No. | $R^{1a}$ | $Q^1$ | $Q^2$ | m.p. (° C.) |
|---|---|---|---|---|
| 60 | Me | 3,5-di-MeO—Ph | 2,4,6-tri-F—Ph | 140-143 |
| 61 | Me | 3,5-di-MeO—Ph | 2,4-di-F—Ph | 129-132 |
| 62 | Me | 2-Cl, 3,5-di-MeO—Ph | 2,4-di-F—Ph | 125-128 |
| 63 | Me | 2-Br, 3,5-di-MeO—Ph | 2,4-di-F—Ph | 136-139 |
| 64 (Ex. 25) | Me | 2-Cl, 4-F—Ph | 2-Cl, 3,5-di-MeO—Ph | 161-164 |

INDEX TABLE F

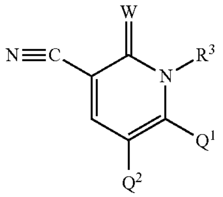

| Cmpd. No. | $R^3$ | $Q^1$ | $Q^2$ | m.p. (° C.) | MS (M + 1) |
|---|---|---|---|---|---|
| 67 (Ex. 27) | Me | 2,4,6-tri-F—Ph | 3,5-di-MeO—Ph | 180-183 | |
| 68 (Ex. 28) | Me | 2,4,6-tri-F—Ph | 2-Cl, 3,5-di-MeO—Ph | 159-162 | |
| 69 | Et | 2,4,6-tri-F—Ph | 3,5-di-MeO—Ph | 185-187 | |
| 70 | Et | 2,4,6-tri-F—Ph | 2-Cl, 3,5-di-MeO—Ph | 171-173 | |
| 71 (Ex. 28) | Me | 2,4,6-tri-F—Ph | 4-Cl, 3,5-di-MeO—Ph | 223-227 | |
| 72 | Et | 2,4,6-tri-F—Ph | 4-Cl, 3,5-di-MeO—Ph | 205-208 | |
| 153 | $NH_2$ | 2,4,6-tri-F—Ph | 3,5-di-MeO—Ph | | 402 |
| 154 | Me | 2-Cl, 4-F—Ph | 2-Cl, 5-MeO—Ph | 210-213 | |
| 155 | Et | 2-Cl, 4-F—Ph | 3,5-di-MeO—Ph | 232-235 | |
| 156 | Me | 2-Cl, 4-F—Ph | 2-Cl, 3,5-di-MeO—Ph | 209-211 | |
| 157 | Et | 2-Cl, 4-F—Ph | 2-Cl, 3,5-di-MeO—Ph | 100-103 | |
| 158 | Me | 2-Cl, 4-F—Ph | 3,5-di-MeO—Ph | 227-230 | |
| 159 | Et | 2-Cl, 4-F—Ph | 2-Cl, 5-MeO—Ph | 171-174 | |
| 160 | Me | 2-Cl, 4-F—Ph | 4-Cl, 3-MeO—Ph | 205-208 | |

INDEX TABLE G

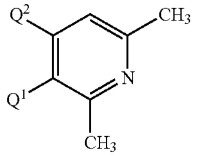

| Cmpd. No. | $Q^1$ | $Q^2$ | m.p. (° C.) | MS (M + 1) |
|---|---|---|---|---|
| 137 | 2-Cl, 4-F—Ph | 2-Cl, 3,5-di-MeO—Ph | 131-134 | |
| 138 (Ex. 26) | 2-Cl, 4-F—Ph | 2-Cl, 5-MeO—Ph | 106-108 | |
| 139 | 2,4-di-F—Ph | 2-Cl, 5-MeO—Ph | | 360 |
| 140 | 2-Cl, 4-F—Ph | 2,4-di-Br, 3,5-di-MeO—Ph | 152-155 | |
| 141 | 2,4-di-F—Ph | 2-Br, 3,5-di-MeO—Ph | 69-72 | |
| 142 | 2-Cl, 4-F—Ph | 2-Br, 3,5-di-MeO—Ph | 133-136 | |
| 143 | 2-Cl, 4-F—Ph | 2-Cl, 3-MeO—Ph | 125-127 | |
| 144 | 2,6-di-F—Ph | 2,4-di-Br, 3,5-di-MeO—Ph | 156-159 | |
| 145 | 2,4-di-F—Ph | 2-Cl, 3-MeO—Ph | 120-123 | |
| 146 | 2,4-di-F—Ph | 3,5-di-MeO—Ph | 116-119 | |

INDEX TABLE H

| Compound No. | $^1$H NMR Data ($CDCl_3$ solution)[a] |
|---|---|
| 43 | δ 9.18 (d, 1H), 7.67 (dd, 1 H), 7.57 (d, 1H), 7.24 (d, 1H) 7.17-7.12 (m, 2H), 2.61 (s, 3H). |
| 51 | δ 8.89 (s, 1H), 6.66 (dd, 2H), 6.52 (d, 2H), 6.43 (t, 1H) 4.01 (s, 3H), 3.68 (s, 6H). |
| 55 | δ 7.25-7.20 (m, 1H), 6.84 (br d, 2H), 6.46-6.30 (m, 2H), 3.79 (s, 3H) 3.70 (s, 3H), 2.83 (s, 3H), 2.39 (s, 3H). |
| 56 | δ 7.24-7.15 (m, 1H), 7.13-7.07 (m, 1H), 6.88 (m, 1H), 6.44-6.27 (m, 2H) 3.80 (s, 3H), 3.68 (s, 3H), 2.83 (s, 3H), 2.64-2.54 (m, 1H), 2.54-2.44 (m, 1H), 1.20 (t, 3H). |
| 57 | δ 7.25-7.20 (m, 1H), 6.93-6.72 (m, 2H), 6.44-6.32 (m, 2H), 3.79 (s, 3H) 3.70 (s, 3H), 2.84 (s, 3H), 2.62 (q, 2H), 1.21 (t, 3H). |
| 58 | δ 7.17 (dd, 1H), 6.98 (dd, 1H), 6.90 (m, 1H), 6.48 (d, 2H) 6.36 (t, 1, H), 3.96 (s, 3H), 3.68-3.61 (m, 6H), 2.73 (s, 3H). |
| 59 | δ 7.25-7.17 (m, 1H), 7.12 (dd, 1H), 6.88 (m, 2.60 1H), 6.38-6.31 (m, 2H) 3.81 (s, 3H), 3.67 (m, 3H), 2.82 (m, 3H), 2.32 (s, 3H). |
| 104 | δ 7.50-7.43 (m, 1H), 7.25-7.17 (m, 2H), 7.11-7.04 (m, 3H), 6.86-6.83 (m, 1H), 3.75 (s, 3H). |
| 105 | δ 7.31-7.43 (m, 1H), 7.14-7.25 (m, 2H), 7.00 (m, 2H), 6.80 (m, 1H) 6.74 (m, 1H), 3.73 (s, 3H), 2.47 (s, 3H). |
| 128 | δ 7.42-7.35 (m, 1H), 7.25-7.17 (m, 2H), 7.06-7.00 (m, 2H), 6.83 (m, 1H), 6.80-6.73 (m, 1H), 4.91-4.79 (m, 2H), 3.74 (s, 3H). |

[a]$^1$H NMR data are reported in ppm downfield from tetramethylsilane. Couplings are designated by (s)—singlet, (br s)—broad singlet, (d)—doublet, and (m)—multiplet.

BIOLOGICAL EXAMPLES OF THE INVENTION

General protocol for preparing test suspensions for Tests A-F: the test compounds were first dissolved in acetone in an amount equal to 3% of the final volume and then suspended at the desired concentration (in ppm) in acetone and purified water (50/50 mix by volume) containing 50 to 250 ppm of the surfactant PEG400 (polyhydric alcohol esters). The resulting test suspensions were then used in Tests A-F.

TEST A

The test solution was sprayed to the point of run-off on wheat seedlings. The following day the seedlings were inoculated with a spore suspension of *Zymoseptoria tritici* (the causal agent of wheat leaf blotch) and incubated in a saturated atmosphere at 24° C. for 48 h, and then moved to a growth chamber at 20° C. for 17 days, after which time disease ratings were made.

TEST B

The test solution was sprayed to the point of run-off on wheat seedlings. The following day the seedlings were inoculated with a spore suspension of *Puccinia recondita* f. sp. *Tritici* (the causal agent of wheat leaf rust) and incubated in a saturated atmosphere at 20° C. for 24 h, and then moved to a growth chamber at 20° C. for 7 days, after which time disease ratings were made.

TEST C

The test suspension was sprayed to the point of run-off on wheat seedlings. The following day the seedlings were inoculated with a spore dust of Blumeria *graminis* f. sp. *Tritici*, (also known as *Erysiphe graminis* f. sp. *Tritici*, the causal agent of wheat powdery mildew) and incubated in a growth chamber at 20° C. for 8 days, after which time visual disease ratings were made.

TEST D

The test solution was sprayed to the point of run-off on soybean seedlings. The following day the seedlings were inoculated with a spore suspension of *Phakopsora pachyrhizi* (the causal agent of Asian soybean rust) and incubated in a saturated atmosphere at 22° C. for 24 h and then moved to a growth chamber at 22° C. for 8 days, after which time visual disease ratings were made.

TEST E

The test suspension was sprayed to the point of run-off on tomato seedlings. The following day the seedlings were inoculated with a spore suspension of *Botrytis cinerea* (the causal agent of tomato *Botrytis*) and incubated in a saturated atmosphere at 20° C. for 48 h, and then moved to a growth chamber at 24° C. for 3 days, after which time visual disease ratings were made.

TEST F

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 3 days, after which time visual disease ratings were made. Results for Tests A-F are given in Table A below. A rating of 100 indicates 100% disease control and a rating of 0 indicates no disease control (relative to the controls). A dash (-) indicates the compound was not tested.

TABLE A

| Cmpd No. | Rate in ppm | Test A | Test B | Test C | Test D | Test E | Test F |
|---|---|---|---|---|---|---|---|
| 1 | 250 | 0 | 0 | 0 | 65 | 0 | 0 |
| 2 | 50 | 0 | 0 | 0 | 0 | 0 | 0 |
| 3 | 250 | 0 | 0 | 0 | 38 | 0 | 0 |
| 4 | 50 | 100 | 89 | 89 | 38 | 65 | 70 |
| 5 | 50 | 100 | 74 | 96 | 21 | 93 | 91 |
| 6 | 50 | 100 | 100 | 99 | 78 | 91 | 99 |
| 7 | 50 | 99 | 100 | 99 | 100 | 97 | 99 |
| 8 | 50 | 99 | 100 | 99 | 96 | 94 | 99 |
| 9 | 50 | 100 | 79 | 95 | 8 | 98 | 16 |
| 10 | 50 | 100 | 68 | 96 | 12 | 96 | 16 |
| 11 | 50 | 70 | 0 | 97 | 0 | 91 | 24 |
| 12 | 50 | 0 | 0 | 0 | 17 | 0 | 15 |
| 13 | 50 | 99 | 80 | 73 | 0 | 90 | 0 |
| 14 | 50 | 100 | 99 | 97 | 72 | 96 | 94 |
| 15 | 50 | 100 | 100 | 99 | 24 | 92 | 99 |
| 16 | 50 | 99 | 68 | 64 | 0 | 37 | 0 |
| 17 | 50 | 99 | 68 | 56 | 12 | 39 | 0 |
| 18 | 50 | 96 | 92 | 93 | 13 | 97 | 0 |
| 19 | 250 | 0 | — | 0 | 0 | 94 | 0 |
| 20 | 50 | 0 | 19 | 72 | 0 | 33 | 0 |
| 21 | 50 | 54 | 68 | 86 | 25 | 96 | 0 |
| 22 | 50 | 94 | 93 | 98 | 53 | 94 | 0 |
| 23 | 50 | 3 | 68 | 0 | 43 | 46 | 53 |
| 24 | 50 | 8 | 0 | 0 | 0 | 0 | 0 |
| 25 | 50 | 18 | 0 | 43 | 75 | 34 | 0 |
| 26 | 50 | 100 | 100 | 98 | 99 | 98 | 99 |
| 27 | — | — | — | — | — | — | — |
| 28 | 250 | 0 | 83 | 43 | 0 | 31 | 0 |
| 29 | 50 | 100 | 100 | 100 | 99 | 98 | 100 |
| 30 | 50 | 63 | 100 | 98 | 92 | 94 | 99 |
| 31 | 50 | 61 | 0 | 0 | 0 | 9 | 0 |
| 32 | 50 | 0 | 0 | 0 | 25 | 0 | 0 |
| 33 | 50 | 100 | 100 | 100 | 100 | 98 | 94 |
| 34 | 250 | 25 | 86 | 0 | 64 | 63 | 0 |
| 35 | 50 | 100 | 100 | 98 | 91 | 94 | 0 |
| 36 | 50 | 95 | 100 | 92 | 89 | 88 | 0 |
| 37 | 50 | 100 | 100 | 98 | 77 | 95 | 53 |
| 38 | 50 | 0 | 96 | 0 | 0 | 70 | 0 |
| 39 | 50 | 0 | 100 | 98 | 73 | 90 | 9 |
| 40 | 250 | 0 | 9 | 69 | 0 | 0 | 0 |
| 41 | 250 | 84 | 0 | 91 | 0 | 17 | 0 |
| 42 | 250 | 96 | 100 | 100 | 100 | 99 | 100 |
| 43 | 250 | 0 | 0 | 0 | 78 | 0 | 0 |
| 44 | 250 | 99 | 100 | 99 | 95 | 99 | 98 |
| 45 | — | — | — | — | — | — | — |
| 46 | — | — | — | — | — | — | — |
| 47 | 250 | 100 | 100 | 98 | 98 | 93 | 92 |
| 48 | 250 | 100 | 100 | 100 | 100 | 99 | 100 |
| 49 | 250 | 100 | 100 | 100 | 100 | 96 | 100 |
| 50 | 250 | 100 | 100 | 100 | 100 | 99 | 100 |
| 51 | 50 | 0 | 9 | 0 | 8 | 30 | 0 |
| 52 | 250 | 100 | 89 | 99 | 13 | 94 | 26 |
| 53 | 50 | 100 | 100 | 100 | 97 | 96 | 97 |
| 54 | 50 | 100 | 100 | 100 | 100 | 97 | 99 |
| 55 | 50 | 100 | 100 | 100 | 100 | 99 | 99 |
| 56 | 50 | 100 | 100 | 100 | 88 | 94 | 91 |
| 57 | 50 | 100 | 100 | 100 | 73 | 96 | 97 |
| 58 | 50 | 24 | 0 | 21 | 0 | 79 | 0 |
| 59 | 50 | 100 | 100 | 100 | 100 | 88 | 98 |
| 60 | 50 | 82 | 99 | 96 | 75 | 87 | 62 |
| 61 | 50 | 63 | 55 | 0 | 0 | 83 | 0 |
| 62 | 50 | 100 | 99 | 76 | 87 | 97 | 0 |
| 63 | 50 | 100 | 100 | 56 | 0 | 97 | 0 |
| 64 | 50 | 97 | 100 | 98 | 99 | 91 | 99 |
| 65 | — | — | — | — | — | — | — |
| 66 | — | — | — | — | — | — | — |
| 67 | 50 | 100 | 100 | 84 | 92 | 98 | 98 |

TABLE A-continued

| Cmpd No. | Rate in ppm | Test A | Test B | Test C | Test D | Test E | Test F |
|---|---|---|---|---|---|---|---|
| 68 | 50 | 100 | 100 | 99 | 100 | 93 | 99 |
| 69 | 50 | 100 | 100 | 99 | 86 | 93 | 99 |
| 70 | 50 | 100 | 100 | 99 | 100 | 96 | 98 |
| 71 | 50 | 87 | 99 | 47 | 92 | 63 | 0 |
| 72 | 50 | 93 | 98 | 21 | 77 | 90 | 0 |
| 73 | — | — | — | — | — | — | — |
| 74 | — | — | — | — | — | — | — |
| 75 | — | — | — | — | — | — | — |
| 76 | — | — | — | — | — | — | — |
| 77 | — | — | — | — | — | — | — |
| 78 | — | — | — | — | — | — | — |
| 79 | — | — | — | — | — | — | — |
| 80 | — | — | — | — | — | — | — |
| 81 | 50 | 0 | 19 | 0 | 0 | 0 | 0 |
| 82 | 50 | 3 | 28 | 0 | 0 | 0 | 0 |
| 83 | 50 | 99 | 100 | 98 | 100 | 94 | 100 |
| 84 | 50 | 100 | 100 | 99 | 100 | 94 | 100 |
| 85 | 50 | 100 | 100 | 99 | 100 | 93 | 100 |
| 86 | 250 | 83 | 98 | 0 | 0 | 43 | 0 |
| 87 | 50 | 100 | 98 | 96 | 100 | 96 | 99 |
| 88 | 250 | 0 | 0 | 0 | 0 | 0 | 0 |
| 89 | 250 | 0 | 0 | 0 | 0 | 0 | 0 |
| 90 | 50 | 99 | 100 | 97 | 100 | 99 | 99 |
| 91 | 250 | 0 | 99 | 0 | 75 | 79 | 17 |
| 92 | 50 | 100 | 100 | 99 | 100 | 96 | 99 |
| 93 | — | — | — | — | — | — | — |
| 94 | 50 | 100 | 100 | 100 | 100 | 98 | 100 |
| 95 | — | — | — | — | — | — | — |
| 96 | 50 | 100 | 100 | 99 | 100 | 98 | 100 |
| 97 | 50 | 100 | 100 | 99 | 100 | 96 | 100 |
| 98 | 250 | 0 | 98 | 0 | 94 | 96 | 0 |
| 99 | 250 | 100 | 100 | 95 | 99 | 93 | 96 |
| 100 | — | — | — | — | — | — | — |
| 101 | 50 | 98 | 99 | 89 | 99 | 98 | 98 |
| 102 | 50 | 97 | 99 | 0 | 99 | 99 | 88 |
| 103 | 50 | 100 | 100 | 97 | 100 | 100 | 99 |
| 104 | — | — | — | — | — | — | — |
| 105 | 50 | 100 | 100 | 95 | 96 | 98 | 100 |
| 106 | — | — | — | — | — | — | — |
| 107 | — | — | — | — | — | — | — |
| 108 | — | — | — | — | — | — | — |
| 109 | — | — | — | — | — | — | — |
| 110 | — | — | — | — | — | — | — |
| 111 | — | — | — | — | — | — | — |
| 112 | — | — | — | — | — | — | — |
| 113 | — | — | — | — | — | — | — |
| 114 | — | — | — | — | — | — | — |
| 115 | — | — | — | — | — | — | — |
| 116 | — | — | — | — | — | — | — |
| 117 | — | — | — | — | — | — | — |
| 118 | 50 | 80 | 99 | 56 | 0 | 97 | 0 |
| 119 | — | — | — | — | — | — | — |
| 120 | — | — | — | — | — | — | — |
| 121 | — | — | — | — | — | — | — |
| 122 | 50 | 0 | 19 | 0 | 0 | 0 | 0 |
| 123 | 50 | 100 | 100 | 100 | 100 | 99 | 100 |
| 124 | 50 | 100 | 100 | 100 | 100 | 99 | 100 |
| 125 | 50 | 3 | 28 | 0 | 0 | 0 | 0 |
| 126 | 50 | 0 | 28 | 0 | 0 | 0 | 0 |
| 127 | 50 | 0 | 41 | 0 | 0 | 0 | 0 |
| 128 | — | — | — | — | — | — | — |
| 129 | 50 | 100 | 100 | 99 | 99 | 98 | 100 |
| 130 | 50 | 100 | 100 | 99 | 98 | 99 | 100 |
| 131 | — | — | — | — | — | — | — |
| 132 | — | — | — | — | — | — | — |
| 133 | — | — | — | — | — | — | — |
| 134 | 50 | 100 | 100 | 86 | 100 | 99 | 99 |
| 135 | 50 | 41 | 89 | 0 | 0 | 94 | 0 |
| 136 | 50 | 82 | 99 | 68 | 0 | 99 | 0 |
| 137 | — | — | — | — | — | — | — |
| 138 | — | — | — | — | — | — | — |
| 139 | — | — | — | — | — | — | — |
| 140 | — | — | — | — | — | — | — |
| 141 | — | — | — | — | — | — | — |
| 142 | — | — | — | — | — | — | — |
| 143 | — | — | — | — | — | — | — |
| 144 | — | — | — | — | — | — | — |
| 145 | — | — | — | — | — | — | — |
| 146 | — | — | — | — | — | — | — |
| 153 | 50 | 0 | 80 | 0 | 0 | 0 | 0 |
| 154 | 50 | 100 | 98 | 35 | 59 | 98 | 0 |
| 155 | 50 | 8 | 89 | 0 | 0 | 92 | 0 |
| 156 | 50 | 100 | 100 | 98 | 99 | 98 | 91 |
| 157 | 50 | 100 | 100 | 96 | 97 | 99 | 98 |
| 158 | 50 | 0 | 68 | 0 | 0 | 40 | 0 |
| 159 | 50 | 100 | 100 | 27 | 77 | 99 | 94 |
| 160 | 250 | 46 | 80 | 0 | 0 | 94 | — |

What is claimed is:

1. A compound selected from Formula 1, tautomers, N-oxides, and salts thereof,

1 wherein

J is

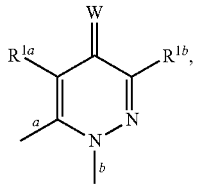

J-2 wherein the bond of J-2 which is identified with "a" is connected to $Q^1$ of Formula 1, and the bond which is identified with "b" is connected to $Q^2$ of Formula 1;

W is O;

$Q^1$ and $Q^2$ are each independently

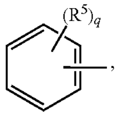

A-1 wherein the floating bond is connected to Formula 1 through any available carbon atom;

each q is independently 2 or 3;

$R^{1a}$ and $R^{1b}$ are each independently H, halogen, cyano, $C_1$-$C_2$ alkyl, $C_1$-$C_2$ haloalkyl, cyclopropyl or $C_1$-$C_2$ hydroxyalkyl;

each $R^5$ is independently cyano, halogen, nitro, $C_1$-$C_2$ alkyl, $C_1$-$C_2$ alkoxy, $C_2$-$C_3$ alkenyloxy or $C_2$-$C_3$ cyanoalkoxy, each optionally substituted with up to 3 substituents independently selected from halogen.

2. A compound of claim 1 wherein $R^{1a}$ and $R^{1b}$ are each independently H, Br, $C_1$, F, cyano, methyl, ethyl or $CH_2F$; and each $R^5$ is independently cyano, halogen, nitro, $C_1$-$C_2$ alkyl, $C_1$-$C_2$ alkoxy or $C_2$-$C_3$ cyanoalkoxy.

3. A compound of claim 2 wherein $R^{1a}$ and $R^{1b}$ are each independently Br, $C_1$, F, methyl or ethyl; and each $R^5$ is independently cyano, Br, $C_1$, F, methyl or methoxy.

4. A compound of claim 3 wherein $R^{1a}$ and $R^{1b}$ are each independently Br, $C_1$, methyl or ethyl; and each $R^5$ is independently Br, $C_1$, F, methyl or methoxy.

5. A compound of claim 4 wherein $R^{1a}$ and $R^{1b}$ are each independently Br, $C_1$ or methyl; and $R^5$ is independently Br, $C_1$, F or methoxy.

6. A compound of claim 1 which is selected from the group:

6-(2,4-difluorophenyl)-1-(3,5-dimethoxyphenyl)-3,5-dimethyl-4 (1//)-pyridazinone;

3-chloro-6-(2-chloro-4-fluorophenyl)-1-(2-chloro-3,5-dimethoxyphenyl)-5-methyl-4 (1H)-pyridazinone;

3-bromo-6-(2-chloro-4-fluorophenyl)-1-(2-chloro-3,5-dimethoxyphenyl)-5-methyl-4 (1H)-pyridazinone;

6-(2-chloro-4-fluorophenyl)-3,5-dimethyl-1-(3,5-dimethoxyphenyl)-4 (1H)-pyridazinone;

5-chloro-1-(2-chloro-5-methoxyphenyl)-6-(4-fluorophenyl)-3-methyl-4 (1H)-pyridazinone;

5-chloro-1-(2-chloro-5-methoxyphenyl)-6-(2-chloro-4-fluorophenyl)-3-methyl-4 (1)-pyridazinone; and 5-bromo-1-(2-chloro-5-methoxyphenyl)-6-(2-chloro-4-fluorophenyl)-3-methyl-4 (1H)-pyridazinone.

7. A fungicidal composition comprising (a) a compound of claim 1; and (b) at least one additional component selected from the group consisting of surfactants, solid diluents and liquid diluents.

8. A method for controlling plant diseases caused by fungal plant pathogens comprising applying to the plant or portion thereof, or to the plant seed, a fungicidally effective amount of a compound of claim 4.

9. A compound of claim 1 that is:

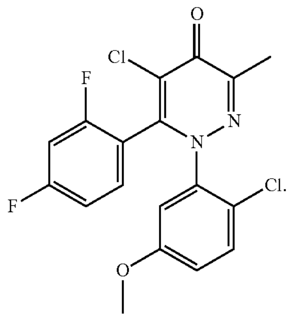

* * * * *